(12) United States Patent
Lee

(10) Patent No.: US 12,170,166 B2
(45) Date of Patent: Dec. 17, 2024

(54) DEVICE FOR GENERATING MAGNETIC FIELD AND METHOD FOR CONTROLLING SAME

(71) Applicant: RADEXEL INC., Chuncheon-si (KR)

(72) Inventor: Jeong Won Lee, Chuncheon-si (KR)

(73) Assignee: RADEXEL INC., Chuncheon-si (KR)

( * ) Notice: Subject to any disclaimer, the term of this patent is extended or adjusted under 35 U.S.C. 154(b) by 142 days.

(21) Appl. No.: 18/049,090

(22) Filed: Oct. 24, 2022

(65) Prior Publication Data

US 2023/0065665 A1 Mar. 2, 2023

Related U.S. Application Data

(63) Continuation of application No. PCT/KR2021/005131, filed on Apr. 23, 2021.

(30) Foreign Application Priority Data

| Apr. 24, 2020 | (KR) | 10-2020-0050313 |
| Apr. 22, 2021 | (KR) | 10-2021-0052174 |

(51) Int. Cl.
| *H01F 7/02* | (2006.01) |
| *A61N 2/02* | (2006.01) |
| *G21K 5/04* | (2006.01) |

(52) U.S. Cl.
CPC ............ *H01F 7/0273* (2013.01); *G21K 5/04* (2013.01); *A61N 2/02* (2013.01)

(58) Field of Classification Search
CPC .......... H01F 7/0273; G21K 5/04; G21K 5/00; A61N 2/02; A61N 2005/1094;

(Continued)

(56) References Cited

U.S. PATENT DOCUMENTS 5,126,985 A * 6/1992 Spruit ............... G11B 11/10513
360/59
9,283,406 B2 3/2016 Prieels
(Continued)

FOREIGN PATENT DOCUMENTS

| CN | 102824957 B | * | 6/2013 | |
| CN | 106999979 A | * | 8/2017 | ............. B05D 3/067 |

(Continued)

OTHER PUBLICATIONS

International Search Report issued in PCT/KR2021/005131; mailed Jul. 26, 2021.

(Continued)

*Primary Examiner* — Abdullah A Riyami
*Assistant Examiner* — Syed M Kaiser
(74) *Attorney, Agent, or Firm* — Studebaker & Brackett PC

(57) ABSTRACT

Disclosed is a radiation and magnetic field generating apparatus irradiating photon beam radiation to in-body affected tissue of a subject. The apparatus includes a radiation generating unit that irradiates the photon beam radiation to the subject and induces generation of secondary electrons in an area of the subject where the photon beam radiation is irradiated, a magnetic field generating unit that includes an insertion structure for forming a low-density space and forms a magnetic field in an area in which the secondary electrons are generated, and a synchronization control unit that controls formation of the magnetic field and controls the formation of the magnetic field such that the secondary electrons move while avoiding normal tissue adjacent to the affected tissue.

19 Claims, 46 Drawing Sheets

(58) Field of Classification Search
CPC ............ A61N 2005/1098; A61N 2/002; A61N 2/004; A61N 5/1077; A61N 5/1042; A61N 5/1002; A61N 5/1014; A61N 5/1031; A61N 5/1045; A61N 5/1067; A61N 2005/1074; A61N 2005/1089
See application file for complete search history.

(56) References Cited

U.S. PATENT DOCUMENTS

| | | |
|---|---|---|
| 9,530,605 B2 | 12/2016 | Nahum et al. |
| 10,080,912 B2 | 9/2018 | Kwak et al. |
| 10,870,018 B2 | 12/2020 | Bartkoski et al. |
| 2006/0262905 A1 | 11/2006 | Reiffel |
| 2013/0259198 A1 | 10/2013 | Alezra et al. |
| 2014/0316185 A1 | 10/2014 | Sandstrom |
| 2015/0094517 A1 | 4/2015 | Prieels |
| 2016/0175616 A1 * | 6/2016 | Kwak .................. A61N 5/1065 378/65 |
| 2017/0106214 A1 | 4/2017 | Kwak et al. |
| 2019/0118000 A1 | 4/2019 | Kwak et al. |
| 2019/0217125 A1 | 7/2019 | Bartkoski et al. |
| 2021/0085999 A1 | 3/2021 | Bartkoski et al. |

FOREIGN PATENT DOCUMENTS

| | | | | |
|---|---|---|---|---|
| CN | 109904938 A * | 6/2019 | | |
| DE | 102013110328 B4 * | 5/2018 | ........... | C23C 14/351 |
| JP | 2001-517132 A | 10/2001 | | |
| JP | 6792731 B2 | 11/2020 | | |
| KR | 10-1617773 B1 | 5/2016 | | |
| KR | 10-1689130 B1 | 12/2016 | | |
| KR | 10-2019-0085914 A | 7/2019 | | |
| KR | 10-2020-0038429 A | 4/2020 | | |
| RU | 2190433 C2 | 10/2002 | | |
| RU | 2209643 C2 | 8/2003 | | |
| WO | WO-2017037519 A1 * | 3/2017 | | |
| WO | 2019/074497 A1 | 4/2019 | | |

OTHER PUBLICATIONS

Chu, J.C.H et al. Modulation of Radiotherapy Photon Beam Intensity Using Magnetic Field; International Journal of Cancer; Jul. 30, 2001; vol. 96, pp. 131-137.

The partial supplementary European search report (R. 164 EPC) issued by the European Patent Office on Aug. 7, 2023, which corresponds to European Patent Application No. 21791842.4-1126 and is related to U.S. Appl. No. 18/049,090.

An Office Action; "Notice of Reasons for Refusal," mailed by the Japanese Patent Office on Aug. 29, 2023, which corresponds to Japanese Patent Application No. 2022-564796 and is related to U.S. Appl. No. 18/049,090.

An Office Action mailed by The Russian Federal Institute of Industrial Property on Apr. 27, 2023, which corresponds to Russian Patent Application No. 2022128563 and is related to U.S. Appl. No. 18/049,090.

An Office Action mailed by The Russian Federal Institute of Industrial Property on Mar. 28, 2024, which corresponds to Russian Patent Application No. 2023128283 and is related to U.S. Appl. No. 18/049,090.

* cited by examiner

DEVICE FOR GENERATING MAGNETIC FIELD AND METHOD FOR CONTROLLING SAME

CROSS-REFERENCE TO RELATED APPLICATIONS

The present application is a continuation of International Patent Application No. PCT/KR2021/005131, filed on Apr. 23, 2021, which is based upon and claims the benefit of priority to Korean Patent Application Nos. 10-2020-0050313 filed on Apr. 24, 2020 and 10-2021-0052174 filed on Apr. 22, 2021. The disclosures of the above-listed applications are hereby incorporated by reference herein in their entirety.

BACKGROUND

Embodiments of the inventive concept described herein relate to a magnetic field generating apparatus and a control method thereof, and more particularly, relate to a magnetic field generating apparatus capable of lowering a duty factor of a magnetic field generating unit by synchronizing a radiation pulse with a magnetic field pulse, and a control method thereof.

Nowadays, as living standards of people are improved with the advent of aging population, interest in early diagnosis and treatment of diseases for leading a healthy life is increasing. In particular, a radiation treatment device refers to a medical device that uses radiation to treat a disease, and is a treatment device that delays the growth of malignant tumor tissue such as cancer or destroys the malignant tumor tissue by using radiation such as photons or proton rays such as X-rays or gamma rays.

By the way, when the amount of radiation with high energy is excessively irradiated to normal tissue of a human body, normal tissue cells may die, may cause genetic defects, or may cause cancer. When normal tissue and tumor tissue are close to each other, the radiation treatment dose may not be sufficiently irradiated due to side effects of radiation. For example, mucosal tissue in a human body is one of the most sensitive portions to radiation. When a specific amount of radiation or more is delivered to the mucosal structure, side effects will occur. Accordingly, during radiation treatment, radiation sufficiently irradiates the tumor to be destroyed, and the amount of radiation needs to be controlled to minimize damage to the normal tissue surrounding the tumor.

In contrast, Korean Patent Registration No. 10-1689130 discloses a photon beam radiation therapy device for controlling the radiation dose of mucosal tissue in a body by using a magnetic field. However, a magnetic field generating unit was oversized, and thus there was a limitation in commercialization. For example, while radiation is irradiated to a patient's tumor, the magnetic field generating unit continuously generates a magnetic field, and thus the operating time of the magnetic field generating unit increases. This led to an increase in the caloric value and voltage consumption of an electromagnet that generates the magnetic field. Accordingly, to suppress heat and to supply sufficient voltage, the sizes of a cooling device and a power supply device applied to the magnetic field generating unit is manufactured to be large. Accordingly, the treatment of a patient may be restricted by limiting the treatment space where the patient is located.

In the meantime, when a magnetic field is frequently generated in the magnetic field generating unit, an electron beam in a linear accelerator constituting a radiation treatment device is influenced in addition to malfunction of the radiation treatment device due to external leakage magnetic field. It may cause a change in the amount of radiation or may interfere with accurate beam targeting to tumor tissue, and thus it makes accurate radiation treatment difficult.

SUMMARY

Embodiments of the inventive concept provide a miniaturized magnetic field generating apparatus while a duty factor of a magnetic field generating unit, a caloric value of the magnetic field generating unit, and an external leakage of a magnetic field are lowered.

Embodiments of the inventive concept provide a magnetic field generating apparatus capable of effectively suppressing the influence of a magnetic field on a linear accelerator, an electron gun, or a multi-leaf collimator by placing a magnetic field generating unit inside a magnetic field shield unit.

Problems to be solved by the inventive concept are not limited to the problems mentioned above, and other problems not mentioned will be clearly understood by those skilled in the art from the following description.

According to an embodiment, a radiation and magnetic field generating apparatus, the radiation and magnetic field generating apparatus irradiating photon beam radiation to an in-body affected tissue of a subject includes a radiation generating unit for irradiating the photon beam radiation to the subject, the radiation generating unit for inducing generation of secondary electrons in an area of the subject irradiated with the photon beam radiation, and a magnetic field generating unit, which is provided to be inserted into a body, which includes an insertion structure for forming a low-density space, and which forms a magnetic field in an area in which the secondary electrons are generated, and a synchronization control unit for controlling formation of the magnetic field such that at least part of the secondary electrons moves to the low-density space based on a relationship between an area where the photon beam radiation is irradiated and a location of the affected part, the synchronization control unit for controlling formation of the magnetic field such that the secondary electrons move while avoiding normal tissue adjacent to the affected tissue.

A shape of the insertion structure may be determined based on the relationship between the area where the photon beam radiation is irradiated and the location of the affected part.

In the case, the insertion structure may be inserted into the body, and may be provided as a balloon structure that forms the low-density space through formation of a predetermined volume.

Moreover, the magnetic field generating unit includes at least one coil and a capacitor element, in the case, the synchronization control unit may form the magnetic field by controlling a current supplied to the at least one coil based on the relationship between the area where the photon beam radiation is irradiated and the location of the affected part.

Furthermore, the magnetic field generating unit may be provided such that the magnetic field in a form of a pulse is generated by receiving pulse power, in the case, the synchronization control unit may allow the pulse power to be supplied to the magnetic field generating unit such that the magnetic field is formed in a state where a caloric value generated by the magnetic field generating unit is not greater than a predetermined value.

Besides, the synchronization control unit may include size information of the subject, may include identification information corresponding to the subject, and may control the formation of the magnetic field based on the identification information.

Also, the magnetic field generating unit may be provided in a catheter structure including a first area provided to be inserted into the body and a second area excluding the first area, the at least one coil may be provided in the first area, and the capacitor may be provided in the second area.

Moreover, the synchronization control unit may change a location of at least one magnet or the location of the subject such that an angle between a magnetic force line corresponding to the magnetic field and an irradiation direction of the photon beam radiation is orthogonal.

Furthermore, the synchronization control unit may control the formation of the magnetic field such that density of the secondary electrons reaching the normal tissue per unit area is less than a predetermined value.

Also, the synchronization control unit may control formation of the photon beam radiation such that density of the secondary electrons reaching the affected part per unit area is greater than a predetermined value.

According to an embodiment, a method of controlling a radiation and magnetic field generating apparatus irradiating photon beam radiation to an in-body affected tissue of a subject includes: irradiating the photon beam radiation to the subject through a radiation generating unit of the magnetic field generating apparatus, inducing generation of secondary electrons in an area of the subject irradiated with the photon beam radiation through the radiation generating unit of the magnetic field generating apparatus, and forming a magnetic field in an area where the secondary electrons are generated, through the magnetic field generating unit of the radiation generating apparatus, the forming of the magnetic field includes forming the magnetic field such that at least some of the secondary electrons move while avoiding the affected tissue based on a relationship between an area where the photon beam radiation is irradiated and a location of an affected part, the forming of the magnetic field includes: allowing the pulse power to be supplied to the magnetic field generating unit such that a magnetic field is formed in a state where a caloric value generated by the magnetic field generating unit is not greater than a predetermined value.

DETAILED DESCRIPTION

Figure 1:
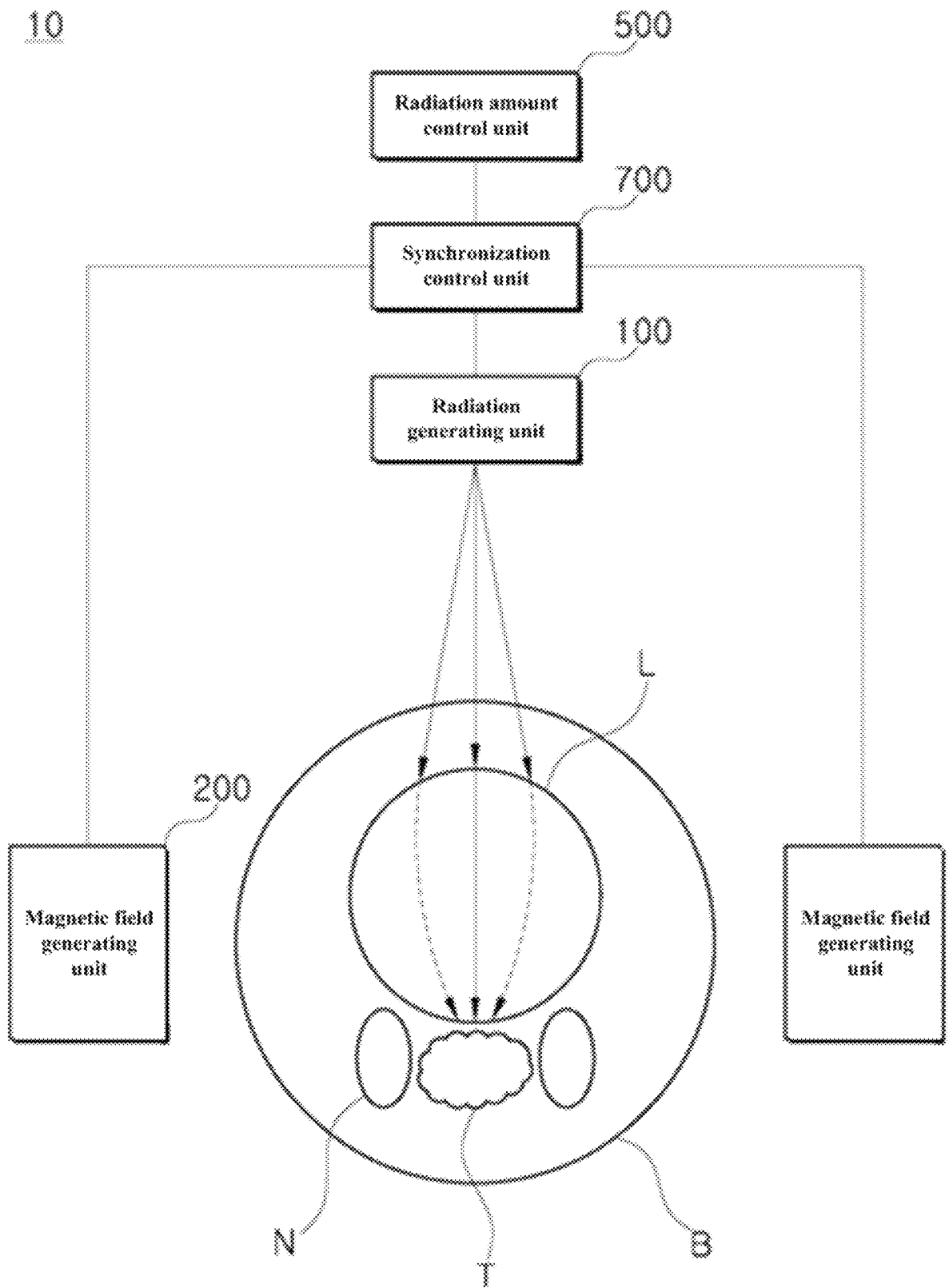
FIGS. 1 and 2 are conceptual diagrams schematically showing a radiation treatment device, according to an embodiment of the inventive concept.

The above and other aspects, features and advantages of the inventive concept will become apparent from embodiments to be described in detail in conjunction with the accompanying drawings. The inventive concept, however, may be embodied in various different forms, and should not be construed as being limited only to the illustrated embodiments. Rather, these embodiments are provided as examples so that the inventive concept will be thorough and complete, and will fully convey the scope of the inventive concept to those skilled in the art. The inventive concept may be defined by the scope of the claims.

The terms used herein are provided to describe embodiments, not intended to limit the inventive concept. In the specification, the singular forms include plural forms unless particularly mentioned. The terms "comprises" and/or "comprising" used herein do not exclude the presence or addition of one or more other components, in addition to the aforementioned components. The same reference numerals denote the same components throughout the specification. As used herein, the term "and/or" includes each of the associated components and all combinations of one or more of the associated components. It will be understood that, although the terms "first", "second", etc., may be used herein to describe various components, these components should not be limited by these terms. These terms are only used to distinguish one component from another component. Thus, a first component that is discussed below could be termed a second component without departing from the technical idea of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

As illustrated in the figures, spatially relative terms, such as "below", "beneath", "lower", "above", "upper", and the like, may be used herein for ease of description to describe the relationship between one component and other components. It will be understood that the spatially relative terms are intended to encompass different orientations of the components in use or operation in addition to the orientation depicted in the figures. For example, when inverting a component shown in the figures, a component described as "below" or "beneath" of another component may be placed "above" another element. Thus, the exemplary term "below" may include both downward and upward directions. The components may also be oriented in different directions, and thus the spatially relative terms may be interpreted depending on orientation.

Hereinafter, embodiments of the inventive concept will be described in detail with reference to accompanying drawings.

Figure 2:
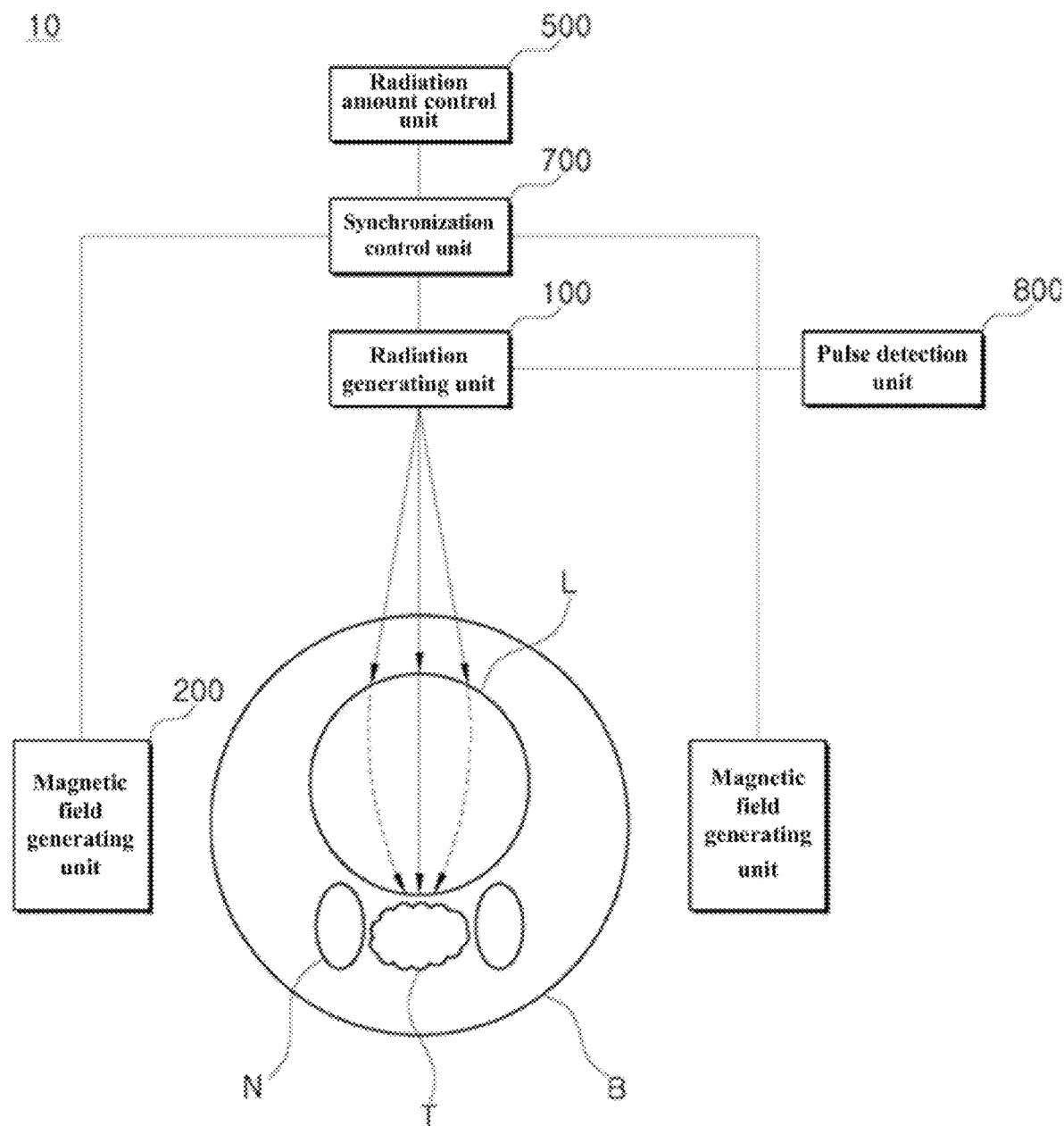

FIGS. 1 and 2 are conceptual diagrams schematically showing a radiation treatment device, according to an embodiment of the inventive concept.

Referring to FIG. 1, a radiation treatment device 10 according to an embodiment of the inventive concept may include a magnetic field generating apparatus. The magnetic field generating apparatus may include a magnetic field generating unit 200 and a synchronization control unit 700. In other words, the radiation treatment device 10 may further include a magnetic field generating apparatus while including a radiation generating unit 100 and a radiation amount control unit 500 as a basic configuration. Accordingly, it is understood that a description that the radiation treatment device 10 operates in conjunction with the magnetic field generating apparatus corresponding to a description of a configuration in which the magnetic field generating apparatus is additionally included in the radiation treatment device 10.

In an embodiment, the radiation treatment device 10 may operate in conjunction with a magnetic field generating apparatus. The two devices may operate in conjunction with each other by using a communication network or by detecting photon beam radiation. Alternatively, in an interworking method, the generation period of a magnetic field or a photon beam may be set in advance such that the two devices operate in conjunction with each other.

In an embodiment, tumor 'T', normal tissue 'N' and low-density space are located inside a patient 'B', and the low-density space may be adjacent to at least one of the tumor 'T' or the normal tissue 'N'. The low-density space in a body such as an oral cavity, a nasal cavity, an airway, and a lung may be a space that normally is present, or may be an artificial space formed by inserting air, inserting a balloon, or injecting a foaming agent. Moreover, the low-density space may be a space through which secondary electrons generated from photon beam radiation pass. In addition, the low-density space may include an empty space in a body or a body cavity.

In an embodiment, the radiation generating unit 100 of the radiation treatment device 10 may irradiate photon beam radiation to affected tissue (e.g., tumor, T) of a subject (e.g., patient, B).

In an embodiment, the radiation amount control unit 500 of the radiation treatment device 10 may diffract electrons in the low-density space in the body by adjusting the intensity, direction and phase of a magnetic field. Accordingly, the radiation amount control unit 500 of the radiation treatment device 10 may control the amount of radiation absorbed by the tumor 'T' of the patient 'B' and the normal tissue 'N' adjacent to the tumor 'T'. For example, the radiation treatment device 10 and the magnetic field generating apparatus operate in conjunction with each other such that the radiation amount control unit 500 allows the magnetic field generating unit 200 to adjust the intensity direction and phase of a magnetic field. In this case, the synchronization control unit 700 may control a generation time range of a magnetic field pulse.

In an embodiment, the magnetic field generating unit 200 of the magnetic field generating apparatus may form a magnetic field inside the patient 'B'. For example, the magnetic field generating unit 200 may form a magnetic field in the low-density space 'L'.

In an embodiment, the synchronization control unit 700 of the magnetic field generating apparatus may synchronize a radiation pulse corresponding to a photon beam radiation and a magnetic field pulse corresponding to a magnetic field. Here, the synchronization of pulses may mean that occurrences of pulses overlap each other in time. For example, the synchronization control unit 700 may match the generation timing of a photon beam radiation pulse with the generation timing of a magnetic field pulse.

In an embodiment, the synchronization control unit 700 of the magnetic field generating apparatus may operate in conjunction with the radiation amount control unit 500 of the radiation treatment device. The synchronization control unit 700 may receive an output period of photon beam radiation from the radiation amount control unit 500 and then may synchronize the output period of the photon beam radiation with the output period of the magnetic field.

In an embodiment, the magnetic field generating apparatus may further include a pulse detection unit 800 for detecting photon beam radiation. For example, the pulse detection unit 800 may detect a magnetic field pulse and a radiation pulse. The pulse detection unit 800 may receive the magnetic field pulse and the radiation pulse from the magnetic field generating unit 200 and the radiation generating unit 100, respectively, through a wired or wireless network and then may detect the magnetic field pulse and the radiation pulse. Furthermore, the pulse detection unit 800 may detect the magnetic field pulse and the radiation pulse by analyzing the radiation and magnetic field, which are externally obtained. To this end, the pulse detection unit 800 may include a radiation detection sensor (not shown) and a magnetic field sensor (not shown).

In an embodiment, the synchronization control unit 700 of the magnetic field generating apparatus may obtain an output period of the photon beam radiation by analyzing the photon beam radiation detected by the pulse detection unit 800.

In an embodiment, the synchronization control unit of the magnetic field generating apparatus may set a magnetic field generation range such that a secondary electron generation section generated due to the irradiation of photon beam radiation is included in a magnetic field generation time range after the magnetic field reaches a target value. Accordingly, secondary electrons generated by the reaction of photon beam radiation with human material (e.g., normal tissue located on a path where radiation progresses toward tumor) may be generated at a magnetic field generation time.

In an embodiment, the synchronization control unit 700 of the magnetic field generating apparatus may set the magnetic field generation time range in consideration of a delay time until the magnetic field reaches a target value. Accordingly, secondary electrons generated by the reaction of photon beam radiation with human material (e.g., normal tissue located on a path where radiation progresses toward tumor) may be generated at a magnetic field generation time in consideration of the delay time.

In an embodiment, the synchronization control unit 700 may recognize the photon beam radiation pulse every time and then may promptly generate magnetic field pulses or vice versa. For example, the synchronization control unit 700 may generate a magnetic field pulse in response to detection of a radiation pulse or may generate the radiation pulse in response to detection of a magnetic field pulse. Furthermore, the synchronization control unit 700 may learn the regularity of a radiation pulse and then may generate pulses of a magnetic field or vice versa. For example, the synchronization control unit 700 may generate a magnetic field pulse based on a radiation pulse period obtained by analyzing the detected radiation pulse or may generate a radiation pulse based on a magnetic field pulse period obtained by analyzing the detected magnetic field pulse. In addition, when a preset radiation pulse period and a preset magnetic field pulse period are present, the synchronization control unit 700 may synchronize the radiation pulse and the magnetic field pulse by matching the radiation pulse period and the magnetic field pulse period.

As such, as the synchronization control unit 700 matches the generation timing of the radiation pulse with the generation timing of the magnetic field pulse, the magnetic field generating unit 200 does not need to continuously generate a magnetic field while photon beam radiation is irradiated, thereby greatly reducing a duty factor. In addition, as the duty factor of the magnetic field generating unit 200 decreases, the magnetic field generating unit 200 does not need to be driven as much as the duty factor of the magnetic field generating unit 200 decreases, Accordingly, the caloric value of the magnetic field generating unit 200 may also be lowered, and the external leakage of the magnetic field is also lowered. As a result, a cooling device that controls the heat generated by the magnetic field generating unit 200 and a power supply device that supplies power may be downsized. This may lead to miniaturization of the radiation treatment device 10.

Besides, as the synchronization control unit 700 matches the generation timing of the radiation pulse with the generation timing of the magnetic field pulse, and thus heat generation may be reduced by reducing the power used by the magnetic field generating unit 200. Accordingly, a component such as a cooling device may be excluded or reduced.

In the meantime, the synchronization control unit 700 according to an embodiment of the inventive concept may control formation of a magnetic field such that at least some of secondary electrons avoid normal tissue adjacent to affected tissue based on a location relationship between an area irradiated with photon beam radiation and an affected part.

That is, when photon beam radiation is irradiated to a subject, secondary electrons are generated in the corresponding area. When the secondary electrons reach a subject corresponding to normal tissue adjacent to affected tissue too much, the subject's tissue may be damaged. Accordingly, some secondary electrons need to avoid normal tissue adjacent to the affected tissue.

In the meantime, the magnetic field generating unit 200 for the above-described operation may include at least one coil and a capacitor element.

The coil may be provided in a configuration for forming a pulse-type magnetic field. The capacitor may be provided to accumulate charges to output a large current. A detailed description related thereto will be given later.

Moreover, the synchronization control unit 700 may form a magnetic field by controlling the current supplied to at least one coil based on a location relationship between an area irradiated with photon beam radiation and the affected part.

In detail, the synchronization control unit 700 may consider a distance from an area, where the photon beam irradiation is irradiated, to the affected part.

Besides, a path of secondary electrons is changed by a magnetic field generated by the magnetic field generating unit 200. The magnetic field generated by the magnetic field generating unit 200 may be formed based on a current supplied by the synchronization control unit 700.

In the meantime, the magnetic field generating unit 200 may be provided to generate a magnetic field in a form of a pulse by receiving pulse power.

The magnetic field generating unit 200 may be provided to generate a magnetic field in a form of a pulse to reduce a caloric value.

Moreover, under the control of the synchronization control unit 700, the pulse power may be supplied to the magnetic field generating unit 200 to form a magnetic field in a state where the caloric value generated by the magnetic field generating unit 200 is not greater than a predetermined value.

That is, the synchronization control unit 700 may monitor the caloric value of the magnetic field generating unit 200 and then may supply the pulse power to the magnetic field generating unit such that the caloric value generated by the pulse power supplied to the magnetic field generating unit does not exceed a specific value.

The synchronization control unit 700 may include size information of a subject, and may include identification information corresponding to the subject.

The identification information may refer to information including not only the location and size of the subject, but also the feature of the subject itself.

In the meantime, the synchronization control unit may control the formation of a magnetic field based on the identification information.

For example, because the secondary electron needs to avoid an affected part on a short path of the secondary electron when the size of subject is small, the synchronization control unit may supply a strong current to the magnetic field generating unit to form a strong magnetic field.

The magnetic field generating unit may be provided in a catheter structure including a first area provided to be inserted into a body and a second area excluding the first area.

The catheter may refer to a tubular instrument for insertion into a body cavity or an organ with a lumen.

The at least one coil may be provided in the first area, and the capacitor may be provided in the second area.

The first area may mean an area inserted into a body when an operation using the catheter is performed. The second area may mean an area provided outside the body when the operation is performed.

In the meantime, the synchronization control unit may determine the irradiation direction of the photon beam radiation based on a location relationship between the radiation generating unit and the subject.

The formation of the magnetic field may be controlled such that an angle between a magnetic force line corresponding to a magnetic field and the irradiation direction of the photon beam radiation exceeds a predetermined angle.

The synchronization control unit 700 may change a location of at least one magnet or a location of the subject such that an angle between the magnetic force line corresponding to the magnetic field and the irradiation direction of the photon beam radiation is orthogonal.

Because the secondary electrons generate electromagnetic force so much when the direction of magnetic force line is perpendicular to the traveling direction of electrons, the synchronization control unit may control the operation of a magnet included in the magnetic field generating unit or a plate-shaped frame provided in the magnetic field generating apparatus such that an angle between the magnetic force line and the irradiation direction of the photon beam radiation is orthogonal.

The synchronization control unit 700 may control the formation of the magnetic field such that reach density of secondary electrons reaching the subject per unit area is less than a predetermined value.

The synchronization control unit 700 may prevent tissue damage of the subject by controlling the reach density of the secondary electrons.

The synchronization control unit 700 may control the formation of photon beam radiation such that the reach density of secondary electrons reaching an affected part per unit area exceeds the predetermined value.

That is, the secondary electrons having a specific density or more need to be delivered to the affected part to achieve the purpose of radiation irradiation.

Accordingly, the synchronization control unit may control the radiation control unit such that the photon beam radiation generated from the radiation generating unit is irradiated to the subject corresponding to the affected part.

A defocusing embodiment in the case where the radiation irradiation direction is perpendicular to the magnetic field direction will be described with reference to FIGS. 3 to 5. A focusing embodiment in the case where the radiation irradiation direction is parallel to the magnetic field direction will be described with reference to FIGS. 6 and 7. For example, it is described that a magnetic field is formed in a direction perpendicular to a photon beam radiation irradiation direction when there is a target location after secondary electrons passes through the body cavity, after normal tissue is placed further. Moreover, it is described that a magnetic field is formed in a direction horizontal to (parallel to) a photon beam radiation irradiation direction such that secondary electrons passing through the body cavity are intensively provided to the target portion because a target portion is located on the surface of a body cavity. Here, the target portion may be an affected tissue (or a tumor portion).

An example of generating a magnetic field in a direction perpendicular to a photon beam radiation irradiation direction corresponds to an embodiment of forming a space in a patient's rectum by inserting a balloon into the rectum, when prostate cancer placed adjacent to the rectum is treated, and dispersing secondary electrons provided on a rectal surface as a magnetic field is formed in an internal space of the rectum.

Figure 3:
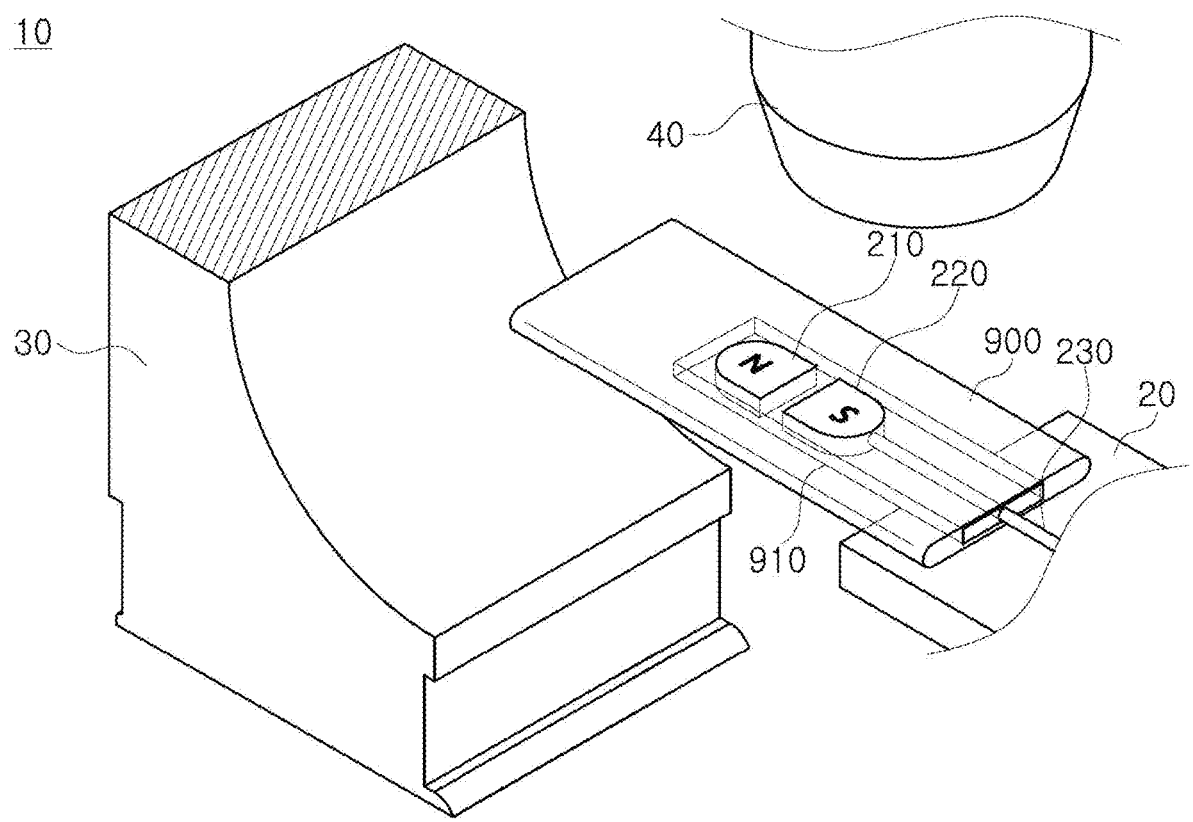
FIG. 3 is a perspective view schematically illustrating a magnetic field generating apparatus, according to an embodiment of the inventive concept.
Figure 4A:
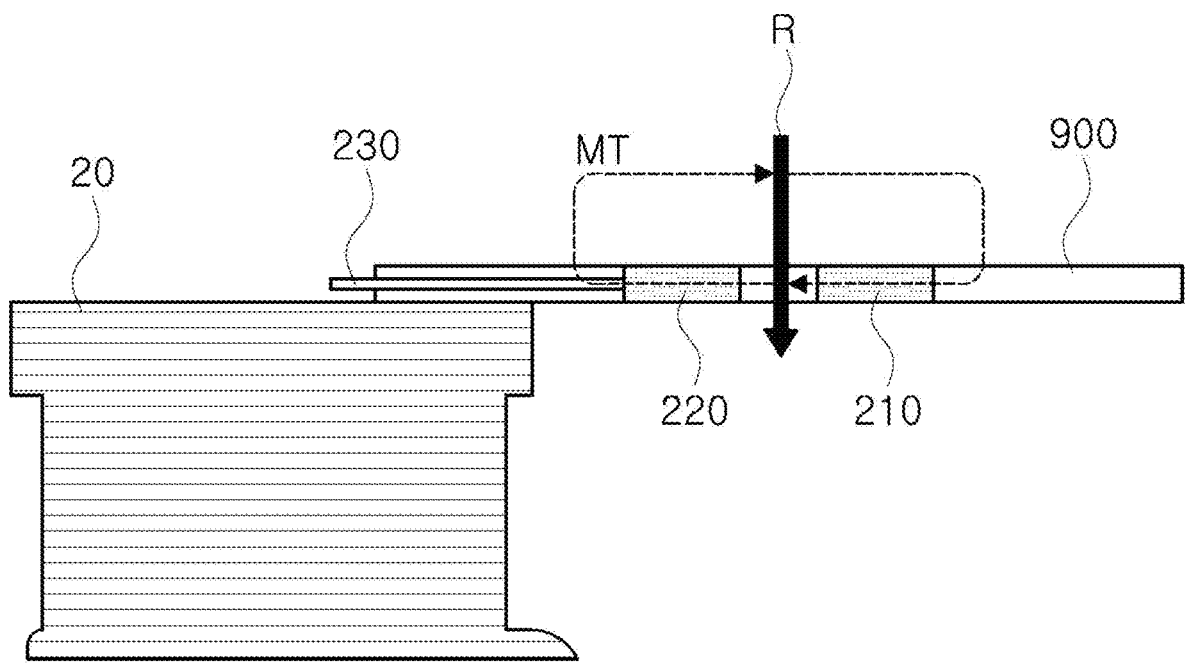
FIGS. 4A to 4E are cross-sectional views schematically illustrating a magnetic field distribution of a magnetic field generating apparatus, according to an embodiment of the inventive concept.
Figure 4B:
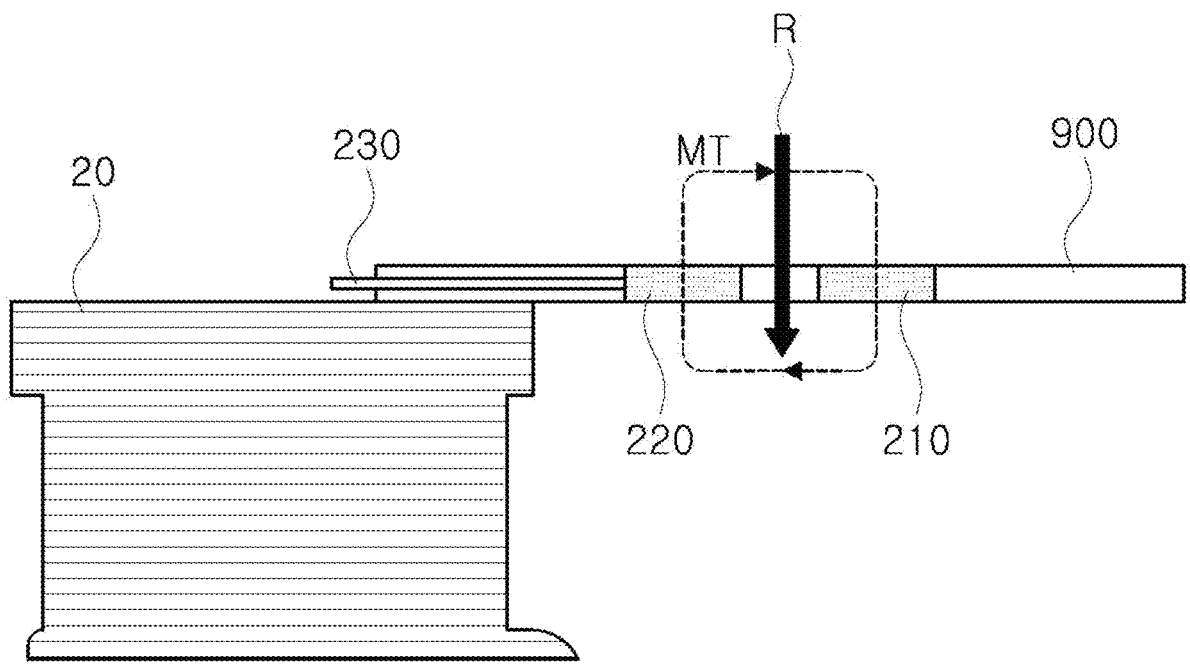
Figure 4C:
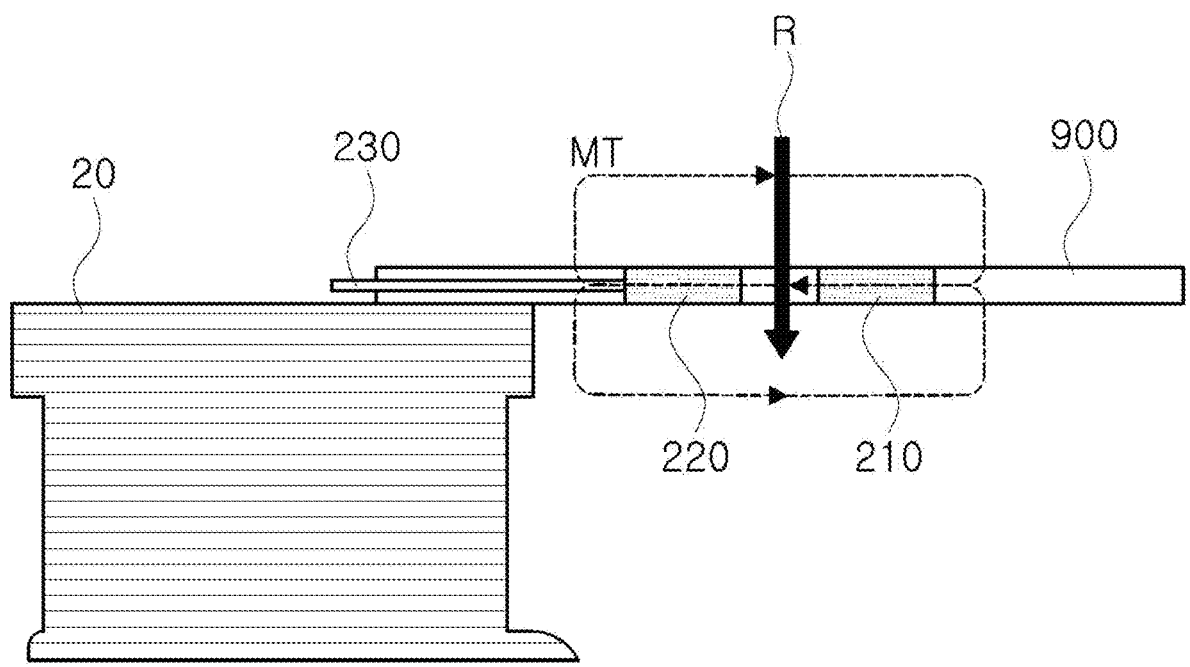
Figure 4D:
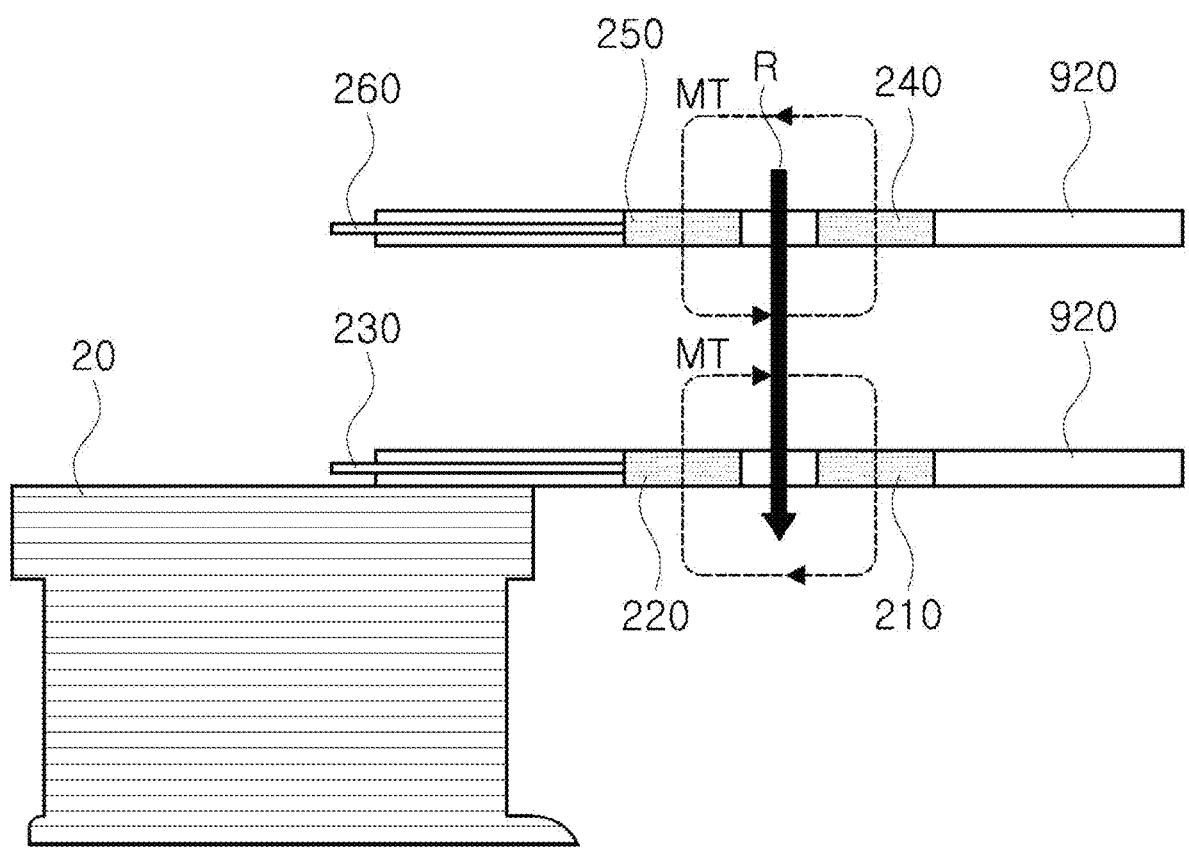
Figure 4E:
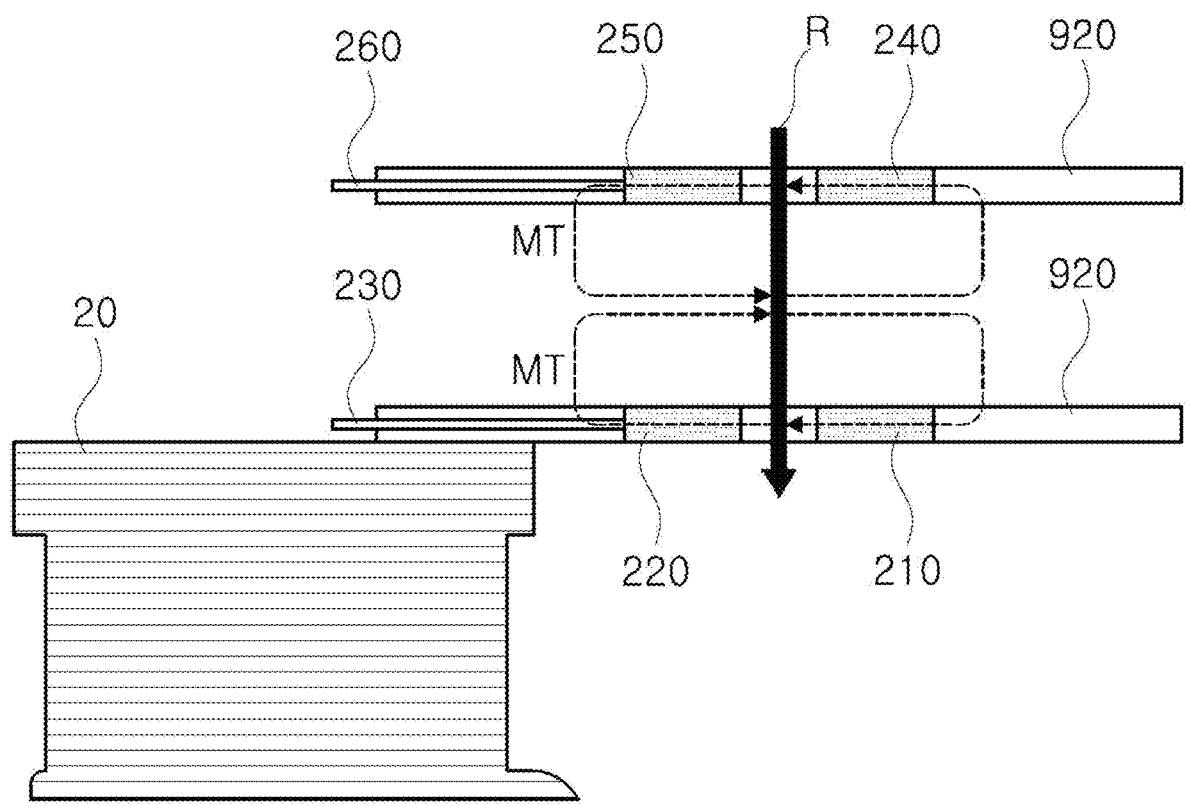
Figure 5:
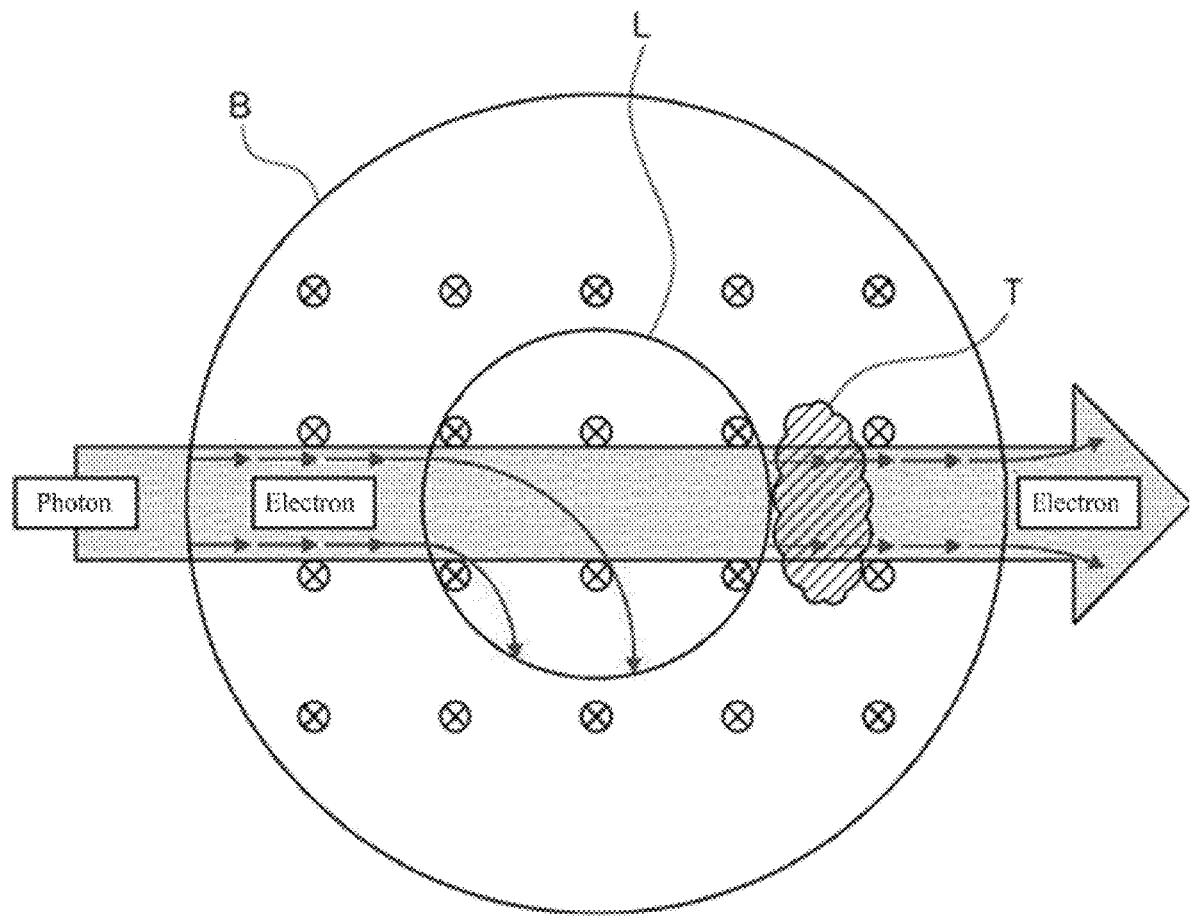
FIG. 5 is a schematic conceptual diagram for describing an operating relationship between charged particles (e.g., electrons) and a magnetic field according to radiation irradiation in a radiation treatment device using a magnetic field of FIGS. 4A to 4E.

FIGS. 3 to 5 relate to an example in which a magnetic field is generated in a direction perpendicular to the radiation irradiation direction. FIG. 3 is a perspective view schematically illustrating a magnetic field generating apparatus, according to an embodiment of the inventive concept. FIGS. 4A to 4E are cross-sectional views schematically illustrating a magnetic field distribution of a magnetic field generating apparatus, according to an embodiment of the inventive concept. FIG. 5 is a schematic conceptual diagram for describing an operating relationship between charged particles (e.g., electrons) and a magnetic field according to radiation irradiation in a radiation treatment device using a magnetic field of FIGS. 4A to 4E.

Referring to FIGS. 3 and 4A to 4E, the radiation treatment device 10 may include housings 20, 30, and 40 having various shapes in each of which each component is capable of being placed. A structure of the housing may be variously modified to irradiate radiation to a lying patient and to generate a magnetic field.

The radiation generating unit 100 of the radiation treatment device 10 may be mounted in a shielding structure disposed outside of a bore (not shown) having a hollow shape to irradiate photon beam radiation toward a portion of the tumor 'T' of the patient 'B' located within the bore.

Here, the radiation generating unit 100 of the radiation treatment device 10 is preferably a linear accelerator (LINAC) for generating an MV X-ray. Kinetic energy is delivered to secondary electrons (hereinafter referred to as 'electrons') through a reaction by Compton effect on a surface of a material exposed due to the nature of the generated X-ray beam of an MV area, and the amount of radiation is delivered to the body by the electrons.

The magnetic field generating unit 200 of the magnetic field generating apparatus may be mounted in another shielding structure positioned outside the bore to form a magnetic field area in the body of the patient 'B'. The magnetic field generating unit 200 consists of a pair of electromagnets, or permanent magnets, which are positioned to be opposite to each other and which have different polarities with a bore therebetween.

Here, the magnetic field generating unit 200 of the magnetic field generating apparatus forms a magnetic field area in an area (more preferably, an empty space in the body or body cavity) in the body of the patient 'B' between the radiation generating unit 100 and the tumor 'T' portion of the patient 'B'. In addition, the magnetic field generating unit 200 may include an electromagnet, a permanent magnet, or a combination thereof.

In the meantime, to increase the degree of freedom in a direction of the magnetic field, a pair of magnets that are the magnetic field generating unit 200 may rotate along an outer perimeter of the bore (e.g., the patient 'B' located within the bore), but not limited thereto. For example, the magnetic field generating unit 200 may form a magnetic field area by using a magnet selected from among a plurality of magnets through the control of the radiation amount control unit while the plurality of magnets are fixedly positioned along the outer perimeter of the bore (e.g., the perimeter of the patient 'B').

In an embodiment, unlike descriptions above, the magnetic field generating apparatus may further include a plate-shaped frame 900 in which the magnetic field generating unit 200 is positioned. A patient may be seated on the plate-shaped frame 900, and the magnetic field generating material may be placed on the plate-shaped frame 900. For example, the plate-shaped frame 900 may have a space 910 in which the magnetic field generating material moves, and the magnetic field generating material may be positioned in space 910. For example, the space 910 may be elongated in a longitudinal direction of the plate-shaped frame 900 as shown in FIG. 3 such that the magnetic field generating material is capable of moving. The length of the space 910 is shown in FIG. 3, and the space 910 may be elongated to opposite ends of the plate-shaped frame 900.

In an embodiment, the magnetic field generating material may be connected to a moving rod 230. The moving rod 230 may move in the length direction of the plate-shaped frame 900 in the space 910 through a separate driving unit (not shown). Accordingly, as the magnetic field generating material moves depending on the location of the patient the magnetic field generation area in the patient's body may be easily changed.

In an embodiment, the magnetic field generating unit 200 may include a plurality of electromagnets, permanent magnets, or a combination (hereinafter collectively referred to as a "magnetic field generating material") thereof, which are arranged in a left-right symmetrical structure with respect to an axis to which the photon beam radiation is irradiated, and may generate a magnetic field MT as shown in FIG. 4.

For example, in FIG. 4A, an N-pole electromagnet 210 of the and an S-pole electromagnet 220 may be arranged, and the magnetic field generating unit 200 may generate the magnetic field MT in a direction perpendicular to a radiation irradiation direction 'R'. Here, the magnetic field generating unit 200 may form an effective area on the plate-shaped frame 900 in the length direction of the electromagnets 210 and 220 as shown in FIG. 4A. Furthermore, according to an embodiment, a magnetic field shield unit may be included under the magnetic field generating unit 200, and thus a magnetic field may not be formed under the plate-shaped frame. That is, there is no need to form a magnetic field under the plate-shaped frame that does not affect the radiation treatment for the patient, and it is necessary to prevent the influence of magnetic field on a device such as a radiation treatment device. Accordingly, the magnetic field shield unit may be included under the magnetic field generating unit 200 within the plate-shaped frame.

Moreover, for example, as illustrated in FIG. 4B, the N-pole electromagnet 210 of the and the S-pole electromagnet 220 may be arranged, and the magnetic field generating unit 200 may generate the magnetic field MT in a direction perpendicular to a radiation irradiation direction 'R'. The magnetic field generating unit 200 may form the effective area above and below the plate-shaped frame 900 as shown in FIG. 4B while the area size of the effective area is smaller than an area size in which the electromagnets 210 and 220 are disposed.

Moreover, for example, as illustrated in FIG. 4C, the N-pole electromagnet 210 of the and the S-pole electromagnet 220 may be arranged, and the magnetic field generating unit 200 may generate the magnetic field MT in a direction perpendicular to a radiation irradiation direction 'R'. The magnetic field generating unit 200 may form the effective area above and below the plate-shaped frame 900 as shown in FIG. 4C while the area size of the effective area is greater than an area size in which the electromagnets 210 and 220 are disposed.

Moreover, for example, as illustrated in FIG. 4C, the N-pole electromagnet 210 and the S-pole electromagnet 220 may be positioned on a lower plate-shaped frame 920, and an N-pole electromagnet 240 and an S-pole electromagnet 250 may be positioned on an upper plate-shaped frame 920. Accordingly, the magnetic field generating unit 200 may generate the two magnetic fields MT in a direction perpendicular to a radiation irradiation direction 'R'. Here, the magnetic field generating unit 200 may form the effective area above and below each of the upper plate-shaped frame 920 and the lower plate-shaped frame 920 as shown in FIG. 4D while the area size of the effective area is smaller than an area size in which the electromagnets 210, 220, 240, and 250 are disposed. In this case, the intensity of a magnetic field between the plate-shaped frames 920 may be stronger.

Moreover, for example, as illustrated in FIG. 4E, the N-pole electromagnet 210 and the S-pole electromagnet 220 may be positioned on the lower plate-shaped frame 920, and the N-pole electromagnet 240 and the S-pole electromagnet 250 may be positioned on the upper plate-shaped frame 920. Accordingly, the magnetic field generating unit 200 may generate the two magnetic fields MT in a direction perpendicular to a radiation irradiation direction 'R'. The magnetic field generating unit 200 may form the effective area between the plate-shaped frame 920 as shown in FIG. 4E while the area size of the effective area is smaller than an area size in which the electromagnets 210, 220, 240, and 250 are disposed.

In an embodiment, the radiation amount control unit 500 of the radiation treatment device controls the amount of radiation delivered from the radiation generating unit 100 to a portion of the tumor 'T' of the patient by adjusting the direction, intensity, and phase of the magnetic field of the magnetic field generating unit 200. For example, when the magnetic field is a pulse wave in a form of a sine wave, the radiation amount control unit 500 may change the phase of the magnetic field, and may match a section having the desired reference intensity or higher in the sine wave with a section in which secondary electrons are generated by photon beam radiation.

In an embodiment, the radiation amount control unit 500 may further include a calculating unit (not shown) that controls an operation of the radiation generating unit 100 and calculates the amount of radiation delivered to the tumor 'T'.

In an embodiment, the calculating unit may calculate the amount of radiation delivered to the tumor 'T' of the patient 'B' by using Equation 1 below.

$$D(x,y,z) = \iiint TERMA(x',y',z') \times Kernel(x,x',y,y',z,z') \, dx'dy'dz'$$ [Equation 1]

Here, $D(x,y,z)$ denotes a value of the amount of radiation absorbed at a specific location $(x,y,z)$; $TERMA(x', y', z')$ denotes the total energy of the incident radiation beam attenuated in a minute volume $dx'dy'dz'$; and, $Kernel(x, x', y, y', z, z')$ denotes a rate of dose absorbed at a specific location $(x,y,z)$ by unit energy attenuated in the minute volume dx'dy'dz'. At this time, a kernel that considering a magnetic field formed by the magnetic field generating unit 200 is used.

Accordingly, when the TERMA value and the Kernel value are convolved with respect to the whole volume, the absorbed radiation amount value at a specific location (x,y,z) may be calculated.

In the meantime, the TERMA value indicates the total attenuated energy of uncharged x-rays, and thus it is not related to the magnetic field.

Moreover, because the Kernel value indicates a spatial dose distribution by electrons mainly generated during an attenuation process, the Kernel value is absolutely influenced by the magnetic field. In general, when the kernel is obtained, it is obtained through computational simulation. A new kernel is obtained by implementing a spatially constant magnetic field in a computer simulation program, and the Kernel Deform map is configured as follows. This is modeled and applied as in Equation 2 below.

$$\text{Kernel}_{new}(B,x,x',y,y',z,z')=\text{Deform\_map}(\text{Kernel}(x,x',y,y',z,z'),B) \quad \text{[Equation 2]}$$

Accordingly, the calculating unit calculates the intensity, direction phase, and magnitude of the magnetic field for optimizing the distribution of a radiation amount.

Meanwhile, in another embodiment, the calculating unit may be calculated by a Full Monte Carlo simulation method.

In other words, the calculating unit may use a toolkit capable of simulating a magnetic field, may construct a history by using the probabilistic Monte Carlo method for each particle, may calculate the overall dose distribution by adding the spatial influence of each dose in the histories, and may calculate the absorbed radiation amount value at a specific location.

Referring to FIG. 5, according to the configuration described in FIGS. 3 and 4A to 4E, a process of radiation treatment of the tumor T of the patient 'B' by using the radiation treatment device 10 for controlling body dose using a magnetic field according to an embodiment of the inventive concept is as follows.

Prior to descriptions, hereinafter, according to an embodiment, as shown in FIG. 5, when photon beam radiation is irradiated from the radiation generating unit 100 positioned on the left side of FIG. 5 to the tumor 'T' positioned on the right side of FIG. 5, the magnetic field operates in the entering direction of the ground, and an organ such as a hollow digestive system (stomach, small intestine, large intestine, or the like) is placed between the radiation generating unit 100 and the tumor 'T', the treatment of the tumor T will be described.

First of all, while the patient 'B', who has the tumor 'T' to be treated, lies on the plate-shaped frame 900, the magnetic field generating unit 200 is operated to generate a magnetic field area in a body of the patient 'B' under the control of the radiation amount control unit 500.

Next, under the control of the radiation amount control unit 500, the radiation generating unit 100 is operated to irradiate photon beam radiation towards the tumor 'T' of the patient 'B'.

At this time, while the photon beam radiation generated from the radiation generating unit 100 passes through the body of the patient 'B', charged particles (i.e., electrons) are emitted. The emitted electrons deliver high energy of photon beam radiation.

In the meantime, the emitted electrons pass through the magnetic field area formed in the body by the magnetic field generating unit 200. At this time, the emitted electrons are forced by the magnetic field (e.g., Lorentz's Force) to deflect or disperse within the magnetic field area.

That is, as shown in FIG. 5, assuming that the photon beam radiation is irradiated from the radiation generating unit 100 positioned on the left to the tumor 'T' positioned on the right, and the magnetic field operates in an entry direction of the ground, electrons are emitted while photons generated from the radiation generating unit 100 located on the left pass through the body of the patient and the emitted electrons, together with the photons, move to the tumor 'T', which is a target, through the magnetic field area in the irradiation direction of the photon beam radiation.

At this time, while the emitted electrons pass through the magnetic field area, the magnetic field direction, intensity and phase of the magnetic field generating unit 200 may be adjusted under the control of the radiation amount control unit 500 according to the calculation of the calculating unit. For example, when the magnetic field is a pulse wave in a form of a sine wave, the radiation amount control unit 500 may change the phase of the magnetic field and may match a section having the desired reference intensity or higher in the sine wave with a section in which secondary electrons are generated by photon beam radiation. As a result, some electrons are deflected to one side by Lorentz force, and the amount of electrons corresponding to the appropriate radiation amount is delivered to the tumor 'T', which is the target, through a mucous membrane M. Accordingly, the tumor 'T' is irradiated with an appropriate amount of radiation.

That is, when some of the electrons emitted by photon beam radiation are deflected or dispersed into an empty space area (e.g., body cavity, etc.) inside an organ as the direction, intensity, and phase of the magnetic field in the magnetic field generating unit 200 are adjusted through the radiation amount control unit 500 through the calculation of the calculating unit, as shown in FIG. 5, electrons are minimally delivered to the mucous membrane of an organ located in front of the tumor 'T'.

As such, the amount of radiation delivered to normal tissue is minimized, and an appropriate amount of radiation is delivered to the tumor 'T' of the patient 'B', thereby reducing the side effects of radiation and improving the therapeutic effect.

In the meantime, electrons that reach the tumor 'T', which is the target, through the magnetic field area and the mucous membrane disrupt tumor cells of the tumor 'T', thereby inhibiting the growth of tumor cells or necrosing the tumor cells. Accordingly, the tumor 'T' may be treated.

Figure 6A:
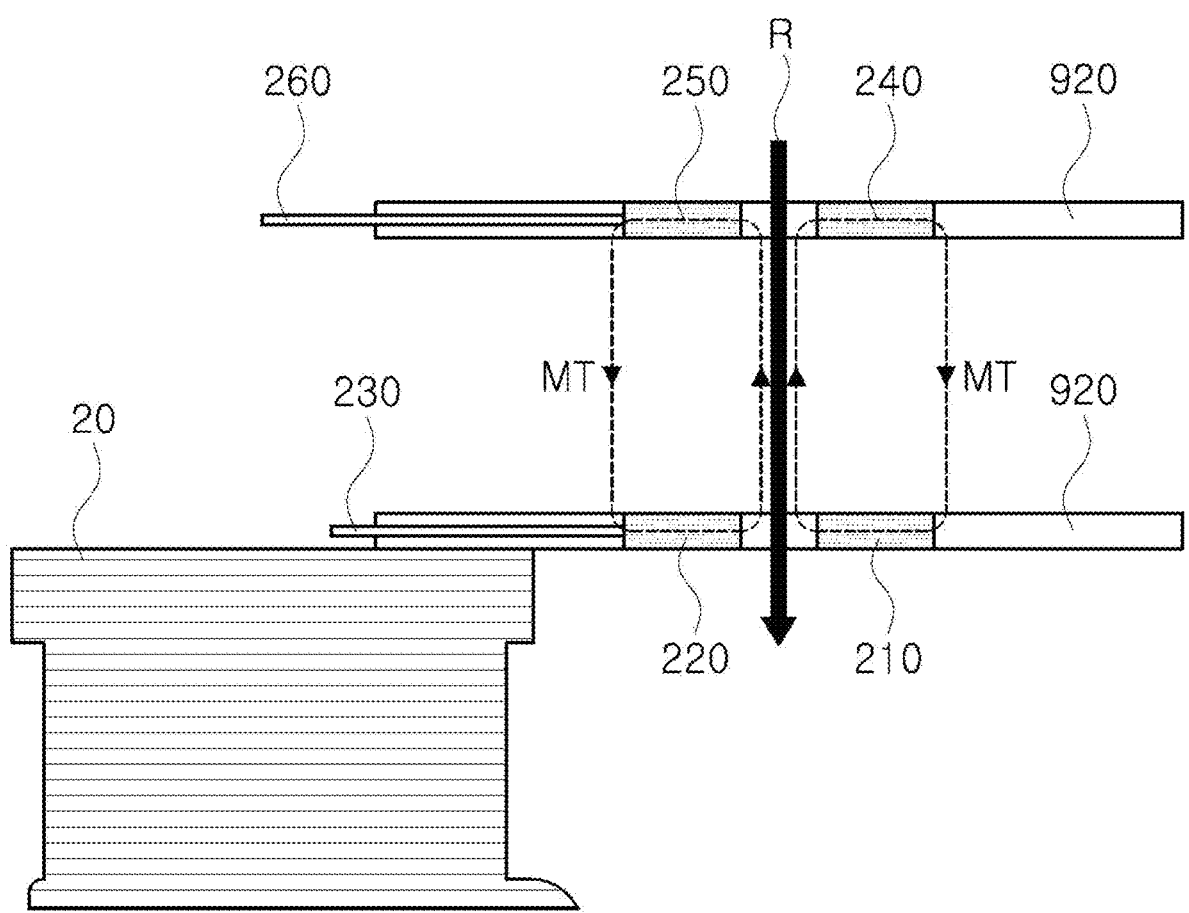
FIGS. 6A to 6D are cross-sectional views schematically illustrating a magnetic field distribution of a magnetic field generating apparatus, according to another embodiment of the inventive concept.
Figure 6B:
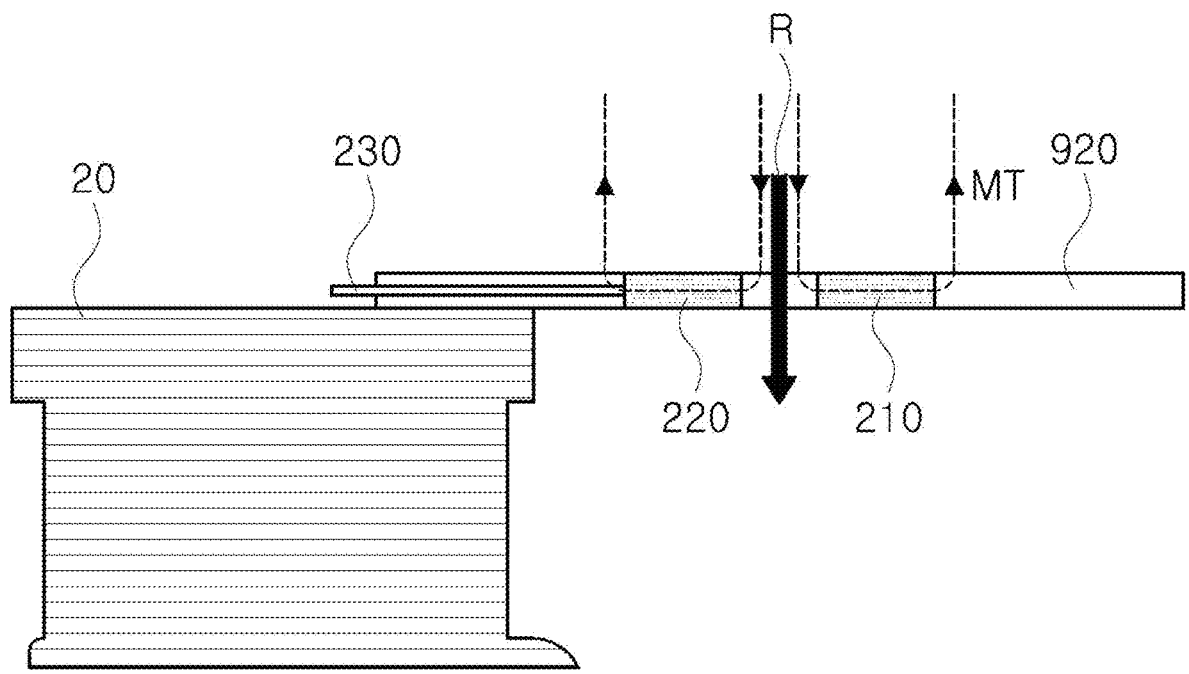
Figure 6C:
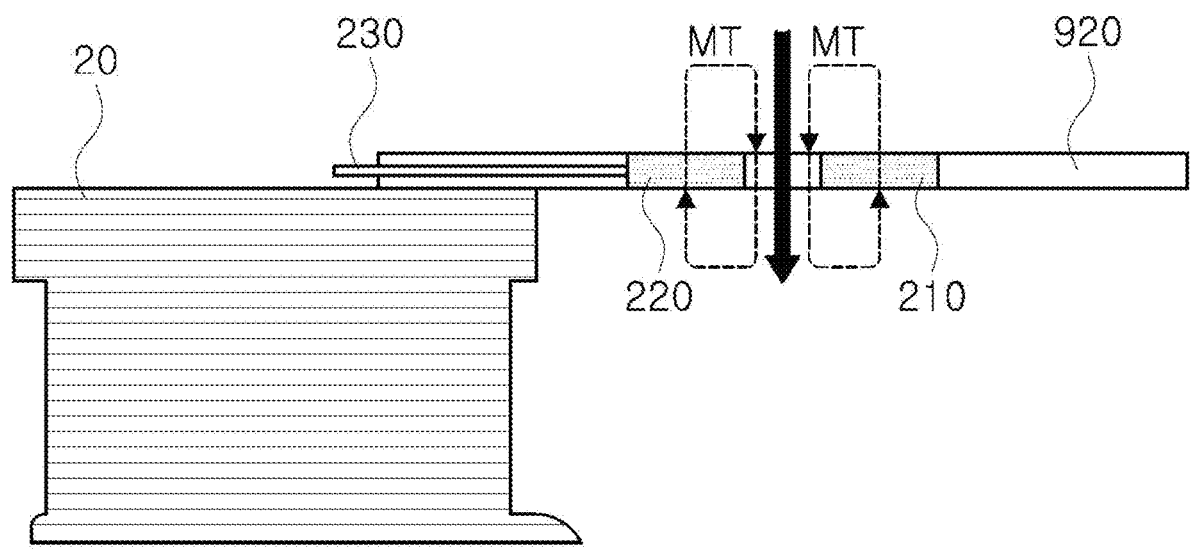
Figure 6D:
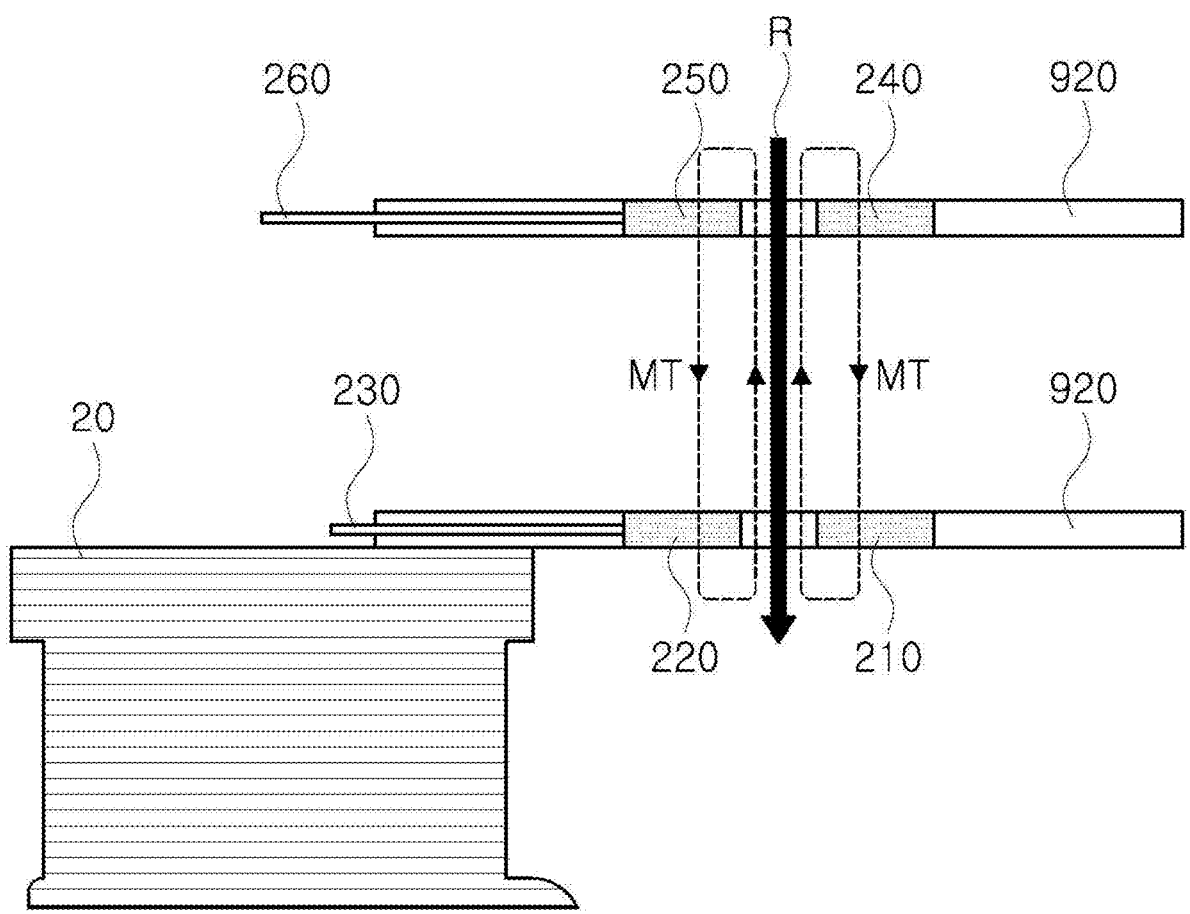
Figure 7:
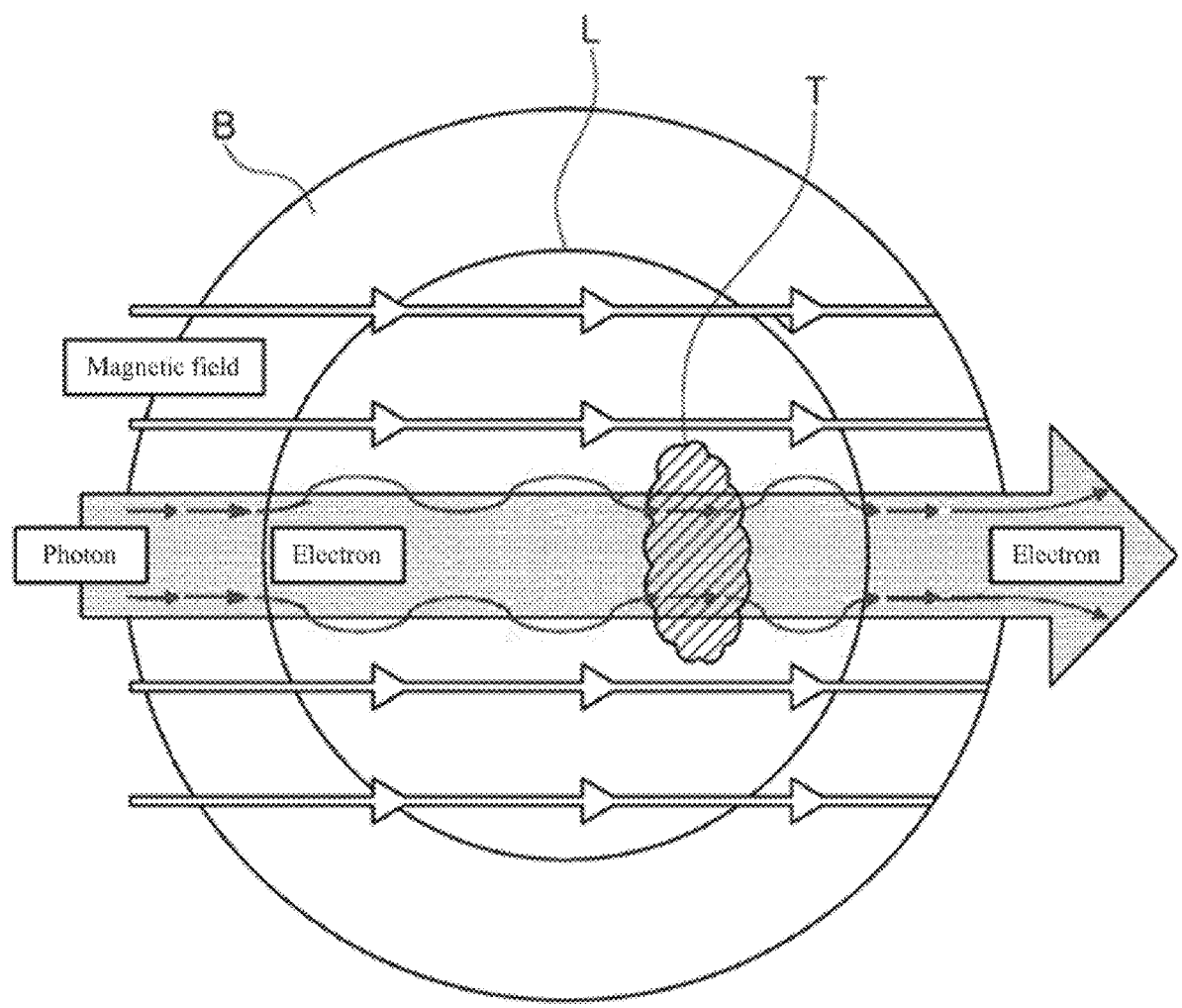
FIG. 7 is a schematic conceptual diagram for describing an operating relationship between charged particles (e.g., electrons) and a magnetic field according to radiation irradiation in a radiation treatment device using a magnetic field of FIGS. 6A to 6D.

FIGS. 6A to 6D and 7 relate to an example in which a magnetic field is generated in a direction horizontal to the radiation irradiation direction. FIGS. 6A to 6D are cross-sectional views schematically illustrating a magnetic field distribution of a magnetic field generating apparatus, according to another embodiment of the inventive concept. FIG. 7 is a schematic conceptual diagram for describing an operating relationship between charged particles (e.g., electrons) and a magnetic field according to radiation irradiation in a radiation treatment device using a magnetic field of FIGS. 6A to 6D. A description the same as the description of FIGS. 3 and 4 will be omitted to avoid redundancy.

In the meantime, an example of generating a magnetic field in a direction horizontal to an irradiation direction of photon beam radiation may be an embodiment of increasing secondary electrons provided to tumor by suppressing the dispersion of the secondary electrons in a low-density space and reducing secondary electrons reaching surrounding normal tissue as a magnetic field is formed inside the low-density space (e.g., lung, oral cavity, nasal cavity, and airway) during the treatment of tumors located in the low-density space.

Referring to FIGS. 6A to 6D, the radiation generating unit 100 of the radiation treatment device may be mounted in a structure disposed outside of a bore (not shown) having a hollow shape to irradiate photon beam radiation toward a portion of the tumor 'T' of the patient 'B' located within the bore.

Here, the radiation generating unit 100 of the radiation treatment device 10 corresponds to the charged particle or all radiation (electrons, protons, neutrons, heavy particles, etc.) related to the charged particle in addition to the linear accelerator (LINAC) that generates MV X-rays. In particular, kinetic energy is delivered to secondary electrons (hereinafter referred to as 'electrons') through a reaction by Compton effect on a surface of a material exposed due to the nature of the generated X-ray beam of an MV area, and the amount of radiation is delivered to the body by the electrons.

The magnetic field generating unit 200 of the magnetic field generating apparatus may be mounted in another shielding structure positioned outside the bore to form a magnetic field area in the body of the patient 'B'. The magnetic field generating units 200 are arranged to be opposite to each other with a bore therebetween and are located between the radiation generating unit 100 and a portion of the tumor 'T' of the patient 'B'. The magnetic field generating unit 200 forms a magnetic field parallel to the radiation beam irradiated toward a portion of the tumor 'T'.

In the meantime, in the magnetic field generating unit 200 of the magnetic field generating apparatus, a magnetic field parallel to the radiation beam irradiated to a portion of the tumor 'T' of the patient 'B' may be generated, and a plurality of magnets may be positioned opposite to each other with respect to a radiation beam so as to face each other with the same polarity. The magnets may have specific lengths.

Moreover, in another embodiment, in the magnetic field generating unit 200, a magnetic field parallel to the radiation beam irradiated to a portion of the tumor 'T' of the patient 'B' may be generated, and a plurality of magnets may be positioned opposite to each other with respect to the radiation beam so as to face each other with the same polarity. Lengths of the magnets may be provided to extend to the surface of the tumor 'T'. When a plurality of magnets of the magnetic field generating unit 200 are positioned opposite to each other with respect to the radiation beam such that the same polarity faces each other, the magnets having various lengths may be provided.

Furthermore, in another embodiment, in the magnetic field generating unit 200, a magnetic field parallel to the radiation beam irradiated to the portion of the tumor 'T' of the patient 'B' may be generated in a form of a Helmholtz coil, and a plurality of magnets, in which a coil is wound, surround the circumference of the radiation beam such that opposite polarities face each other, and may be spaced from each other in the radiation direction of the radiation beam.

Besides, in another embodiment, in the magnetic field generating unit 200, a magnetic field parallel to the radiation beam irradiated to the portion of the tumor 'T' of the patient 'B' may be generated according to Ampere's law, and a plurality of main magnets may be positioned opposite to each other with respect to the radiation beam so as to face each other with the same polarity. An auxiliary magnet may be positioned on one side of the main magnet such that a magnetic field is formed to the outside with respect to the irradiation direction of the radiation beam, and an auxiliary magnet may be positioned on the other side of the main magnet such that a magnetic field is formed to the inside with respect to the irradiation direction of the radiation beam.

As described above, as the magnets of the magnetic field generating unit 200 are placed, the emitted electrons make a helical motion by a magnetic field formed parallel to the radiation beam while passing through a magnetic field area, and do not deflect or disperse. In addition, the emitted electrons travel with the radiation beam.

Here, the magnetic field generating unit 200 forms a magnetic field area in an area (more preferably, an empty space (body cavity) in the body or a portion (lung) having low density) in the body of the patient 'B' between the radiation generating unit 100 and the tumor 'T' portion of the patient 'B'. In addition, the magnetic field generating unit 200 may form a homogeneous or non-homogeneous magnetic field area in whole or in part of the radiation beam trajectory. In addition, the magnetic field generating unit 200 may include an electromagnet, a permanent magnet, or a combination thereof.

In the meantime, to increase the degree of freedom in a direction of the magnetic field, a pair of magnets that are the magnetic field generating unit 200 may rotate along an outer perimeter of the bore (e.g., the patient 'B' located within the bore), but not limited thereto. For example, the magnetic field generating unit 200 may form a magnetic field area by using a magnet selected from among a plurality of magnets through the control of the radiation amount control unit 500 while the plurality of magnets are fixedly positioned along the outer perimeter of the bore (e.g., the perimeter of the patient 'B').

The magnetic field generating apparatus may include the two plate-shaped frames 920 facing each other. The structure of each of the plate-shaped frames 920 is the same as that of the plate-shaped frame 900 of FIGS. 3 and 4, and thus a description thereof will be omitted to avoid redundancy.

In an embodiment, the two plate-shaped frames 920 may be arranged to face each other. Here, a separate vertical frame connecting the two plate-shaped frames 920 may be placed in the structure facing each other. Besides, it may be variously modified, and may be configured as a circular frame.

In an embodiment, the magnetic field generating unit 200 may include a magnetic field generating material, which is arranged in a left-right symmetrical structure with respect to an axis to which the photon beam radiation is irradiated, and may generate a magnetic field MT as shown in FIGS. 6A to 6D.

For example, in FIG. 6A, as the two N-pole electromagnets 240 and 250 are placed on the upper plate-shaped frame 920, and the two S-pole electromagnets 210 and 220 are placed on the lower plate-shaped frame, the magnetic field generating units 200 may face each other to generate the magnetic field MT in a direction horizontal to the radiation irradiation direction 'R'. Here, as shown in FIG. 6A, the magnetic field generating unit 200 may form two effective areas between the upper and lower the plate-shaped frames 920, which have an area size the same as the area size of the electromagnets 210, 220, 240, and 250.

Moreover, for example, as illustrated in FIG. 6B, the two electromagnets 210 and 220 having the same polarity are placed, and thus the magnetic field generating unit 200 may generate the magnetic field MT in a direction horizontal to the radiation irradiation direction 'R'. The magnetic field generating unit 200 may form the two effective areas above only the plate-shaped frame 920 as shown in FIG. 6B while the area size of the two effective areas is greater than an area size in which the electromagnets 210 and 220 are disposed.

Moreover, for example, as illustrated in FIG. 6C, the two electromagnets 210 and 220 having the same polarity are placed, and thus the magnetic field generating unit 200 may generate the magnetic field MT in a direction horizontal to the radiation irradiation direction 'R'. The magnetic field generating unit 200 may form the two effective areas above and below the plate-shaped frame 920 as shown in FIG. 6C while the area size of the two effective areas is smaller than an area size in which the electromagnets 210 and 220 are disposed.

Moreover, for example, in FIG. 6D, as the two N-pole electromagnets 240 and 250 are placed on the upper plate-shaped frame 920, and the two S-pole electromagnets 210 and 220 are placed on the lower plate-shaped frame, the magnetic field generating units 200 may face each other to generate the magnetic field MT in a direction horizontal to the radiation irradiation direction 'R'. Here, as shown in FIG. 6D, the magnetic field generating unit 200 may form two effective areas between the upper and lower the plate-shaped frames 920, which have an area size smaller than the area size of the electromagnets 210, 220, 240, and 250.

In an embodiment, the radiation amount control unit 500 of the radiation treatment device controls the tumor surface dose delivered to a portion of the tumor 'T' of the patient 'B' from the radiation generating unit 100 by adjusting the intensity, direction, phase, and effective area of the magnetic field of the magnetic field generating unit 200 such that the tumor surface dose is concentrated and enhanced in the portion of the tumor 'T' of the patient 'B'. While rotating the magnetic field generating unit 200 to the desired location along the circumference of the patient 'B'. The radiation amount control unit 500 may adjust the intensity, direction, phase, and effective area of the magnetic field.

In an embodiment, the radiation amount control unit 500 may further include a calculating unit (not shown) that controls an operation of the radiation generating unit 100 and calculates the tumor surface dose delivered to the tumor 'T'.

In an embodiment, the calculating unit may calculate the tumor surface dose delivered to the tumor 'T' of the patient 'B' by using Equation 3 below.

$$D(x,y,z) = \iiint TERMA(x',y',z') \times Kernel(x,x',y,y',z,z') \, dx'dy'dz'$$ [Equation 3]

Here, D(x,y,z) denotes a value of the tumor surface dose absorbed at a specific location (x,y,z); TERMA(x', y', z') denotes the total energy of the incident radiation beam attenuated in a minute volume dx'dy'dz'; and, Kernel(x, x', y, y', z, z') denotes a rate of dose absorbed at a specific location (x,y,z) by unit energy attenuated in the minute volume dx'dy'dz'. At this time, a kernel that considering a magnetic field formed by the magnetic field generating unit 200 is used.

Accordingly, when the TERMA value and the Kernel value are convolved with respect to the whole volume, a value of the absorbed tumor surface dose at a specific location (x,y,z) may be calculated.

In the meantime, the TERMA value indicates the total attenuated energy of uncharged x-rays, and thus it is not related to the magnetic field.

Moreover, because the Kernel value indicates a spatial dose distribution by electrons mainly generated during an attenuation process, the Kernel value is absolutely influenced by the magnetic field. In general, when the kernel is obtained, it is obtained through computational simulation. A new kernel is obtained by implementing a spatially constant magnetic field in a computer simulation program, and the Kernel Deform map is configured as follows. This is modeled and applied as in Equation 4 below.

$$Kernel_{new}(B,x,x',y,y',z,z') = Deform\_map(Kernel(x,x',y,y',z,z'),B)$$ [Equation 4]

Accordingly, the calculating unit calculates the intensity, direction phase, and magnitude of the magnetic field for optimizing the distribution of a radiation amount.

Meanwhile, in another embodiment, the calculating unit may be calculated by a Full Monte Carlo simulation method.

In other words, the calculating unit may use a toolkit capable of simulating a magnetic field, may construct a history by using the probabilistic Monte Carlo method for each particle, may calculate the overall dose distribution by adding the spatial influence of each dose in the histories, and may calculate the absorbed radiation amount value at a specific location.

Accordingly, the radiation amount control unit 500 may plan the tumor surface dose and then may calculate the intensity and distribution of a magnetic field according to the planned tumor surface dose through the calculating unit.

Referring to FIG. 7, according to the configuration, a process of radiation treatment of a portion of the tumor 'T' of the patient 'B' by using the affected tissue treatment device 10 according to an embodiment of the inventive concept will be described as follows.

Prior to descriptions, hereinafter, according to an embodiment, as shown in FIG. 7, when radiation is irradiated from the left side of FIG. 7 to the portion of the tumor 'T' positioned on the right side of FIG. 7, a magnetic field operates in a direction parallel to the radiation beam, and an organ (lung, oral cavity, airway, etc.) having a small internal density is placed between the radiation generating unit 100 and the portion of the tumor 'T', enhancing the treatment of a surface portion of the tumor 'T' will be described.

First of all, while the patient who has the portion of the tumor 'T' to be treated, lies on the plate-shaped frame 920, the magnetic field generating unit 200 is operated to generate a magnetic field area in a body of the patient 'B' under the control of the radiation amount control unit 500.

Next, under the control of the radiation amount control unit 500, the radiation generating unit 100 is operated to irradiate radiation towards the portion of the tumor 'T' of the patient 'B'.

At this time, while the radiation generated from the radiation generating unit 100 passes through the body of the patient charged particles (i.e., electrons) are emitted. The emitted electrons deliver high energy of radiation. Here, the magnetic field area formation and radiation irradiation may be performed at the same time.

In the meantime, the emitted electrons pass through the magnetic field area formed in a body by the magnetic field generating unit 200. While passing through the magnetic field area, the emitted electrons make a helical motion by a magnetic field formed parallel to the radiation beam, and thus the emitted electrons do not deflect or disperse. In addition, the emitted electrons move to the portion of the tumor 'T', which is the target.

In more detail, while being spirally moved by the force of a magnetic field, the emitted electrons move in the irradiation direction of the radiation beam and then reaches a portion of the tumor 'T' being the target.

That is, as shown in FIG. 7, assuming that the radiation is irradiated from the radiation generating unit 100 positioned on the left to a portion of the tumor 'T' positioned on the right, and the magnetic field operates parallel to the irradiation direction of the radiation beam, electrons are emitted while radiation photons generated from the radiation generating unit 100 located on the left pass through the body of the patient 'B', and the emitted electrons, together with the photons, move to the portion of the tumor 'T', which is a target, through the magnetic field area in the irradiation direction of the radiation.

At this time, while the emitted electrons pass through the magnetic field area, the intensity, phase, direction and effective area of the magnetic field of the magnetic field generating unit 200 are adjusted under the control of the radiation amount control unit 500 according to the calculation of the calculating unit. Accordingly, electrons passing through the magnetic field area move with the radiation beam, and the amount of electrons corresponding to the appropriate radiation amount is delivered to the portion of the tumor 'T' being the target through the low-density space. Accordingly, appropriate tumor surface dose is concentrated and irradiated on a surface portion of the tumor 'T'.

Moreover, as the intensity, direction, phase, and effective area of the magnetic field in the magnetic field generating unit 200 are adjusted by the radiation amount control unit 500 through the calculation unit, as shown in FIG. 7, some of the electrons emitted by radiation are not deflected or dispersed to an empty space area inside the organ, and the maximum number of electrons are delivered to the surface of the tumor 'T'.

As such, the amount of radiation delivered to the surface of the portion of the tumor 'T' of the treatment target is strengthened by preventing the divergence of radiation charged scatter particles of and concentrating the scatter particles thus charged, thereby improving the effect of radiation treatment. In addition, side effects of radiation may be reduced by reducing the use of additional radiation and damage to surrounding normal tissue due to the divergence of charged scatter particles.

In the meantime, an external leakage magnetic field may cause malfunction of the radiation treatment device 10 and may refer to a factor that interferes with the treatment. Accordingly, in addition to a method of reducing external leakage magnetic field by synchronizing a magnetic field pulse with a radiation pulse described above, a method of reducing the external leakage magnetic field by including a separate shield in the radiation treatment device 10 will be described with reference to FIG. 8. In addition, another example will be described in detail with reference to FIGS. 9 to 16 below.

Figure 8A:
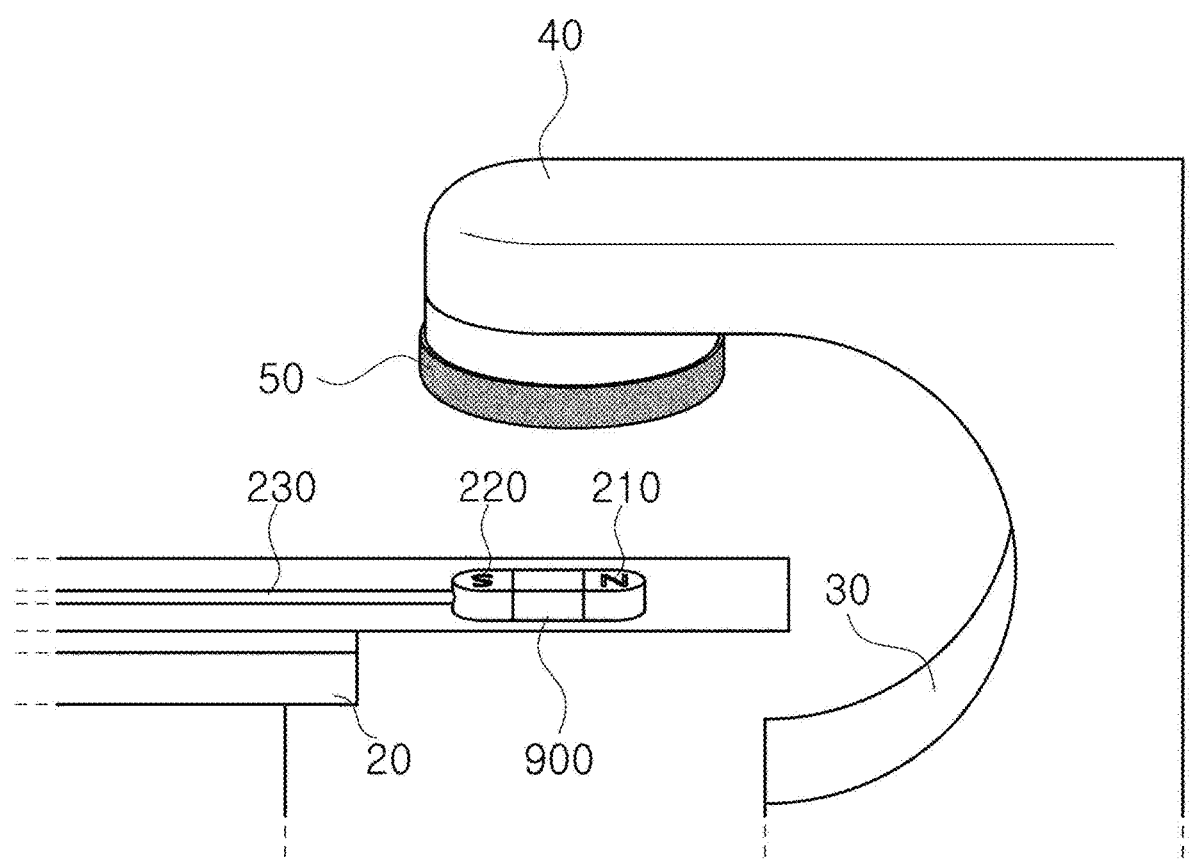
FIGS. 8A to 8C are diagrams for describing a configuration of a magnetic field shield unit, according to an embodiment of the inventive concept.
Figure 8B:
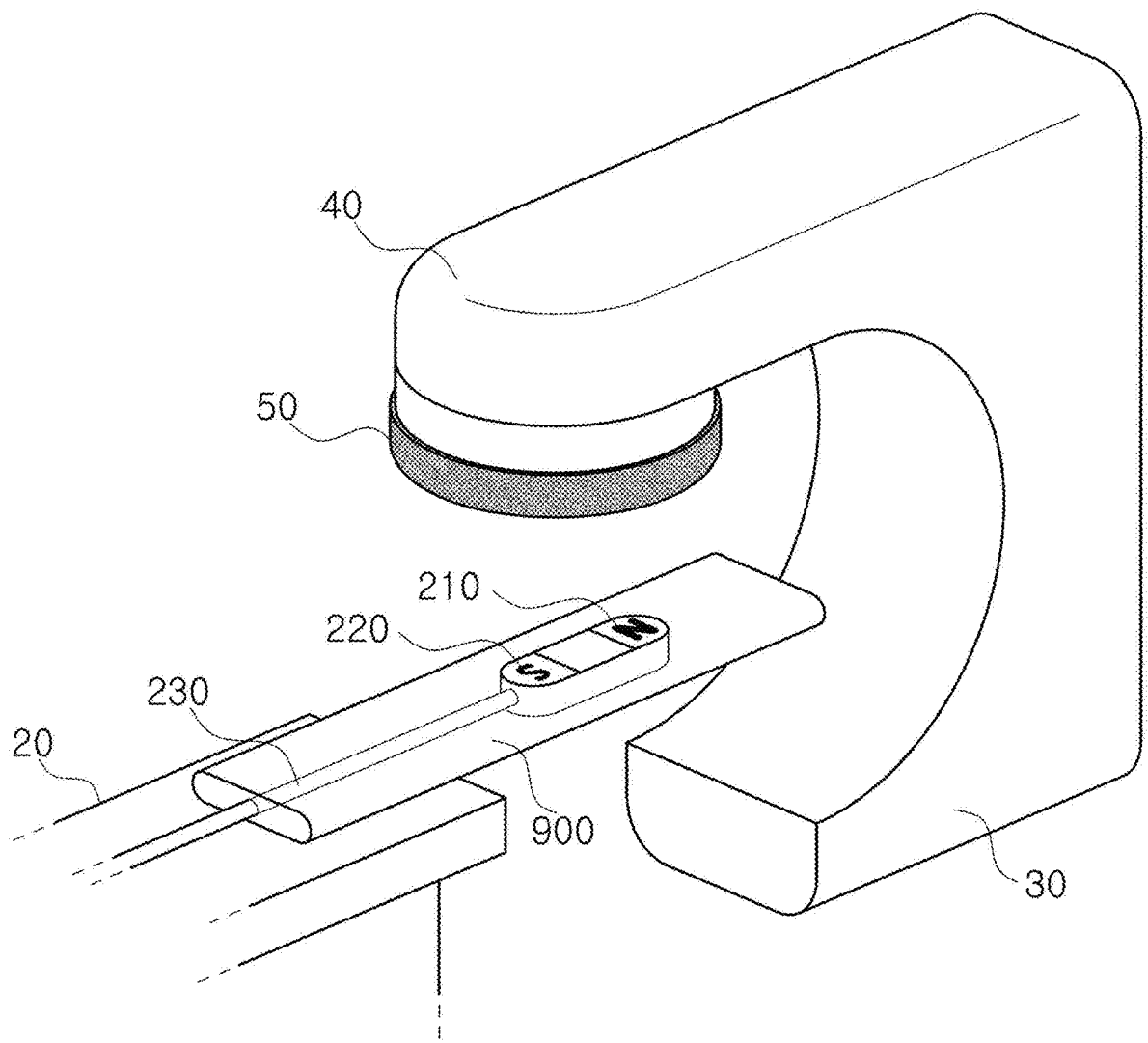
Figure 8C:
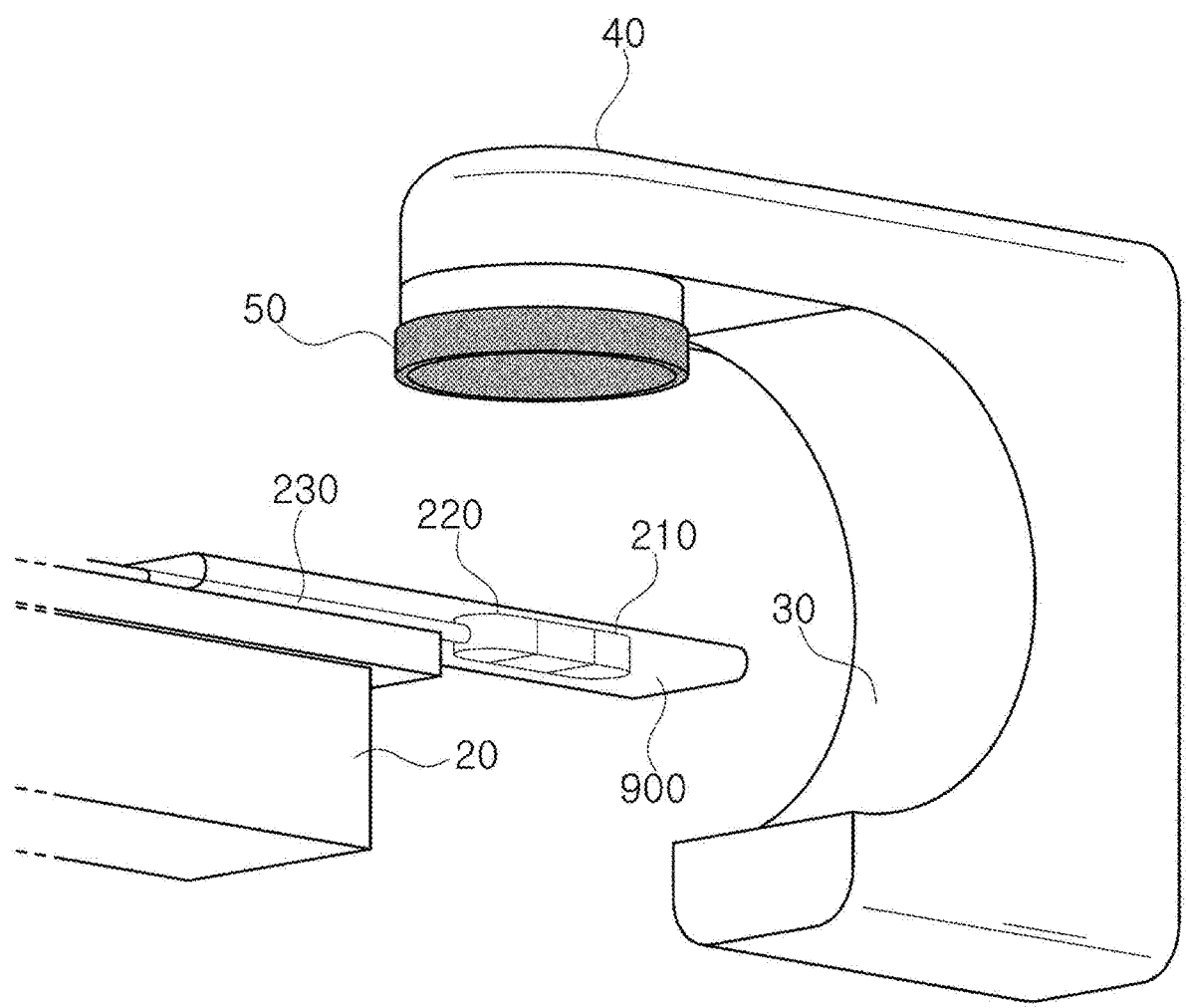

FIGS. 8A to 8C are diagrams for describing a configuration of a magnetic field shield unit, according to an embodiment of the inventive concept.

Referring to FIGS. 8A to 8C, a magnetic field shield unit 50 may be in a form of surrounding a head 40 of the radiation treatment device 10 rather than a patient space side. For example, the magnetic field shield unit 50 may be in a form of surrounding bottom and side surfaces of the head 40 of the radiation treatment device 10 like a 'finger thimble'. In addition, a shielding material constituting the magnetic field shield unit 50 may be iron or Mu-metal.

On the other hand, in the radiation treatment device 10 according to an embodiment of the inventive concept described in FIGS. 9 to 16, operations of the synchronization control unit 700 and the radiation amount control unit 500 described in FIG. 1 may be naturally added.

Nowadays, while minimizing radiation irradiation to normal tissue, the radiation treatment device 10 may adopt a multi-leaf collimator (MLC) to intensively treat only tumor tissue. This multi-leaf collimator is driven by using a motor, and the radiation treatment device 10 needs to suppress the magnetic field in the motor to a maximum of 600 Gauss (G) or less.

Figure 9:
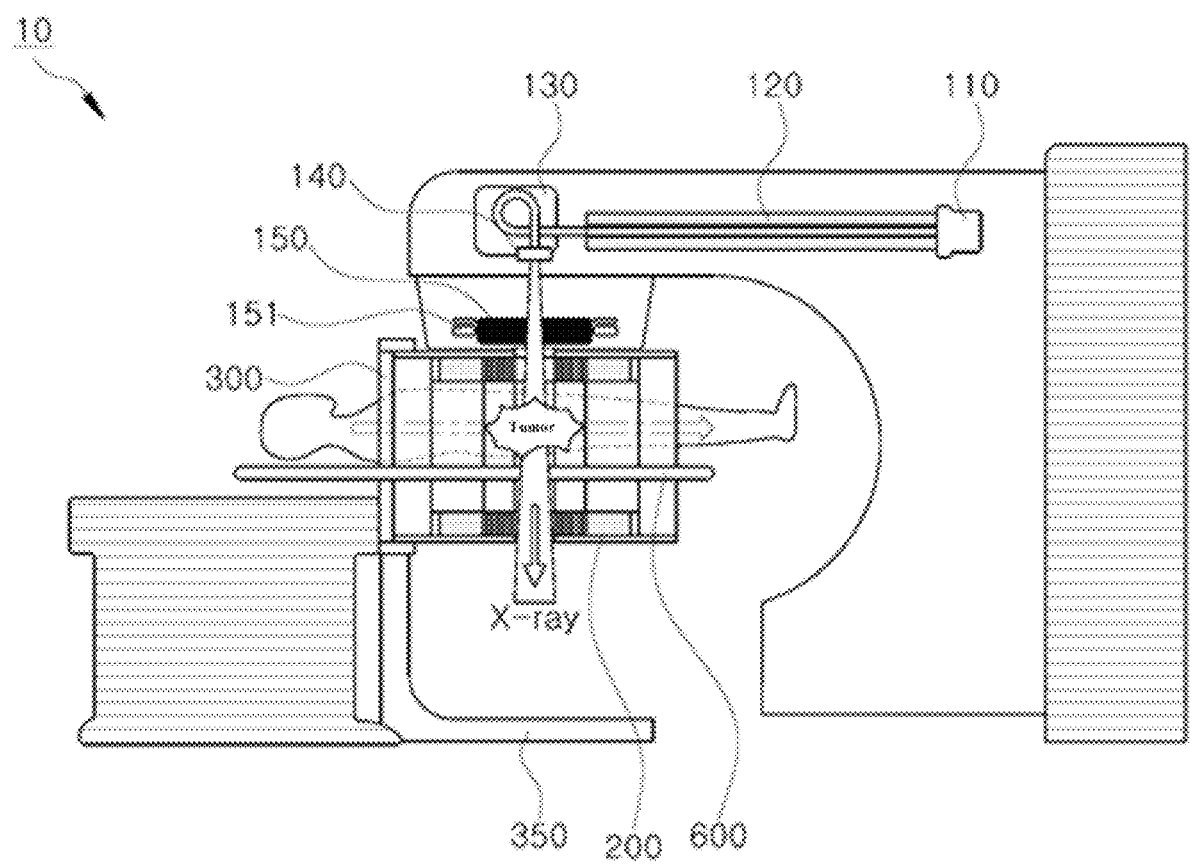
FIGS. 9 and 10 are block diagrams of a radiation treatment device, according to another embodiment of the inventive concept.
Figure 10:
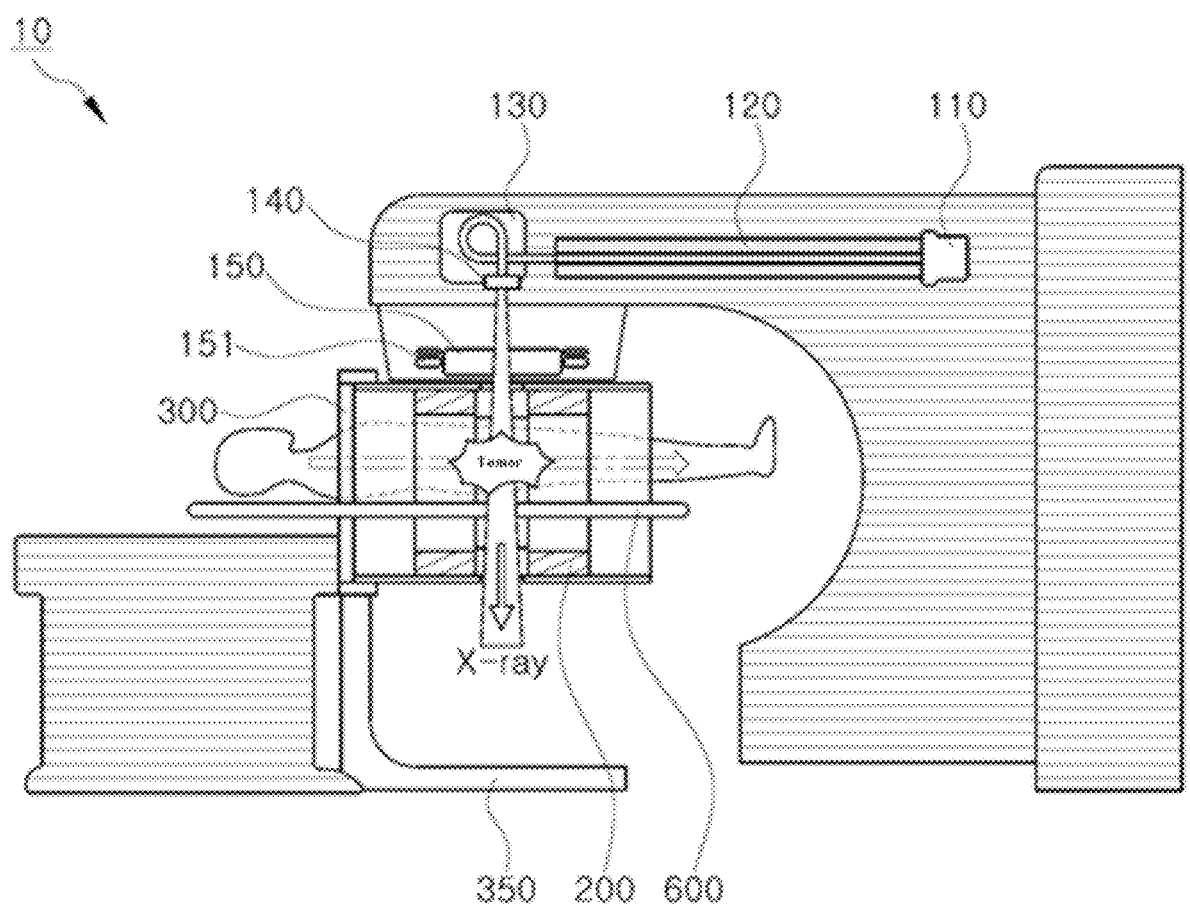

FIGS. 9 and 10 illustrate a specific configuration of the radiation treatment device 10, according to an embodiment of the inventive concept.

At this time, FIG. 9 illustrates that an electromagnet is used as the magnetic field generating unit 200, and FIG. 10 illustrates that a permanent magnet is used as the magnetic field generating unit 200.

Hereinafter, the radiation treatment device 10 according to an embodiment of the inventive concept will be described for each component in detail with reference to FIGS. 9 and 10.

First of all, the radiation generating unit 100 irradiates radiation to affected tissue (e.g., tumor portion) of a subject (e.g., a patient).

In more detail, as illustrated in FIGS. 9 and 10, the radiation generating unit 100 may include an electron gun 110 that generates an electron beam, a linear accelerator 120 that accelerates the electron beam generated by the electron gun 110, a bending magnet 130 that turns a direction of the accelerated electron beam, a target 140 that generates radiation such as X-rays when electron beams collide with each other, and a multi-leaf collimator MLC 150 that restricts an area to which radiation generated by the target 140 is irradiated. Accordingly, the radiation treatment device 10 according to another embodiment of the inventive concept may perform treatment by irradiating the radiation generated by the radiation generating unit 100 to the affected tissue of the subject, such as a patient.

However, in the case where there is a radiation-sensitive portion in a trajectory to which the radiation is irradiated, side effects occur when a specific radiation amount or more is delivered. In particular, because sufficient therapeutic radiation dose is incapable of being delivered to tumor tissue when radiation-sensitive normal tissue is close to tumor tissue, the therapeutic effect is inevitably lowered. Accordingly, during radiation treatment, radiation sufficiently irradiates the tumor to be destroyed, and the amount of radiation needs to be controlled to minimize damage to the normal tissue surrounding the tumor.

Accordingly, as illustrated in FIGS. 9 and 10, the radiation treatment device 10 according to an embodiment of the inventive concept may include the magnetic field generating unit 200 that forms a magnetic field on the affected tissue. The radiation treatment device 10 may reduce the radiation dose to normal tissue by controlling charged particles (e.g., electrons) capable of being generated in the affected tissue by radiation such that the magnetic field generating unit 200 forms a magnetic field in a second direction perpendicular to a first direction to which the radiation is irradiated.

In more detail, as illustrated in FIGS. 9 and 10, the magnetic field generating unit 200 may include a plurality of electromagnets (see FIG. 9) or permanent magnets (see FIG. 10), which are arranged to form a left-right symmetrical structure on the basis of an axis to which radiation is irradiated.

However, when the magnetic field generating unit 200 is used in the radiation treatment device 10 according to an embodiment of the inventive concept, the generated magnetic field may affect the radiation generating unit 100 and the like, thereby causing malfunction.

In detail, the multi-leaf collimator 150 of the magnetic field generating unit 200 includes a motor 151 to operate the multi-leaf in a form of an opening to which radiation is irradiated. In the case of the motor 151, a malfunction or inability to operate may be caused by a magnetic field leaking to the outside. In particular, when a location is changed because a multi-leaf is operated incorrectly, a dangerous situation where a large amount of radiation is irradiated to normal tissue may be caused. It is desirable to maintain an external magnetic field such that the external magnetic field is capable of being adjusted to be less than or equal to 600 G to secure a normal operation of the motor 151 of the multi-leaf collimator 150.

Moreover, while a path of an electron beam is distorted by the external magnetic field in the electron gun 110 and the linear accelerator 120 in addition to the motor 151, there may be a difference in radiation dose. Furthermore, while beam targeting becomes difficult, accurate radiation irradiation and treatment may become difficult.

Accordingly, as illustrated in FIGS. 9 and 10, the radiation treatment device 10 according to an embodiment of the inventive concept includes a magnetic field shield unit 300 that attenuates a magnetic field leakage to the outer area by placing the magnetic field generating unit 200 in an inner area. Accordingly, the magnetic field generated from the magnetic field generating unit 200 may affect the radiation generating unit 100 to prevent malfunctions.

In this case, the magnetic field shield unit 300 may be preferably configured in a cylindrical shape made of a magnetic material such as iron or Mu-metal. Accordingly, the magnetic field shield unit 300 may form a loop-shaped magnetic circuit structure with respect to the magnetic field formed from the magnetic field generating unit 200 and may attenuate the magnetic field leaking to the external area.

FIGS. 11A to 11C and 12A to 12C illustrate a magnetic field distribution in an outer area of the radiation treatment device 10, according to an embodiment of the inventive concept.

Figure 11A:
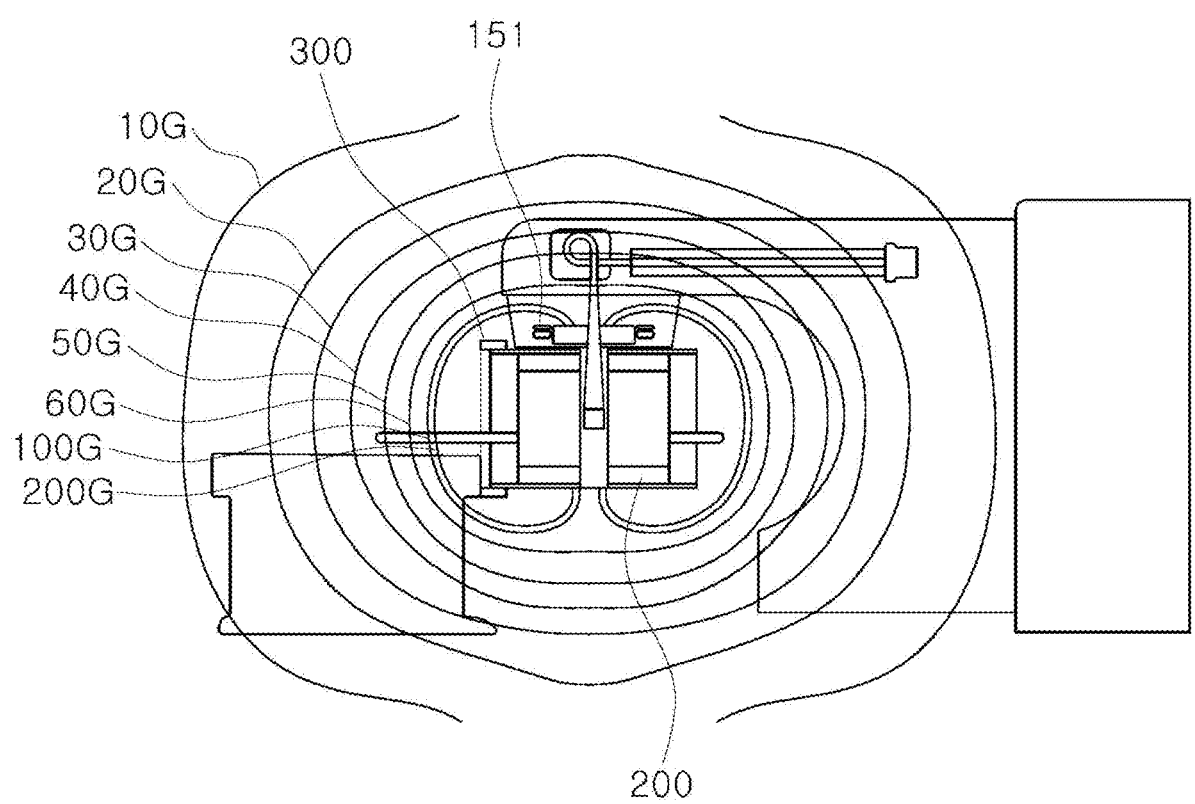
FIGS. 11A to 11C and 12A to 12C illustrate a magnetic field distribution in an outer area of a radiation treatment device, according to another embodiment of the inventive concept.
Figure 11B:
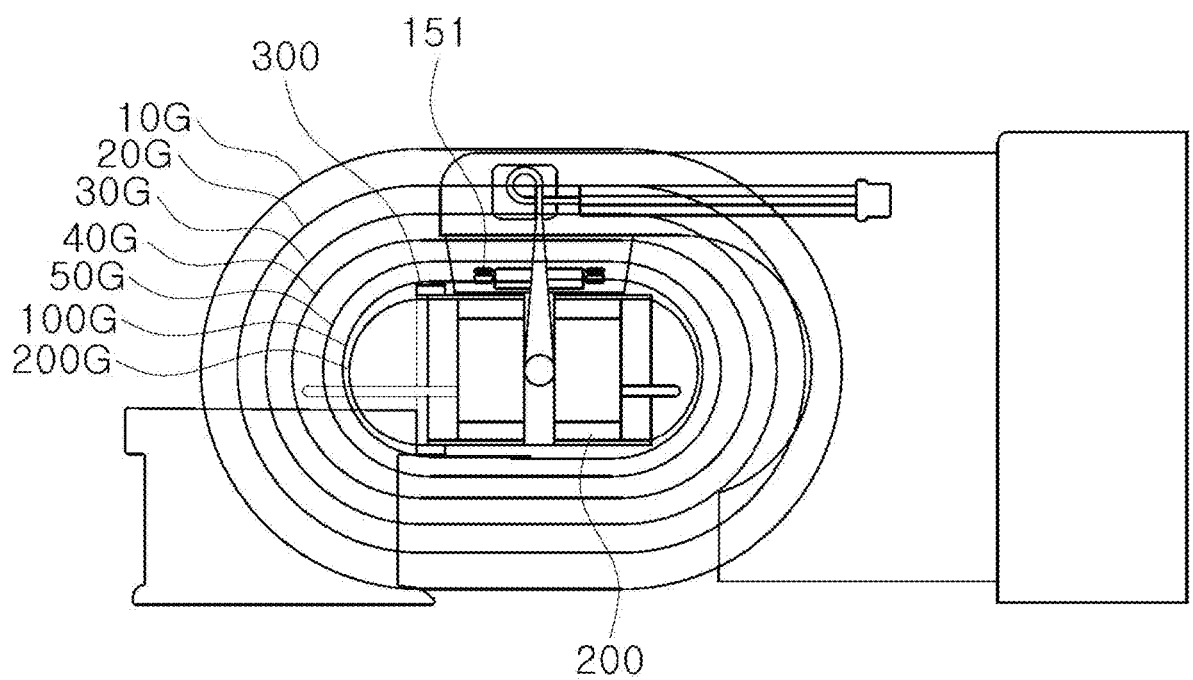
Figure 11C:
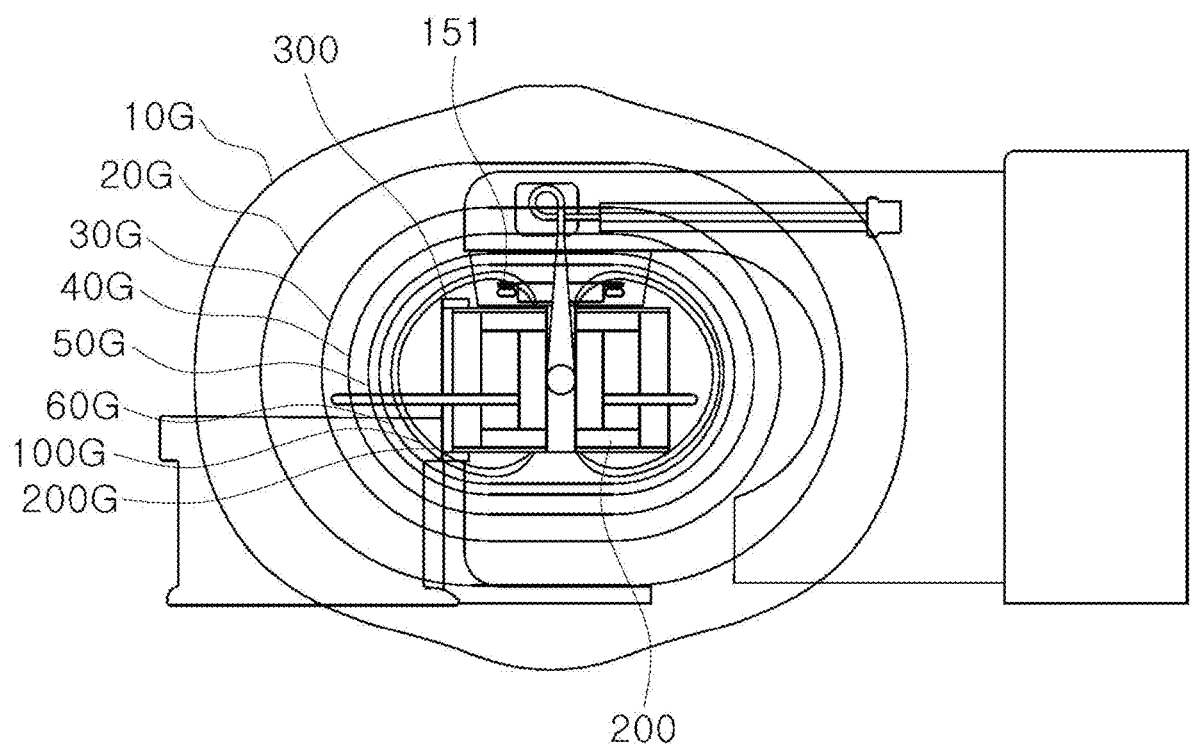

First of all, FIGS. 11A to 11C illustrates a magnetic field distribution in an outer area of the radiation treatment device 10 including the magnetic field generating unit 200 using an electromagnet.

At this time, FIG. 11A illustrates that the magnetic field shield unit 300 is not provided. As illustrated in FIG. 11A, FIG. 11A indicates that an external magnetic field intensity in the motor 151 is 500 G, which satisfies a normal operating condition (600 G or less) of the motor 151, but it is difficult to exclude the possibility of malfunction because the external magnetic field intensity is close to a threshold.

On the other hand, FIG. 11B illustrates that the magnetic field shield unit 300 is provided. As illustrated in FIG. 11B, it may be seen that the external magnetic field intensity of the motor 151 is 70 G, which sufficiently satisfies the normal operating condition of the motor 151 (600 G or less). Furthermore, it may be seen that the magnetic field at a center area corresponding to the affected tissue is also strengthened to 2320 G (2100 G in FIG. 11A).

In addition, FIG. 11C illustrates that a magnetic field focusing unit 400 is also provided together with the magnetic field shield unit 300. As illustrated in FIG. 11C, the magnetic field in the center area corresponding to the affected tissue is focused up to 2670 G by including the magnetic field focusing unit 400. At this time, it may be seen that the external magnetic field intensity in the motor 151 is also 200 G, which sufficiently satisfies the normal operating condition.

Figure 12A:
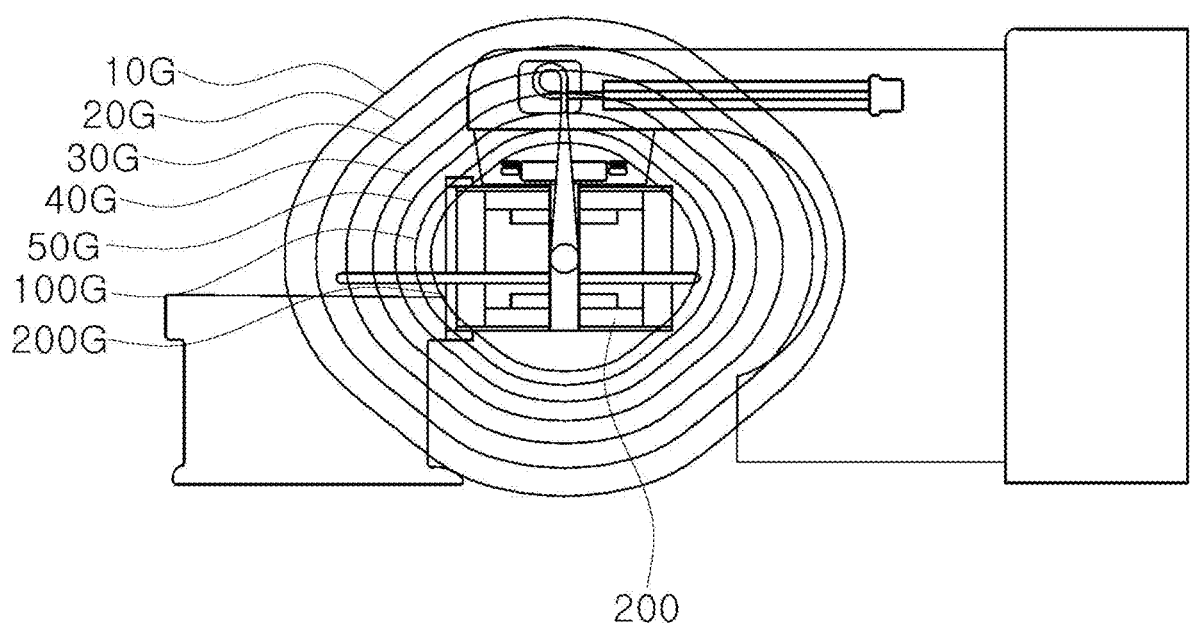
Figure 12B:
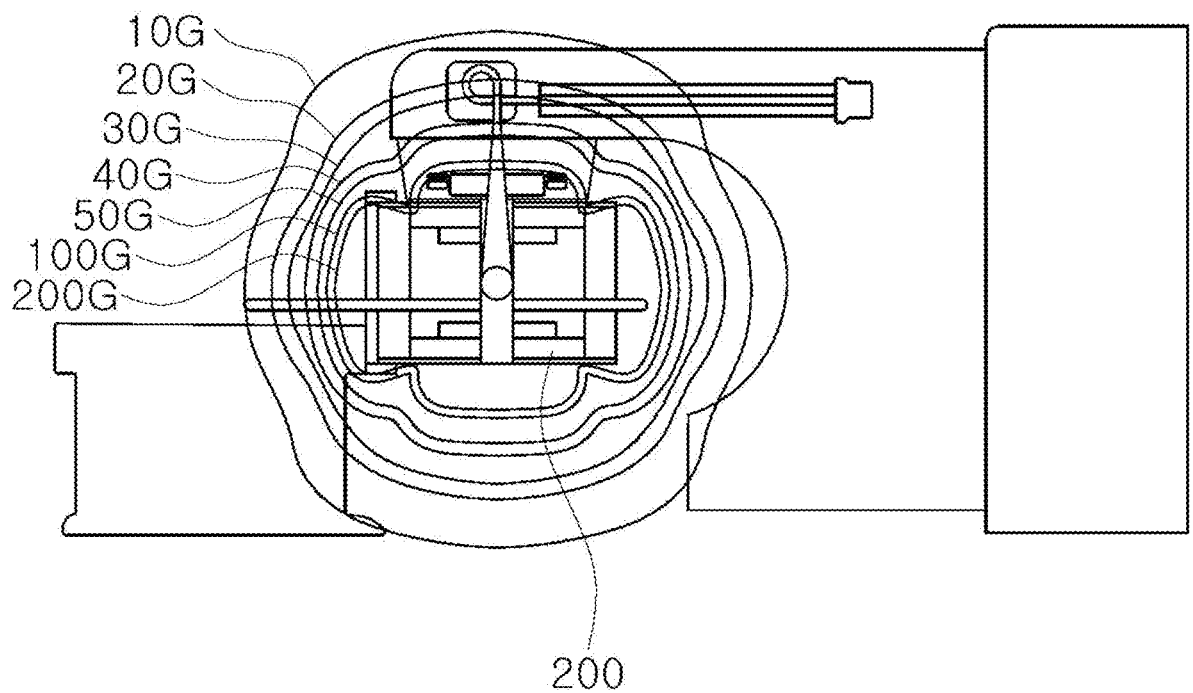
Figure 12C:
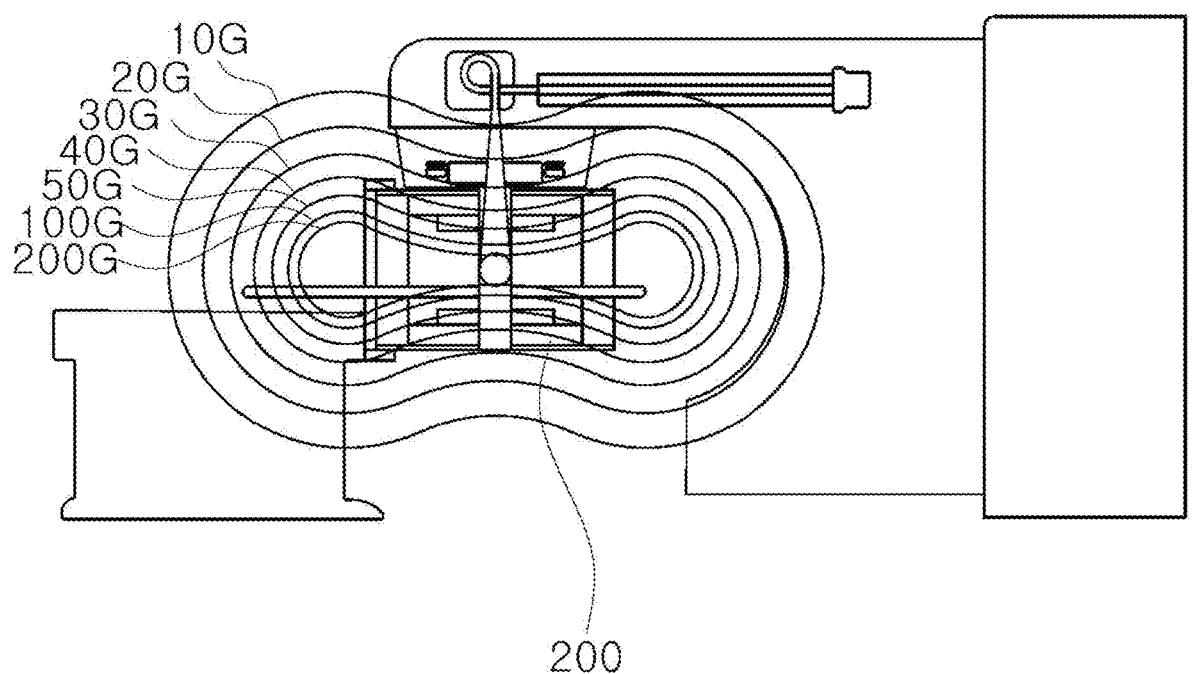

Moreover, FIGS. 12A to 12C illustrates a magnetic field distribution in an outer area of the radiation treatment device 10 including the magnetic field generating unit 200 using a permanent magnet.

First of all, FIG. 12A illustrates that the magnetic field shield unit 300 is not provided. As illustrated in FIG. 12A, it may be seen that the external magnetic field intensity of the motor 151 is 1000 G, which is out of the normal operating condition of the motor 151 (600 G or less), and thus the possibility of malfunction is very high.

On the other hand, FIG. 12B illustrates that the magnetic field shield unit 300 is provided. As illustrated in FIG. 12B, it may be seen that the external magnetic field intensity of the motor 151 is 250 G, which sufficiently satisfies the normal operating condition of the motor 151 (600 G or less). Furthermore, it may be seen that the magnetic field at a center area corresponding to the affected tissue is also strengthened to 2460 G (2090 G in FIG. 12A).

Also, FIG. 12C illustrates that a Halbach array structure is formed by providing a Halbach magnet 210 in the magnetic field generating unit 200 together with the magnetic field shield unit 300. As illustrated in FIG. 12C, it may be seen that the external magnetic field intensity in the motor 151 is capable of being further improved to 120 G while the magnetic field in the center area corresponding to the affected tissue is strengthened to 2890 G by providing the Halbach magnet 210 to the magnetic field generating unit 200 to form a Halbach array structure.

Figure 13A:
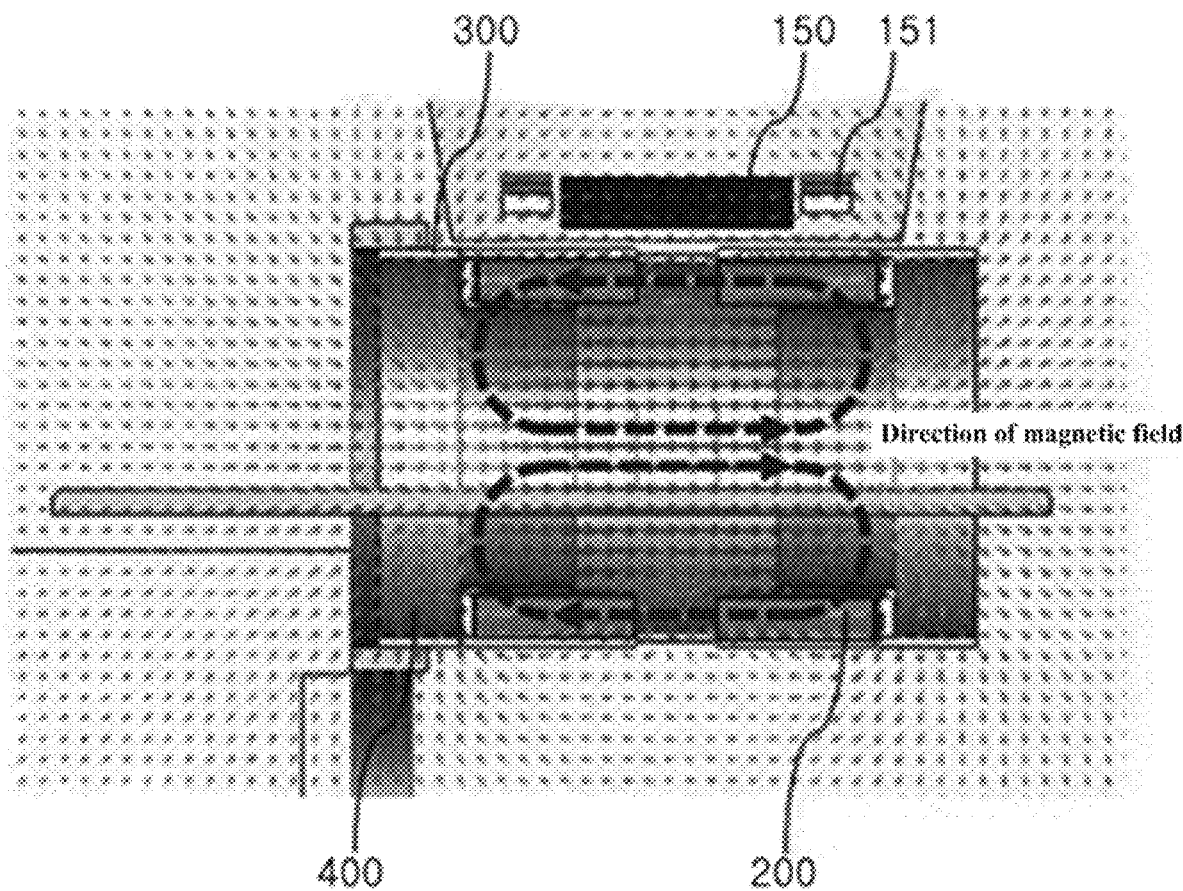
FIGS. 13A and 13B illustrate a magnetic field distribution in an inner area of a radiation treatment device, according to another embodiment of the inventive concept.
Figure 13B:
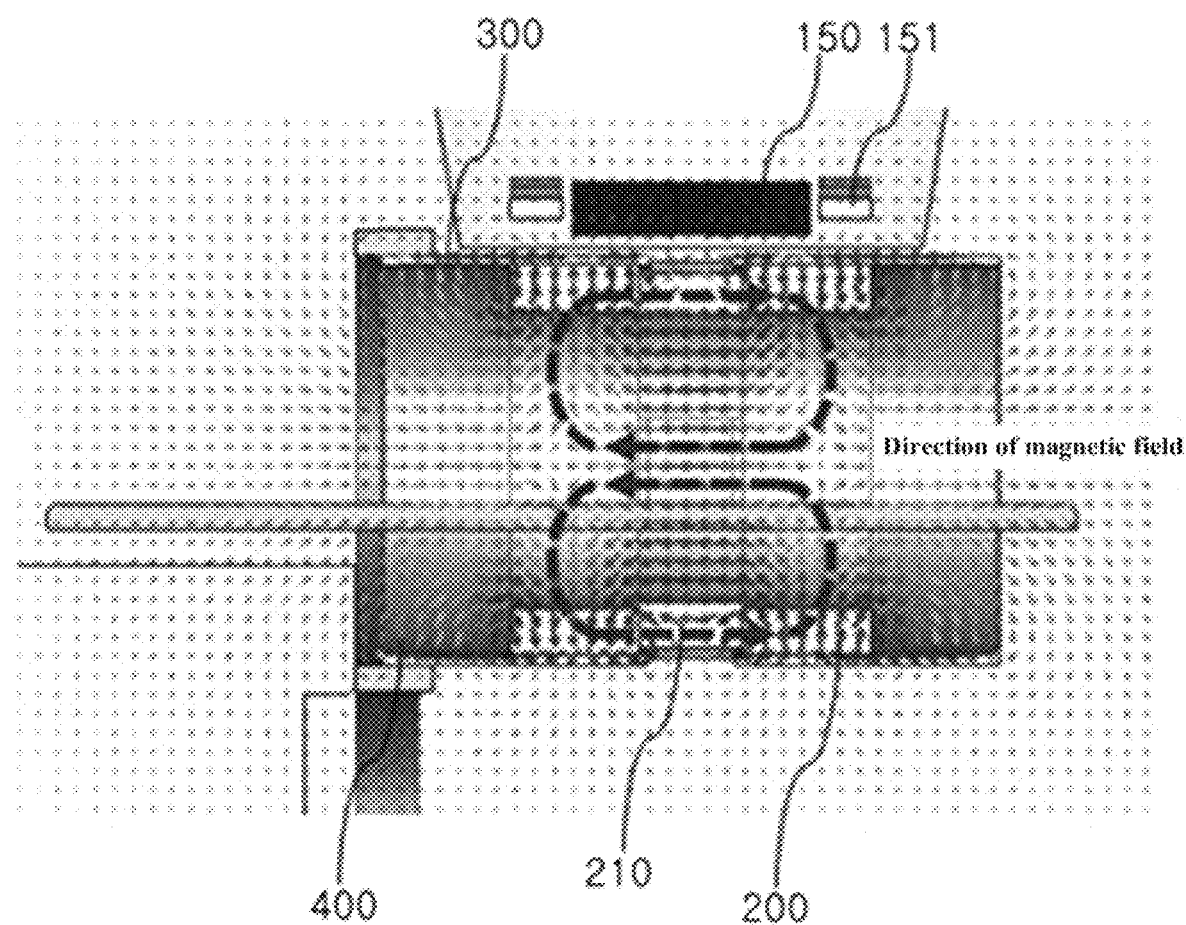

Moreover, FIGS. 13A and 13B illustrate a magnetic field distribution in an inner area of the radiation treatment device 10, according to an embodiment of the inventive concept.

In more detail, FIG. 13A illustrates that the magnetic field generating unit 200 is configured by using an electromagnet. FIG. 13B illustrates that the magnetic field generating unit 200 is configured by using a permanent magnet.

As illustrated in FIG. 13, in the radiation treatment device 10 according to an embodiment of the inventive concept, the magnetic field generating unit 200 is provided in an inner area of the magnetic field shield unit 300 to form a magnetic field in a direction perpendicular to a direction of the radiation irradiated by the radiation generating unit 100.

At this time, in the radiation treatment device 10 according to an embodiment of the inventive concept, the magnetic field shield unit 300 is implemented with a cylindrical magnetic material, and simultaneously attenuates the magnetic field leaking to the outside area while a magnetic circuit structure for the magnetic field formed from the magnetic field generating unit 200 is formed.

Moreover, the magnetic field focusing unit 400 is provided at opposite ends of the inner area of the magnetic field shield unit 300 to focus the magnetic field of the inner area to increase the intensity of the magnetic field formed in the affected tissue.

Furthermore, as illustrated in FIGS. 13A and 13B, the magnetic field focusing unit 400 may include an outer portion 410 of a first outer diameter located on the side of the magnetic field generating unit 200, and an inner portion 420 of a second outer diameter that is located inside the magnetic field generating unit 200. In this case, the first outer diameter may have a larger value than the second outer diameter. A fastening structure may be formed to correspond to a shape of the magnetic field generating unit 200.

Besides, the magnetic field generating unit 200 may include a plurality of electromagnets or permanent magnets, which are arranged to form a left-right symmetrical structure on the basis of an axis to which radiation is irradiated.

Furthermore, as illustrated in FIG. 13B, the magnetic field generating unit 200 may be configured by using a permanent magnet. In the case, in the magnetic field generating unit 200, a permanent magnet may be additionally positioned between a plurality of magnets arranged to form the left-right symmetrical structure to form a Halbach array structure.

Furthermore, in the magnetic field generating unit 200, features such as magnetic field intensity and an external leakage magnetic field may be further improved by additionally arranging a permanent magnet having a magnetic field direction opposite to a central magnetic field direction between a plurality of magnets arranged to form the left-right symmetrical structure.

Figure 14A:
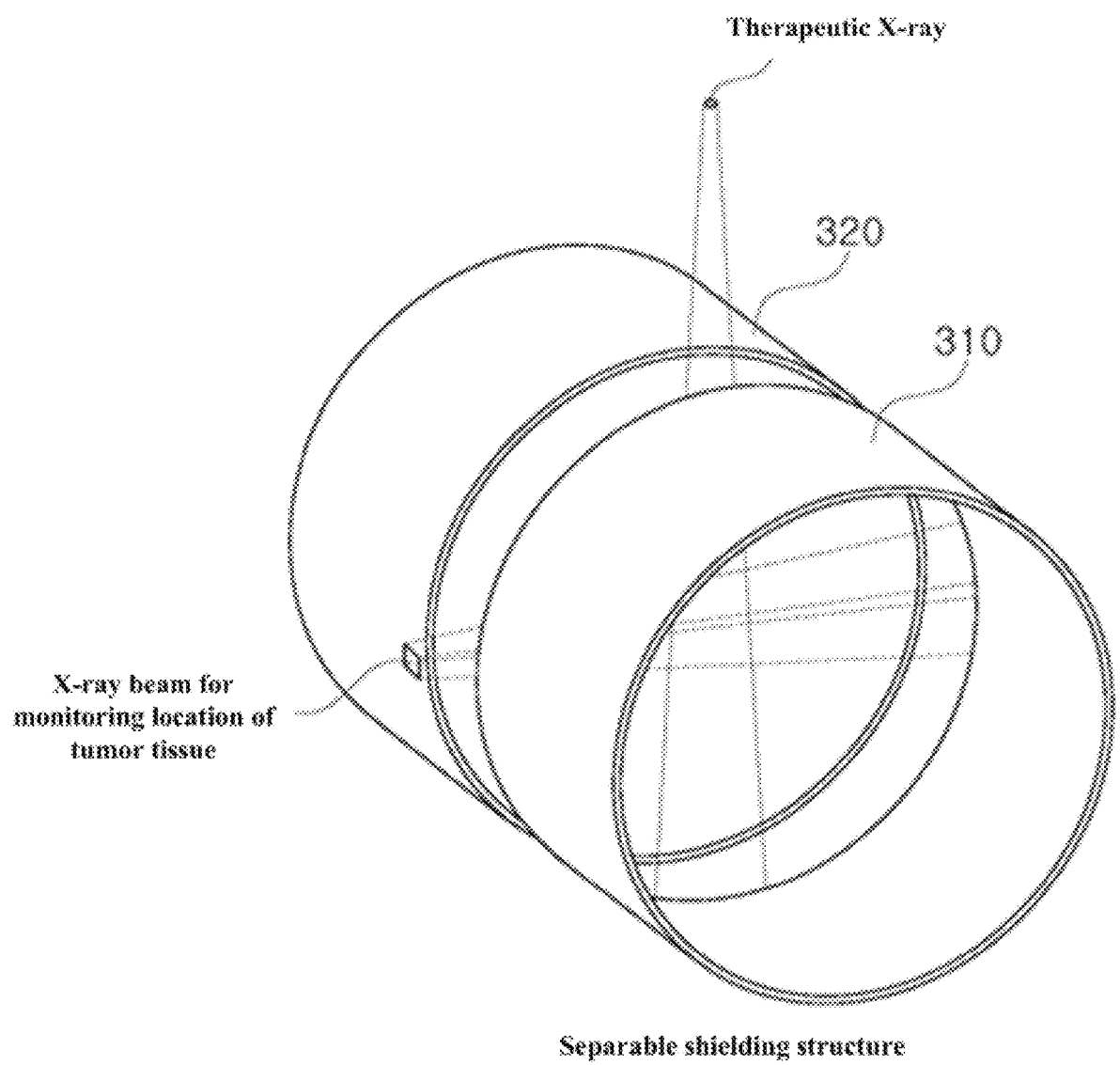
FIGS. 14A and 14B illustrate configurations of a magnetic field shield unit of a radiation treatment device, according to another embodiment of the inventive concept.
Figure 14B:
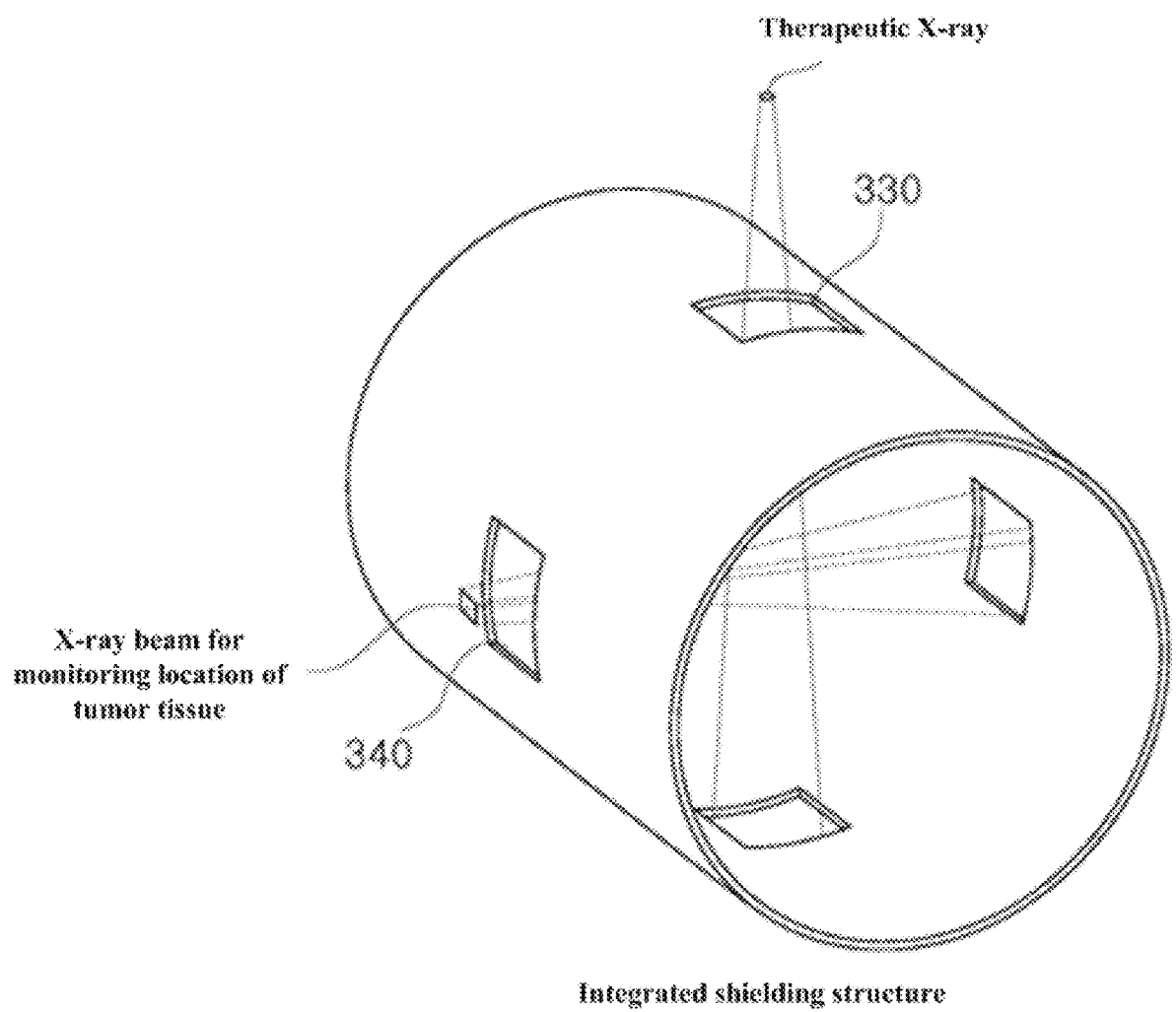

In addition, FIGS. 14A and 14B illustrate configurations of the magnetic field shield unit 300 of the radiation treatment device 10, according to an embodiment of the inventive concept.

First of all, as illustrated in FIG. 14A, the magnetic field shield unit 300 may include two cylindrical magnetic materials 310 and 320 arranged on left and right sides of an axis to which radiation is irradiated (=a separable shielding structure). In this case, the radiation generating unit 100 may irradiate radiation to affected tissue through a space between the two cylindrical magnetic materials 310 and 320.

Moreover, as illustrated in FIG. 14B, the magnetic field shield unit 300 may include a cylindrical magnetic material having a first opening structure 330 through which radiation is capable of passing (=integrated shielding structure). In this case, the radiation generating unit 100 may irradiate radiation to the affected tissue through the first opening structure. At this time, it is desirable that the magnetic field shield unit 300 should operate in conjunction with the radiation generating unit 100 such that the radiation is capable of being irradiated through the first opening structure 330. Furthermore, it is desirable that the magnetic field shield unit 300 should be provided with a second opening structure 340 for irradiating a radiation beam for monitoring the affected tissue.

FIGS. 15A to 15C and 16 illustrate a magnetic field distribution according to the type of the magnetic field shield unit 300 of the radiation treatment device 10, according to an embodiment of the inventive concept.

Figure 15A:
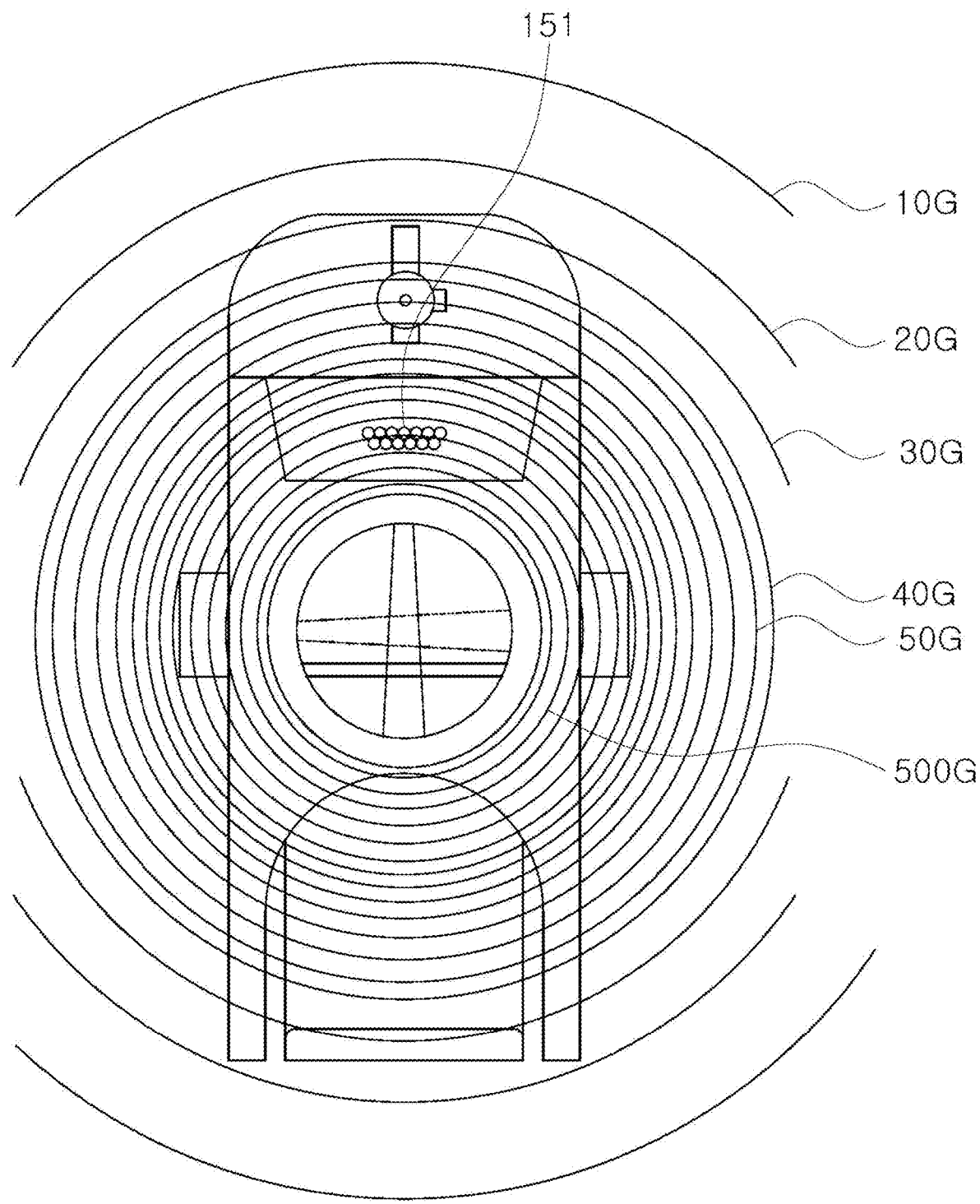
FIGS. 15A to 15C and 16 illustrate a magnetic field distribution according to the type of a magnetic field shield unit of a radiation treatment device, according to an embodiment of the inventive concept.

First of all, FIG. 15A shows a magnetic field distribution when the magnetic field shield unit 300 having the separable shielding structure of FIG. 14A is provided. As illustrated in FIG. 15A, it may be seen that the external magnetic field in the motor 151 has a high value close to 450 G.

Figure 15B:
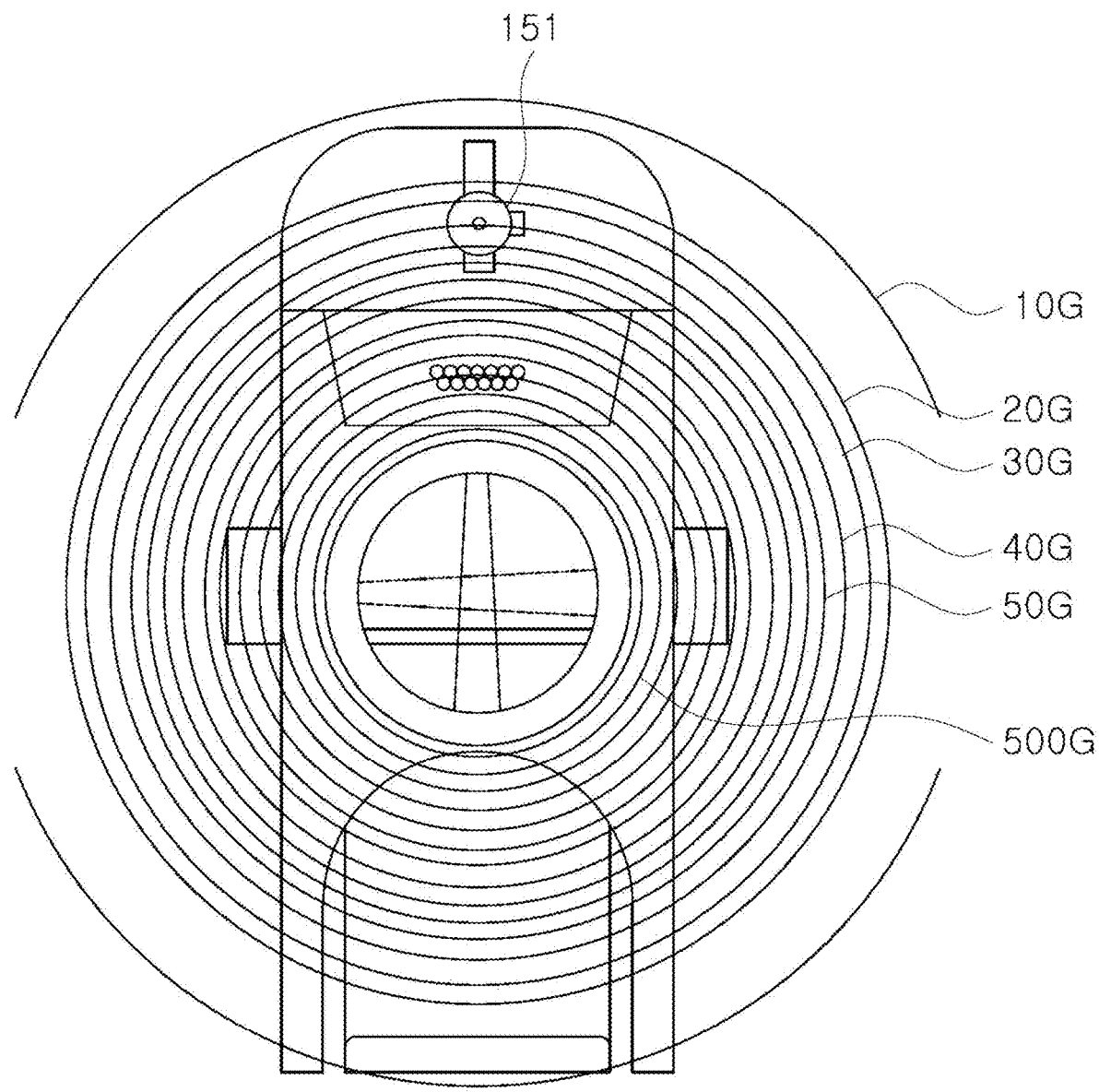

Moreover, FIG. 15B shows a magnetic field distribution when the magnetic field shield unit 300 having the integrated shielding structure of FIG. 14B is provided. As illustrated in FIG. 15B, it may be seen that the external magnetic field in the motor 151 has a value close to 300 G.

Figure 15C:
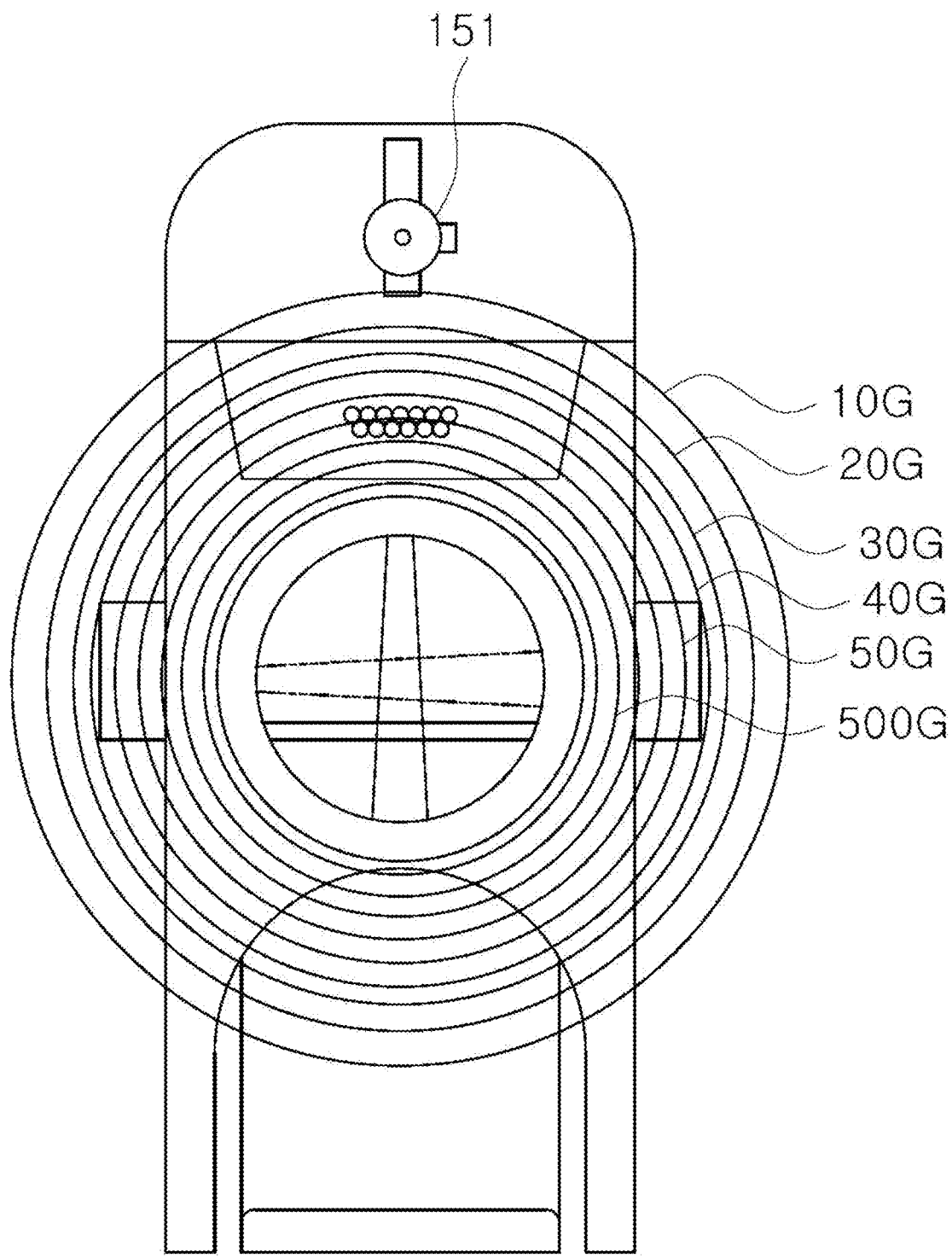

Furthermore, FIG. 15C shows the magnetic field distribution when the magnetic field generating unit 200 having the Halbach magnet 210 are provided together with the magnetic field shield unit 300 having the integrated shielding structure of FIG. 14B. As illustrated in FIG. 15C, it may be identified that an external magnetic field in the motor 151 is limited to about 100 G.

Figure 16:
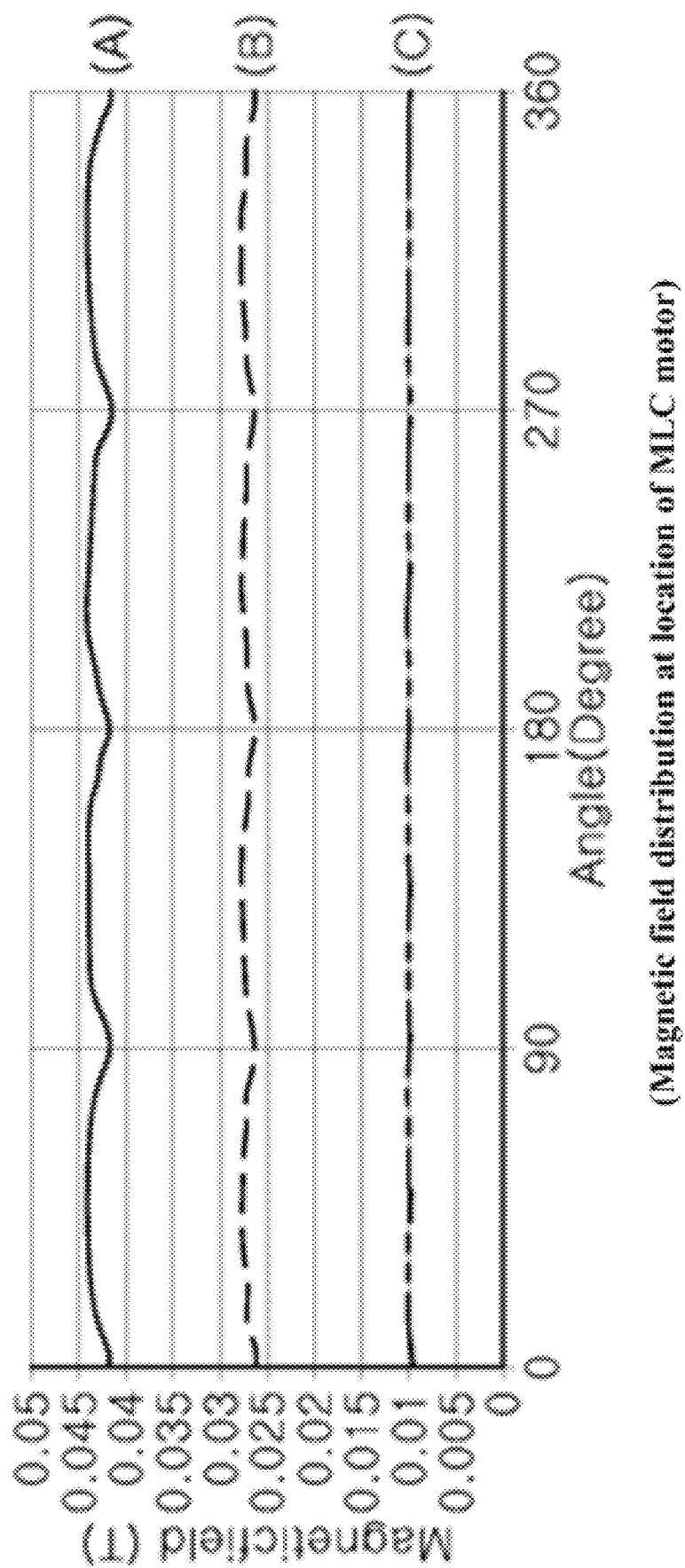

In more detail, FIG. 16 illustrates a distribution of the magnetic field at a location of the motor 151 according to an angle in the cases of FIGS. 15A to 15C with a graph. As illustrated in FIG. 16, it may be seen that a magnetic field is present in a range from about 0.041 Tesla (T) to about 0.045 T when the magnetic field shield unit 300 having a separable shielding structure is provided (FIG. 16(A)). It may be seen that a magnetic field is present in the range of about 0.026 T to 0.028 T when the magnetic field shield unit 300 having an integrated shielding structure is provided (FIG. 16(B)).

In particular, when the magnetic field generating unit 200 having the Halbach magnet 210 is provided together with the magnetic field shield unit 300 having the integrated shielding structure (FIG. 16(C)), a magnetic field has about 0.01 T. It may be seen that malfunctions of the electron gun 110, the linear accelerator 120, and the motor 151 may be effectively prevented by suppressing an external magnetic field by the magnetic field generating unit 200.

Accordingly, while the magnetic field generating unit 200 forms a magnetic field on the affected tissue in a direction perpendicular to an irradiation direction of the radiation, the radiation treatment device 10 according to another embodiment of the inventive concept may attenuate the magnetic field leaking to the outer area by arranging the magnetic field generating unit 200 in an inner area of the magnetic field shield unit 300, thereby effectively suppressing the malfunction that may occur due to leakage of a magnetic field while the reduction of radiation dose by charged particles that may occur in the affected tissue by irradiation with radiation is prevented.

According to an embodiment of the inventive concept, a magnetic field generating apparatus operating in conjunction with a radiation treatment device for treating affected tissue of a subject by using photon beam radiation may include a magnetic field generating unit that forms a magnetic field inside the subject and a synchronization control unit that synchronizes a radiation pulse corresponding to the photon beam radiation with a magnetic field pulse corresponding to the magnetic field.

According to various embodiments, the synchronization control unit may operate in conjunction with a radiation amount control unit of the radiation treatment device. The synchronization control unit may receive an output period of the photon beam radiation from the radiation amount control unit and may synchronize an output period of the photon beam radiation with an output period of the magnetic field.

According to various embodiments, the magnetic field generating apparatus may further include a pulse detection unit that detects the photon beam radiation. The synchronization control unit may obtain an output period of the photon beam radiation by analyzing the detected photon beam radiation.

According to various embodiments, the synchronization control unit may set a magnetic field generation time range such that a secondary electron generation section generated due to irradiation of the photon beam radiation is included in the magnetic field generation time range after the magnetic field reaches a target value.

According to various embodiments, the synchronization control unit may set a magnetic field generation time range in consideration of a delay time required until the magnetic field reaches a target value.

According to various embodiments, the affected tissue, normal tissue, and low-density space may be located inside the subject, and the low-density space is adjacent to at least one of the affected tissue or the normal tissue. The magnetic field generating unit may form the magnetic field in the low-density space.

According to various embodiments, the magnetic field generating unit may include an electromagnet, a permanent magnet, and a combination of the electromagnet and the permanent magnet. The magnetic field generating unit may rotate around the subject, or may be positioned along a periphery of the subject in a fixed or floating manner.

According to various embodiments, the magnetic field generating unit may include a plurality of electromagnets, a plurality of permanent magnets, or a combination of the plurality of electromagnets and the plurality of permanent magnets, which are arranged in a left-right symmetrical structure, based on an axis on which the radiation is irradiated.

According to various embodiments, the magnetic field generating apparatus may further include a plate-shaped frame in which the subject is seated and in which the electromagnets, the permanent magnets, or the combination are positioned. The plate-shaped frame may include a space in which the electromagnets, the permanent magnets, or the combination moves.

According to an embodiment of the inventive concept, a radiation treatment device may operate in conjunction with a magnetic field generating apparatus of claim 1 and may include a radiation generating unit that irradiates radiation to the affected tissue of the subject.

According to an embodiment of the inventive concept, a magnetic field generating apparatus operating in conjunction with a radiation treatment device for treating affected tissue of a subject by using photon beam radiation may include a magnetic field generating unit that forms a magnetic field inside the subject and a synchronization control unit that synchronizes a radiation pulse corresponding to the photon beam radiation with a magnetic field pulse corresponding to the magnetic field.

According to an embodiment of the inventive concept, the synchronization control unit may operate in conjunction with a radiation amount control unit of the radiation treatment device. The synchronization control unit may receive an output period of the photon beam radiation from the radiation amount control unit and may synchronize an output period of the photon beam radiation with an output period of the magnetic field.

According to an embodiment of the inventive concept, the magnetic field generating apparatus may further include a pulse detection unit that detects the photon beam radiation. The synchronization control unit may obtain an output period of the photon beam radiation by analyzing the detected photon beam radiation.

The synchronization control unit may set a magnetic field generation time range such that a secondary electron generation section generated due to irradiation of the photon beam radiation is included in the magnetic field generation time range after the magnetic field reaches a target value.

The synchronization control unit may set a magnetic field generation time range in consideration of a delay time required until the magnetic field reaches a target value.

According to an embodiment of the inventive concept, the affected tissue, normal tissue, and low-density space may be located inside the subject, and the low-density space is adjacent to at least one of the affected tissue or the normal tissue. The magnetic field generating unit may form the magnetic field in the low-density space.

According to an embodiment of the inventive concept, the magnetic field generating unit may include an electromagnet, a permanent magnet, and a combination of the electromagnet and the permanent magnet. The magnetic field generating unit may rotate around the subject, or may be positioned along a periphery of the subject in a fixed or floating manner.

According to an embodiment of the inventive concept, the magnetic field generating unit may include a plurality of electromagnets, a plurality of permanent magnets, or a combination of the plurality of electromagnets and the plurality of permanent magnets, which are arranged in a left-right symmetrical structure, based on an axis on which the radiation is irradiated.

According to an embodiment of the inventive concept, the magnetic field generating apparatus may further include a plate-shaped frame in which the subject is seated and in which the electromagnets, the permanent magnets, or the combination are positioned. The plate-shaped frame may include a space in which the electromagnets, the permanent magnets, or the combination moves.

Figure 17:
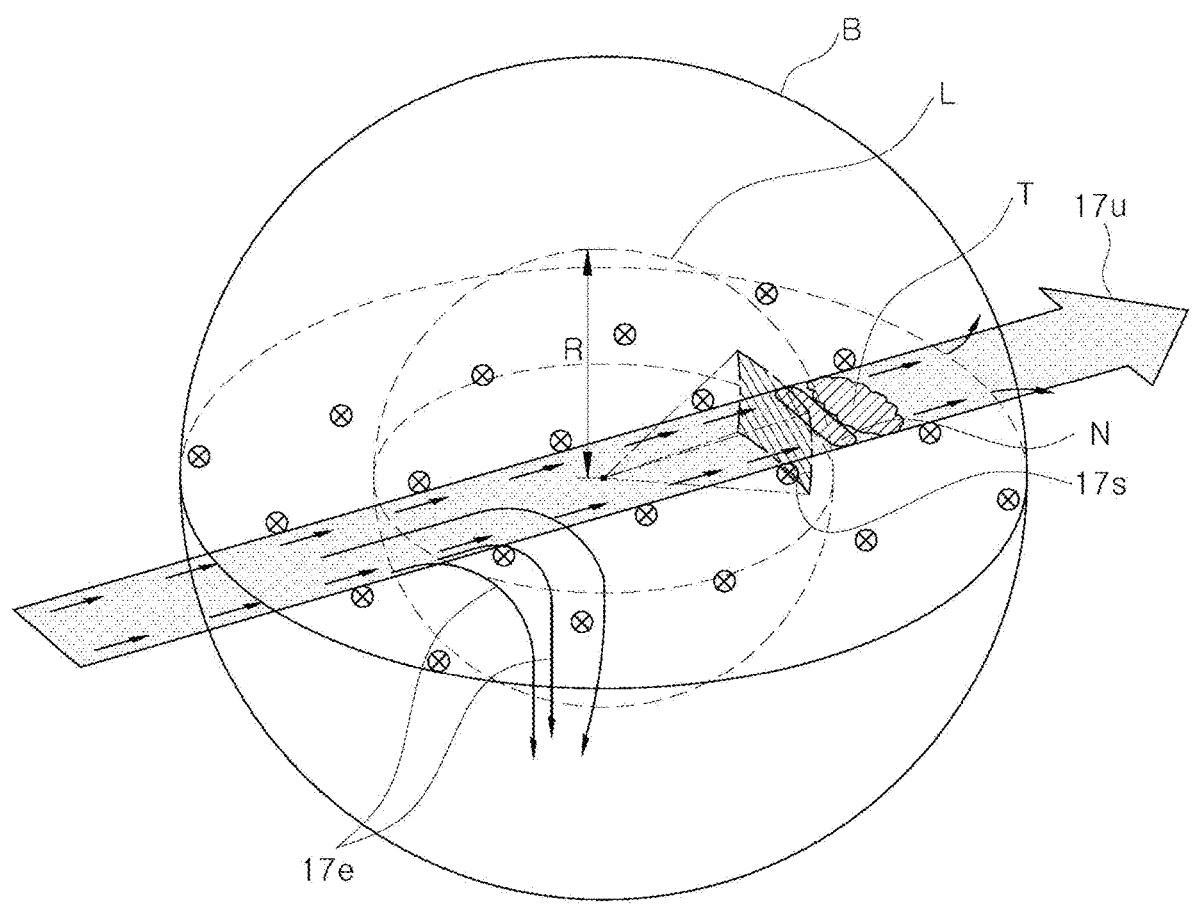
FIG. 17 is a view for describing an operation of a magnetic field generating apparatus based on a reach density per unit area of secondary electrons, according to an embodiment of the inventive concept.

FIG. 17 is a view for describing an operation of a radiation and magnetic field generating apparatus based on a reach density per unit area of secondary electrons, according to an embodiment of the inventive concept.

Referring to FIG. 17, a synchronization control unit may control the formation of photon beam radiation such that density per unit area of secondary electrons 17e reaching a subject is less than a predetermined value.

In the meantime, according to an embodiment of the inventive concept, a magnetic field generating unit may include an insertion structure that is provided to be inserted into a body and forms a low-density space.

The shape of this insertion structure may be predetermined based on a location relationship between an area irradiated with photon beam radiation and an affected part.

That is, when photon beam radiation is irradiated to a user, an area where photon beam radiation is irradiated and a location of the affected part may be determined in advance, and then the formation of a low-density space may be calculated to prevent damage to normal tissue by allowing less secondary electrons to reach the normal tissue around the affected part.

In the meantime, the insertion structure may be generated to correspond to a shape of this low-density space.

Moreover, the insertion structure may be provided as a balloon structure for implementing the above-described shape. A detailed description of the insertion structure will be described below.

In the meantime, the synchronization control unit may control the formation of a magnetic field such that at least some of secondary electrons move to a low-density space other than a normal tissue 'N' based on a relationship between an area irradiated with photon beam radiation and a location of an affected part 'T'.

FIG. 17 also shows that the secondary electrons generated in this way move to a low-density space other than the normal tissue 'N'.

Through this operation, the synchronization control unit may control the secondary electrons to move while the secondary electrons avoid the normal tissue 'N' adjacent to the affected tissue 'T'.

FIG. 17 shows a spherical subject 'B' forming the low-density space having a radius of 'R', according to an embodiment of the inventive concept.

In the meantime, in the same situation as the situation in FIG. 17, the relationship between photon beam radiation generated by a radiation generating unit and a path change of electrons may be expressed by Equation 5 below.

$$R = \frac{E \cdot m}{\sqrt{2} \cdot q \cdot B \sin\theta} \qquad \text{[Equation 5]}$$

Referring to Equation 5, 'R' denotes a length of a radius of the low-density space mentioned above, that is, a movement distance having a direction perpendicular to the movement direction of secondary electrons; 'E' denotes the initial kinetic energy of the secondary electrons generated by supplying radiation from a radiation generating unit; 'q' denotes the charge amount of an electron; 'B' denotes a size of a magnetic field generated by the magnetic field generating unit; and, 'm' denotes the mass of electrons. 'θ' may denote an angle between the traveling direction of electrons and a magnetic field.

As described above, the radiation generating device may store identification information for each subject. Meanwhile, the identification information may include size information of a subject.

At this time, because the synchronization control unit knows the size of the low-density space, the synchronization control unit may generate secondary electrons 17e by applying energy to minimize the effect of radiation on the normal tissue 'N' other than the affected part based on the size.

In this embodiment, it is shown that the subject 'B' is provided in a spherical shape, but there is no limitation on the shape of the subject 'B'.

In the meantime, the synchronization control unit may obtain an image of the subject or may obtain a volume and surface area of the subject from predetermined identification information.

In this case, the low-density space 'L' may be formed by an insertion structure included in the magnetic field generating unit, as will be described later.

The insertion structure may be provided as a balloon-shaped structure and may be inserted into a body to form the low-density space 'L'.

FIG. 17 shows that this insertion structure forms a spherical space 'L' having a radius of R, but there is no limitation on a shape formed by the insertion structure.

The synchronization control unit may control a magnetic field of the secondary electrons 17e formed by photon beam radiation to change a path of secondary electrons and may calculate the amount of the secondary electrons 17e that has changed the path to reach one surface of the low-density space 'L'.

Accordingly, the synchronization control unit may calculate the reach density per unit area of secondary electrons by using an area size of the low-density space and the amount of secondary electrons reaching one surface of the low-density space based on the following equation.

$$D = \frac{C}{S} \quad \text{[Equation 6]}$$

Referring to Equation 6, 'S' may denote a unit area 17S of a part of the low-density space; 'D' may denote the reach density of secondary electrons; and, 'C' may denote the number of secondary electrons reaching the unit area.

In the meantime, in the synchronization control unit, when the reach density of the normal tissue of secondary electrons determined based on Equation 6 described above exceeds a specific value, it may harm normal tissue in addition to the affected part irradiated with radiation.

The synchronization control unit may form a magnetic field such that the density of the secondary electrons 17e reaching a specific area is less than a specific value.

On the basis of this operation, the synchronization control unit may minimize damage to normal tissue 'N' other than the affected part.

The synchronization control unit may control the formation of photon beam radiation 17u such that the reach density per unit area of the secondary electrons 17e reaching the affected part 'T' does not exceed a predetermined value.

As described above, when the photon beam radiation 17u is irradiated to the subject 'B', the secondary electrons are generated at the corresponding location. In the meantime, for the photon beam radiation 17u to reach the subject 'B' around the affected part, the photon beam radiation 17u may also reach the normal tissue 'N' other than the vicinity of the affected part 'T'.

The secondary electrons may also be generated here. The secondary electrons 17e generated outside the vicinity of the affected part are not directly used to treat the affected part 'T'.

However, when the photon beam radiation 17u reaches the subject 'B' around the affected part 'T', secondary electrons may be formed and delivered to the affected part 'T'.

However, because secondary electrons, of which the amount is not less than a specific amount, need to be generated and delivered to the affected part 'T' for the removal and treatment of the affected part, the synchronization control unit may control the radiation generating unit and may control the generation of the radiation 17u to have little effect on the normal tissue 'N' while the photon beam radiation 17u reaches the subject of an area of the affected part 'T'.

In the meantime, the shape of the subject 'B' or a path of secondary electrons presented in FIG. 17 is only an example for describing the operation according to an embodiment of the inventive concept. There is no limitation on the shape of subject 'B', the path of the secondary electrons 17e, and the shape of a magnetic field applied to the secondary electrons 17e.

Figure 18A:
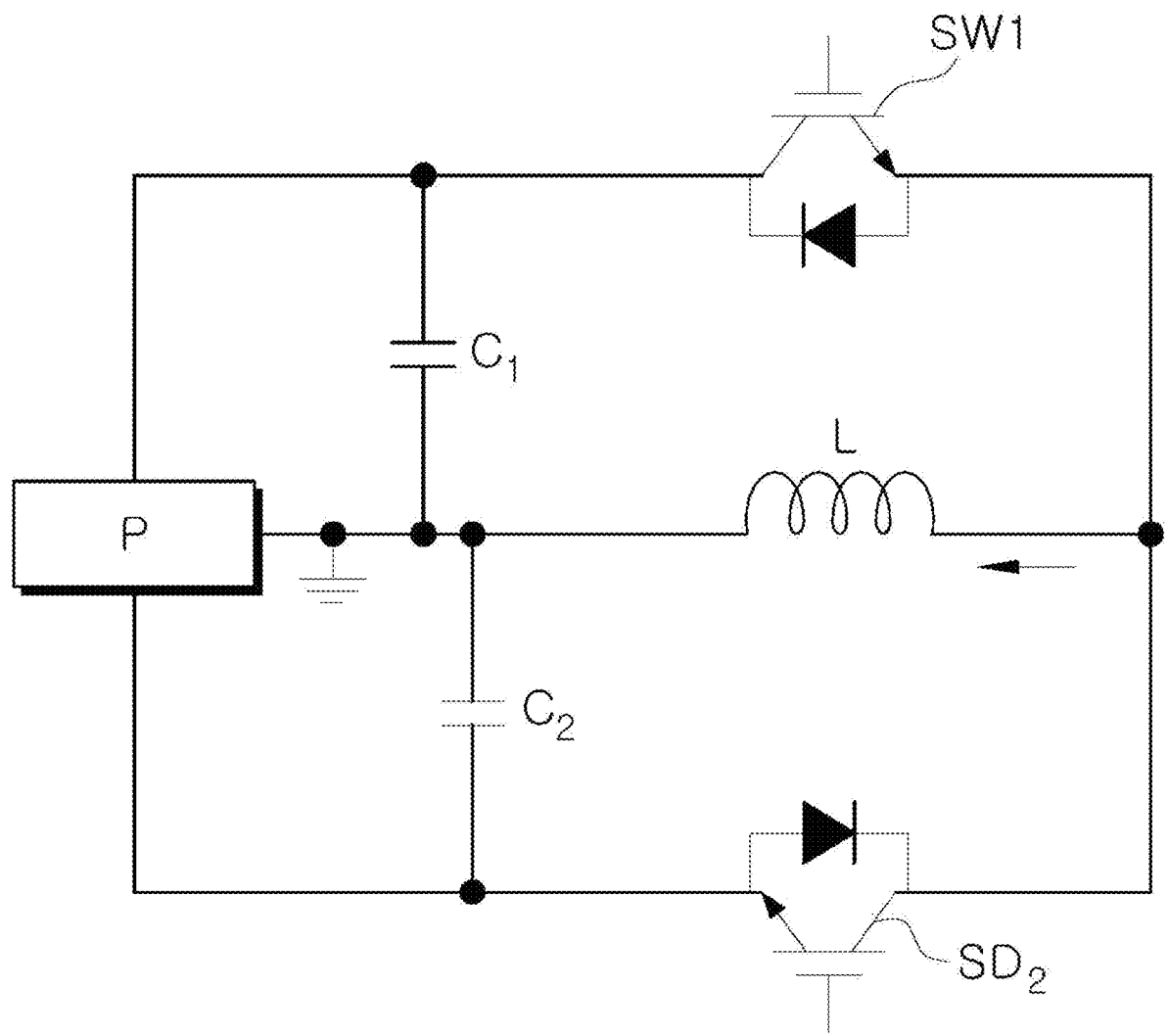
FIG. 18A is a diagram illustrating a circuit diagram constituting a magnetic field generating unit, according to an embodiment of the inventive concept.
Figure 18B:
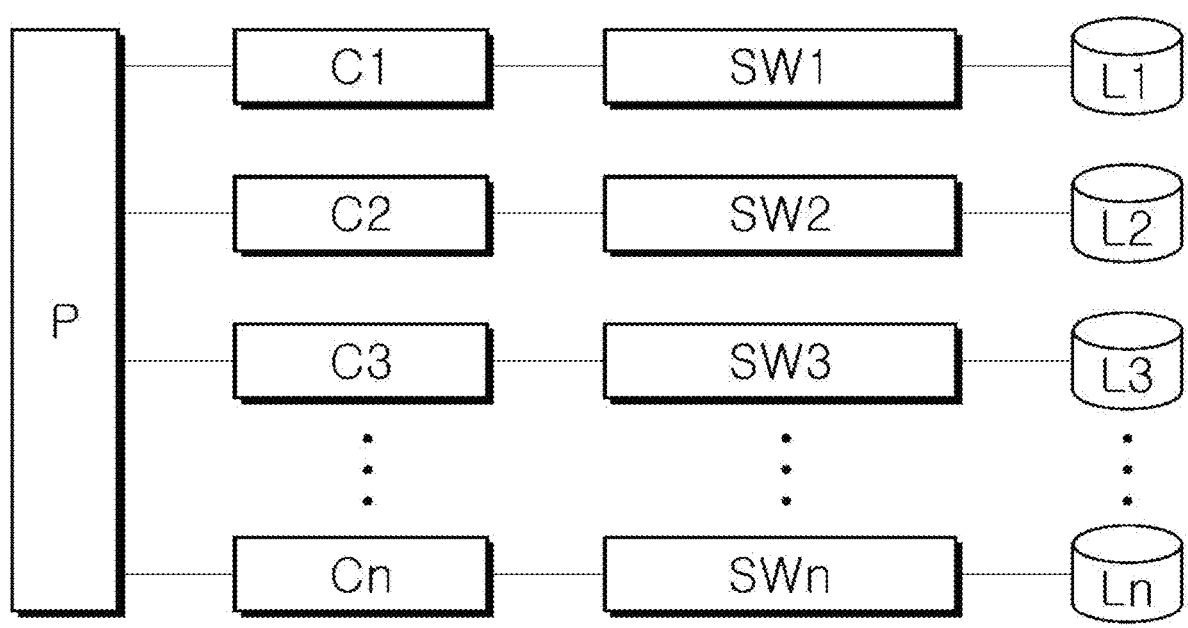
FIG. 18B is a block diagram illustrating a configuration of a magnetic field generating unit, according to an embodiment of the inventive concept.

FIG. 18A is a diagram illustrating a circuit diagram constituting a magnetic field generating unit, according to an embodiment of the inventive concept. FIG. 18B is a block diagram illustrating a configuration of a magnetic field generating unit, according to an embodiment of the inventive concept.

Referring to FIGS. 18A and 18B, a magnetic field generating unit may include at least one coil L, L1, L2, L3, or Ln and a capacitor element C1, C2, C3, or Cn.

Moreover, the magnetic field generating unit may further include a switch element sw1, sw2, sw3, or swn that connects or disconnects the capacitor C1, C2, C3, or Cn to or from the coil L, L1, L2, L3, or Ln.

In the meantime, in an embodiment of the inventive concept, a pulse-type electromagnet may be used to prevent large power consumption, heat generation, and the risk of leakage magnetic field. Accordingly, in the configuration shown in FIGS. 18A and 18B, pulse power for driving a pulse-type magnetic field may be supplied.

In the case, under the control of the synchronization control unit, the pulse power may be supplied to the magnetic field generating unit to form a magnetic field in a state where the caloric value generated by the magnetic field generating unit is not greater than a predetermined value.

The magnetic field generating unit according to an embodiment of the inventive concept may be formed of an electromagnet, in which several small coils L, L1, L2, L3, and Ln are combined, for a short pulse.

Besides, the capacitors C1, C2, C3, and Cn for outputting a large amount of current in a short time may be provided in a pulse-type magnetic field generating unit.

In the meantime, the synchronization control unit may form a magnetic field by controlling the current supplied to the coil L, L1, L2, L3, or Ln based on a location relationship between an area irradiated with photon beam radiation and an affected part.

At this time, the synchronization control unit may control the current delivered to the coils L, L1, L2, L3, and Ln by controlling the switch elements sw1, sw2, sw3, and swn and supplied power P.

On the other hand, when the magnetic field generating unit is provided in a form of a catheter, the above-described coils L, L1, L2, L3, and Ln may be provided in an area to be inserted into a body, and a detailed description related thereto will be described later.

In the meantime, the circuit diagram and block diagram of the magnetic field generating unit shown in FIGS. 18A and 18B are only one embodiment of the inventive concept. When a module includes the coils L, L1, L2, L3, and Ln, the switches sw1, sw2, sw3, and swn and the capacitors C1, C2, C3, and Cn, there is no limitation in a configuration of the magnetic field generating unit.

Figure 19A:
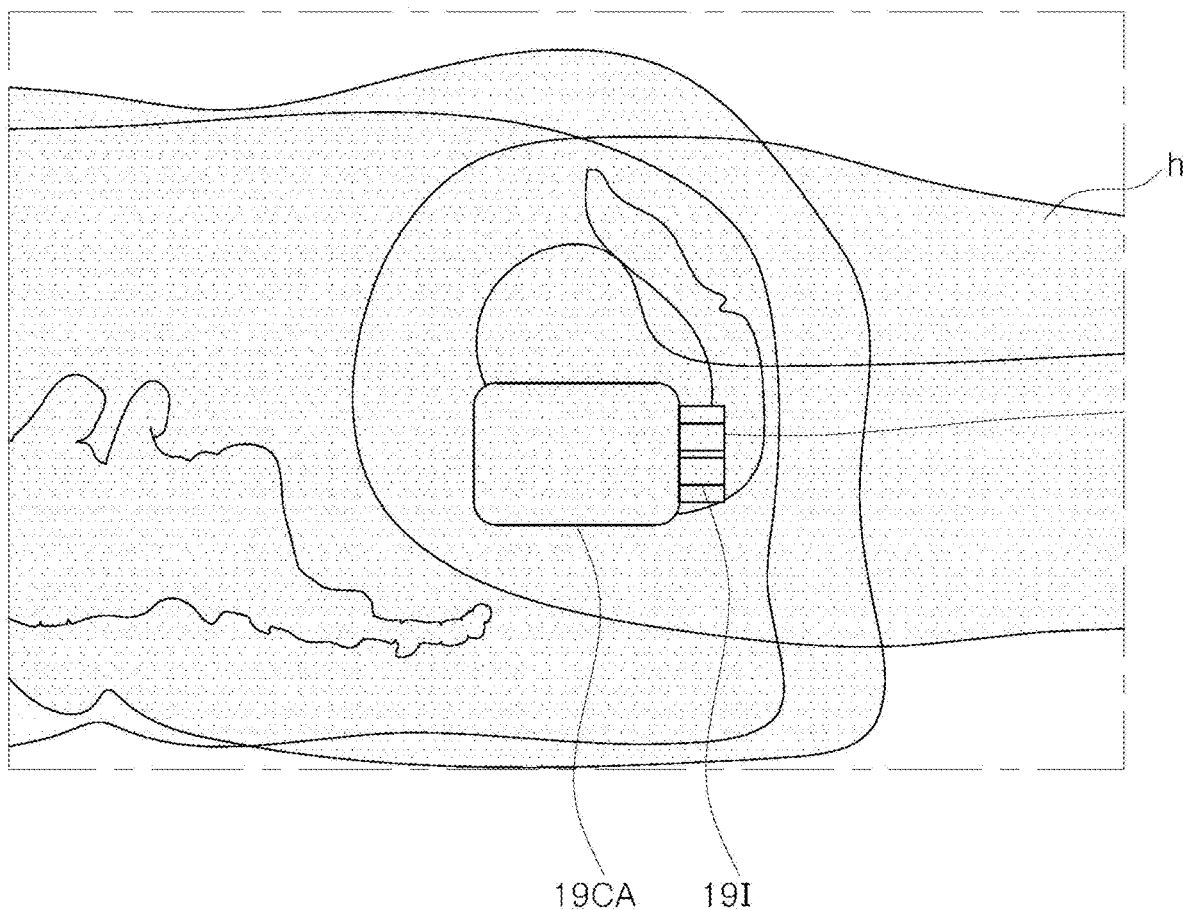
FIGS. 19A and 19B are views for describing a shape in which a coil is provided in a balloon-shaped insertion structure.
Figure 19B:
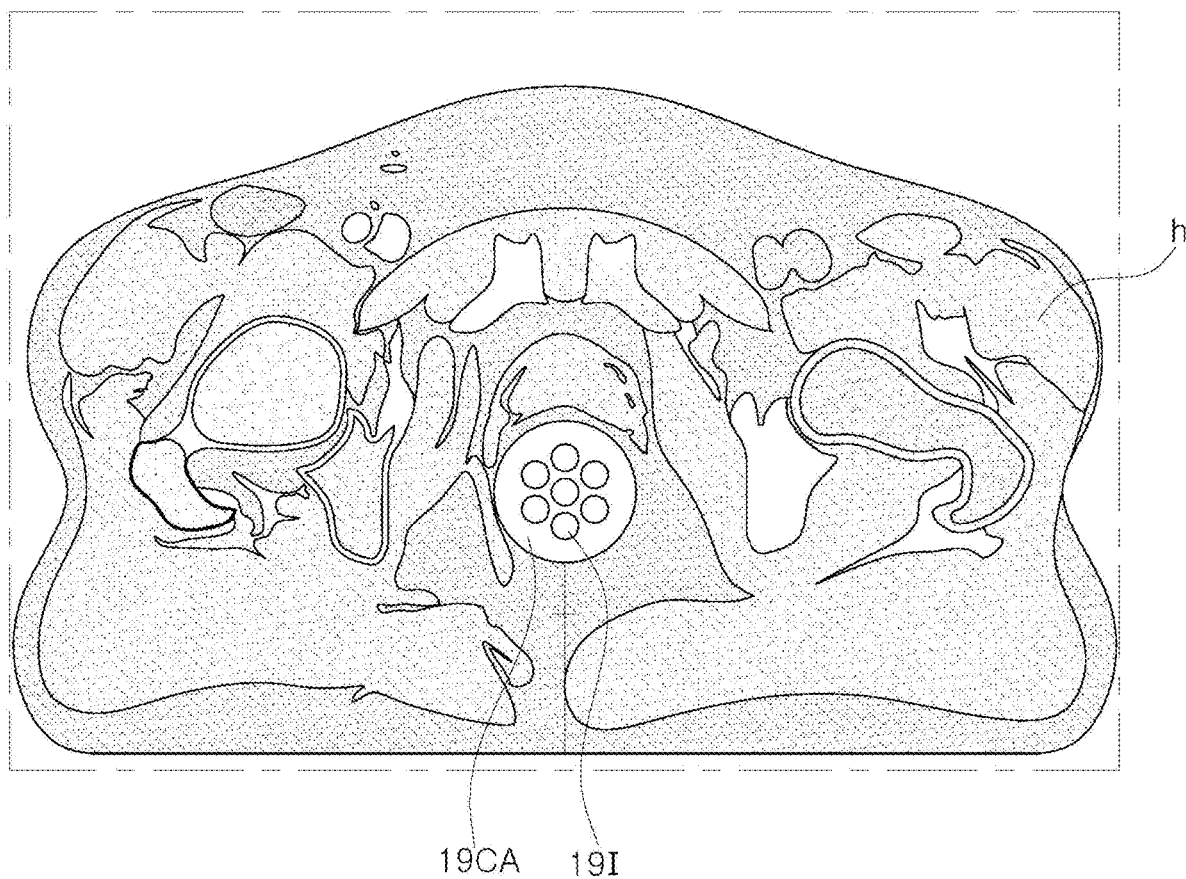

FIGS. 19A and 19B are views for describing a shape in which a coil is provided in a balloon-shaped insertion structure.

FIG. 19A is a view showing a shape of a side surface of an insertion structure 19CA is inserted into a body. FIG. 19B is a view showing a shape of a front surface of the insertion structure 19CA is inserted into the body.

In the meantime, a magnetic field generating unit may include a first area corresponding to an insertion structure provided to be inserted into the body, and a second area provided as other areas.

Meanwhile, as described above, a coil 191 constituting the magnetic field generating unit may be provided in a first area on the insertion structure as shown in FIGS. 19A and 19B.

In detail, the coil 191 may be provided in the first area of a separate balloon-shaped insertion structure. Although not shown in the drawing, capacitors and switches constituting the magnetic field generating unit may be provided in an area (i.e., the second area) other than the first area.

Hereinafter, when the magnetic field generating unit is provided in the balloon-shaped insertion structure, a path change of secondary electrons and the generation of a magnetic field will be described in detail.

Figure 20A:
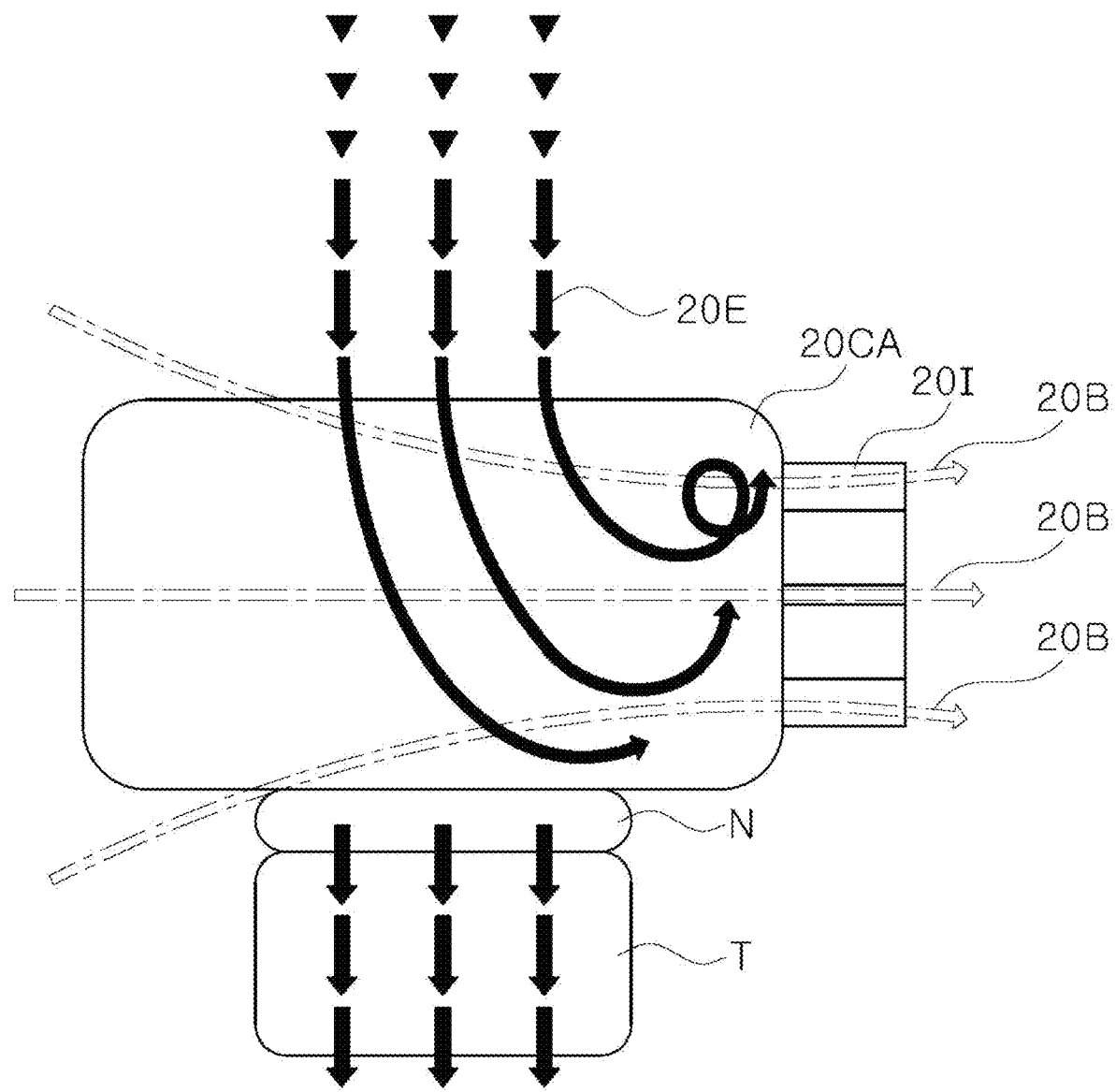
FIGS. 20A and 20B are diagrams for describing an interaction between secondary electrons and a magnetic field in a separate balloon-shaped device.
Figure 20B:
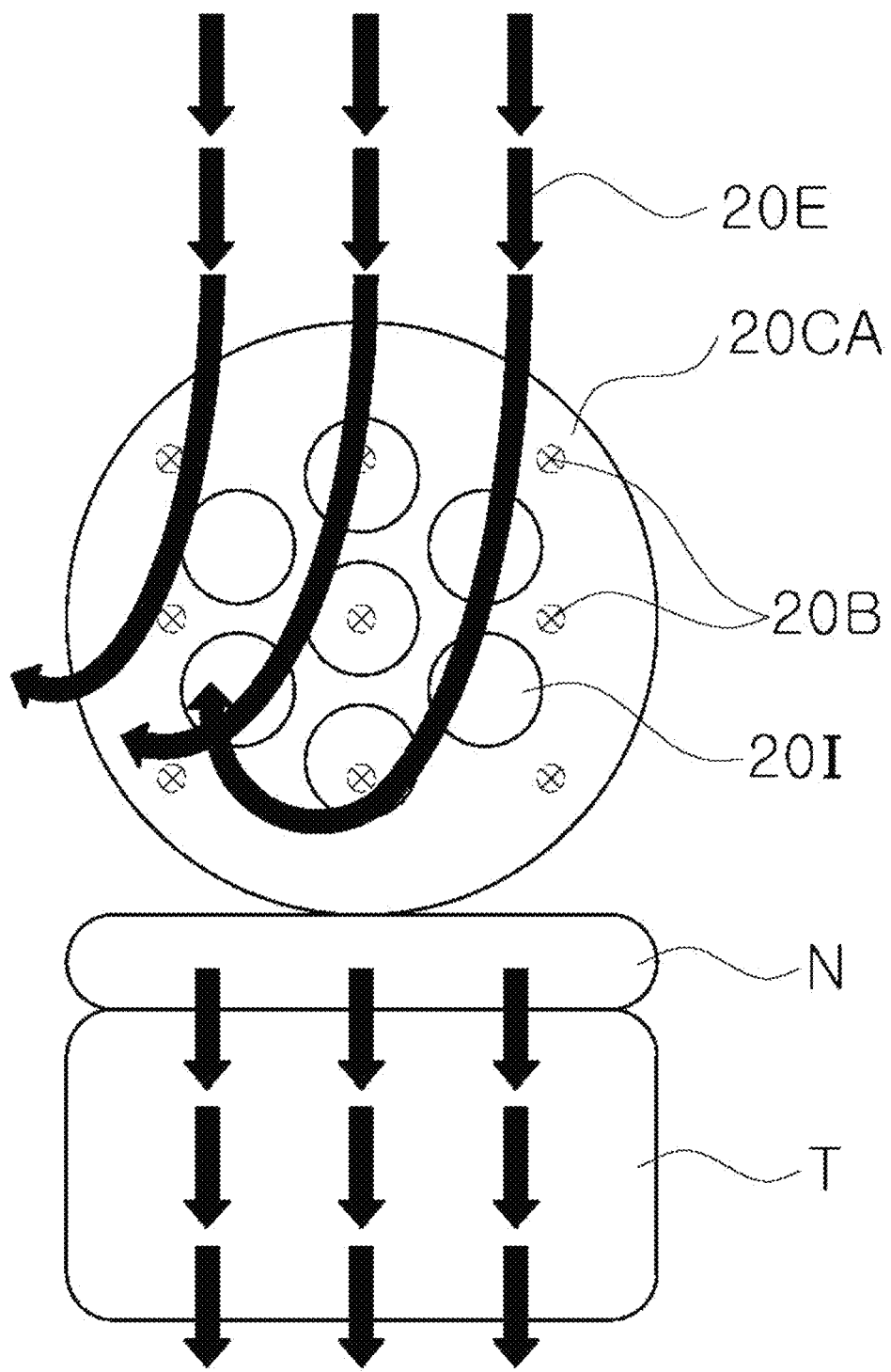

FIGS. 20A and 20B are diagrams for describing an interaction between secondary electrons and a magnetic field in a balloon-shaped insertion structure.

Referring to FIGS. 20A and 20B, an insertion structure 20CA is provided on a subject, and the insertion structure 20CA is provided in a form of a balloon to form a low-density space on the subject.

When a current is applied to a coil 201, a magnetic field 20B may be formed.

In FIG. 20B, a direction of the magnetic field 20B may be formed from the front to the rear.

In the meantime, a synchronization control unit may control the formation of the magnetic field such that an angle between a magnetic force line corresponding to the magnetic field 20B and an irradiation direction of photon beam radiation exceeds a predetermined angle.

When an angle between the direction of the magnetic field and the direction of a current formed by secondary electrons 20E is substantially right angle, the electromagnetic force applied to the secondary electrons 20E may be maximal.

Accordingly, the synchronization control unit may change a location of a coil included in the magnetic field generating unit or a location of a subject such that an angle between the magnetic force line corresponding to the magnetic field 20B and an irradiation direction of photon beam radiation is orthogonal to each other.

On the other hand, as shown in FIG. 20A, the secondary electrons 20E may bypass the traveling direction under the influence of the magnetic field.

At this time, the secondary electrons 20E reach the subject of normal tissue such as mucous membrane tissue, thereby preventing tissue damage.

On the other hand, the photon beam radiation generated by the magnetic field generating unit reaches the normal tissue and thus the secondary electrons 20E may be generated at the corresponding location. The secondary electrons 20E may reach the affected part and thus treatment may be performed.

In this case, the secondary electrons 20E generated in the area of another subject may be bypassed by the magnetic field 20B, and thus may not reach the normal tissue around the affected part. Accordingly, the normal tissue may be protected.

Figure 21:
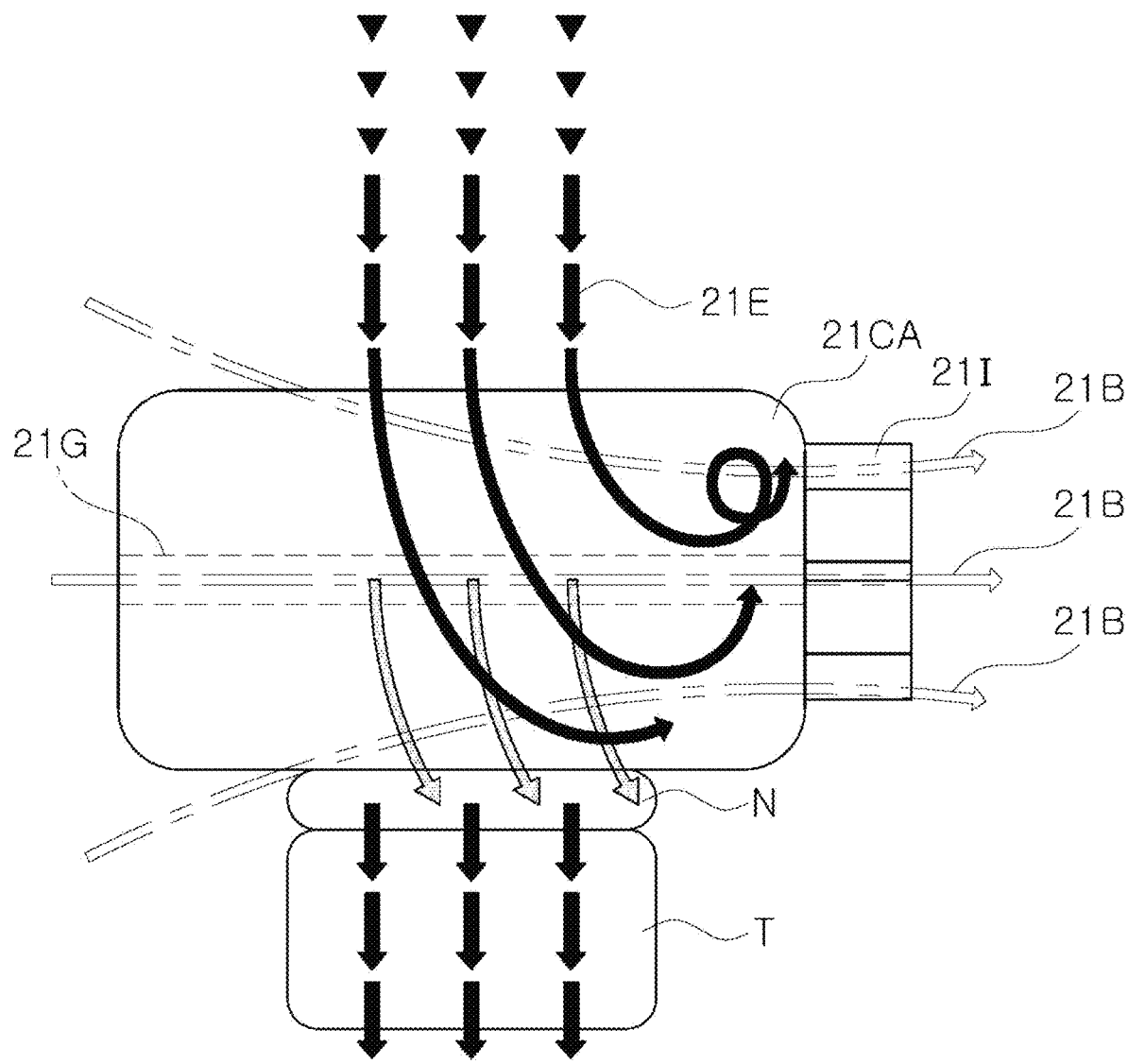
FIG. 21 is a view showing that a guide unit is provided in a separate balloon-shaped device, according to an embodiment of the inventive concept.

FIG. 21 is a view showing that a guide unit is provided in a separate balloon-shaped device, according to an embodiment of the inventive concept.

Referring to FIG. 21, when an insertion structure is provided in a form of a catheter, the insertion structure is provided with a guide unit 21G that supports the catheter inside the catheter. FIG. 21 shows that photon beam radiation reaches the guide unit 21G to generate secondary electrons 21E.

Because the secondary electrons 21E generated by the guide unit 21G have a short distance to bypass a path, unlike the illustration in FIG. 20A, some of the secondary electrons 21E may reach normal tissue.

Unlike the illustration in FIG. 20A, because secondary electrons partially reach normal tissue 'N', damage to the normal tissue may be increased compared to FIG. 20A.

In other words, in the case of FIG. 21, secondary electrons may be newly generated in the guide unit. The secondary electrons generated at this location may reach the normal tissue 'N' and may damage the normal tissue. However, even at this time, the amount of secondary electrons reaching the tumor 'T' is the same.

Accordingly, it may be preferable for a user to employ a catheter 21CA, in which the guide unit 21G is not present, to prevent damage to the normal tissue 'N'.

In the meantime, a configuration of the insertion structure described with reference to FIGS. 20A, 20B and 21 is only one embodiment of the inventive concept, and there is no limitation on a shape of the insertion structure and the configuration of the catheter.

Figure 22A:
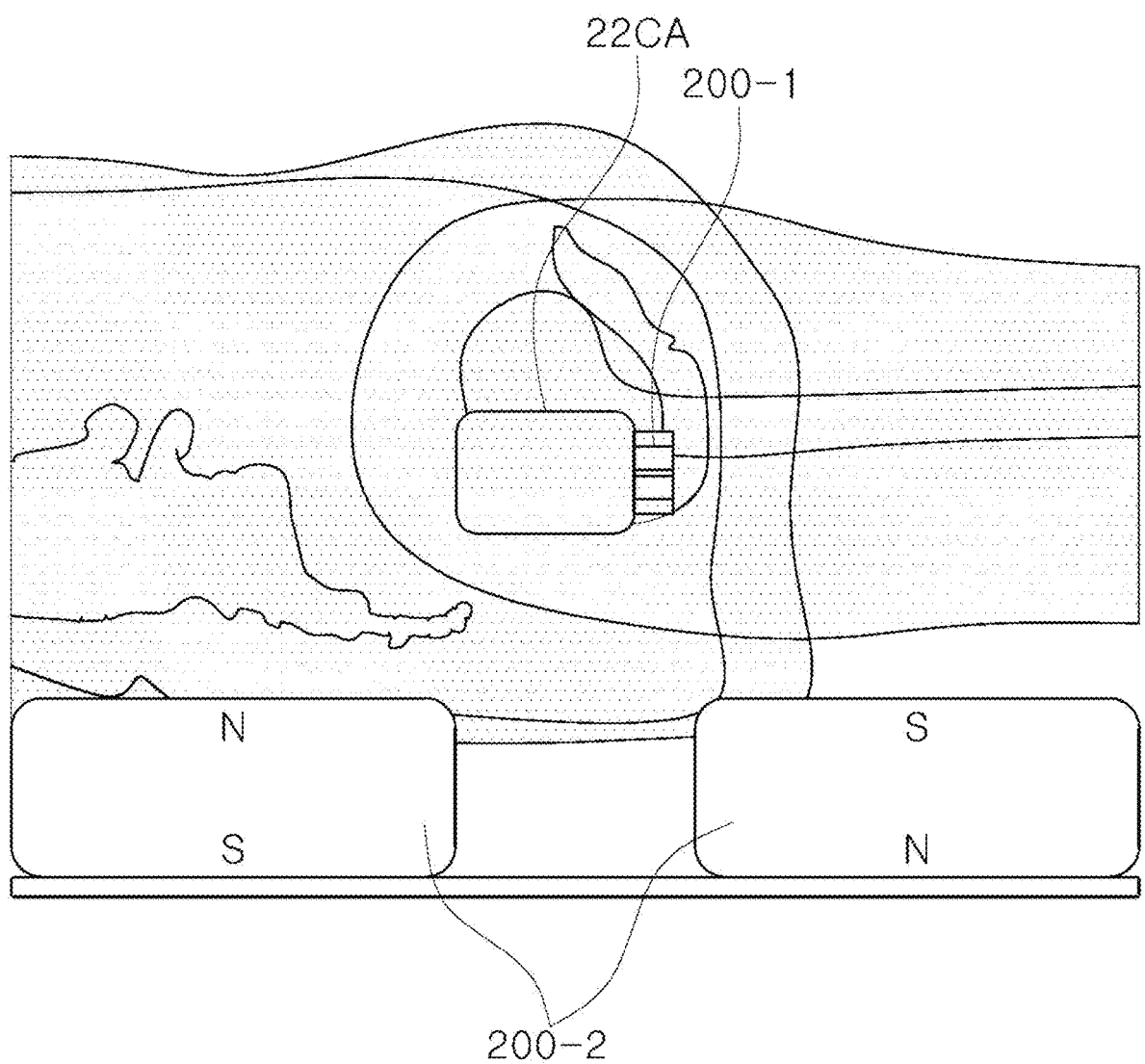
FIGS. 22A and 22B are diagrams for describing an interaction between a magnetic field generating unit provided in a magnetic field generating device and a coil provided in a balloon-shaped separate device, according to an embodiment of the inventive concept.
Figure 22B:
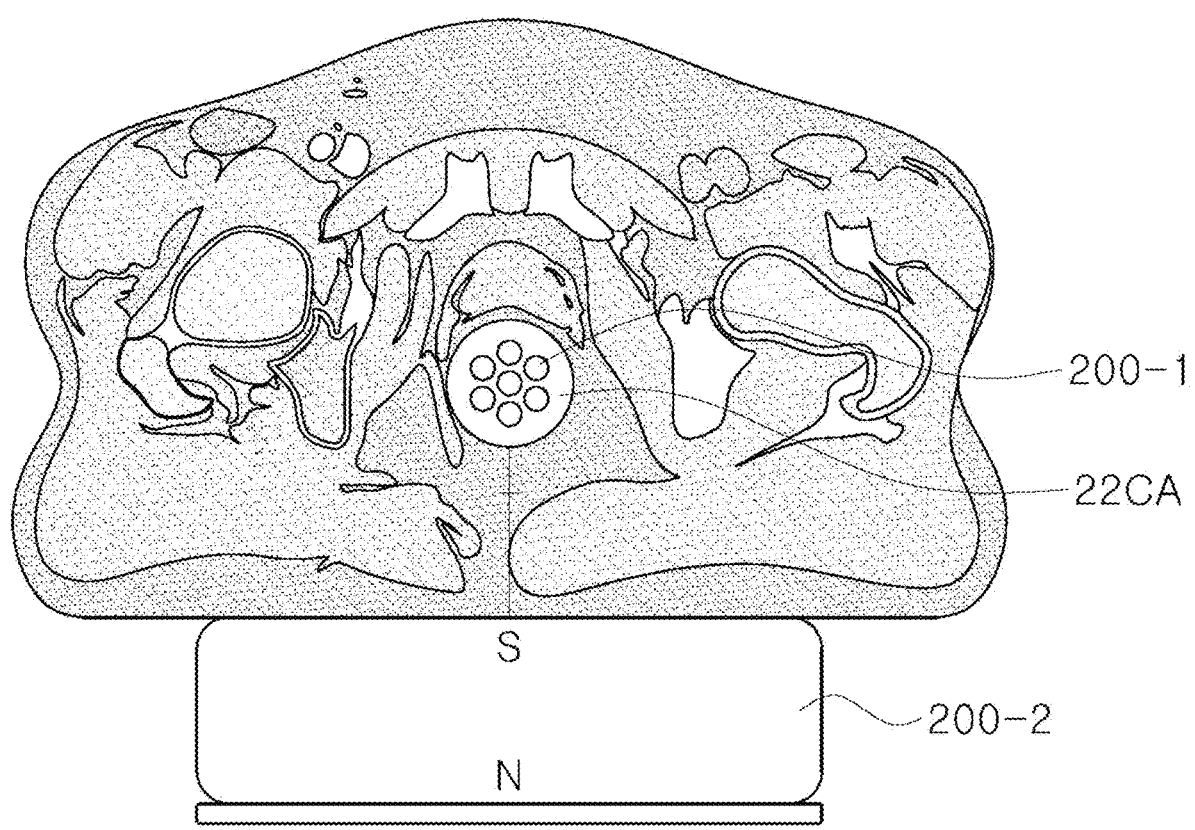

FIGS. 22A and 22B are diagrams for describing an interaction between a magnetic field generating unit provided in a magnetic field generating device and a coil 200-1 provided in a balloon-shaped insertion structure 22CA, according to an embodiment of the inventive concept.

Referring to FIGS. 22A and 22B, a magnetic field generating unit 200-2 may be provided in a magnetic field generating apparatus 200-2 in addition to a catheter to form a magnetic field.

That is, a synchronization control unit may form a magnetic field by supplying a current to a coil 200-1 provided in the insertion structure itself, or may bypass the path of secondary electrons from the subject by using the magnetic field generated by the magnetic field generating apparatus 200-2.

The coil 200-1 provided in the insertion structure 22CA is provided in a form of an electromagnet to form a magnetic field. The permanent magnet 200-2 provided in the magnetic field generating apparatus forms a magnetic field. FIGS.

22A and 22B show a configuration capable of controlling a path of secondary electrons of the subject.

As shown in FIG. 22A, a magnetic field formed by the magnet 200-2 of the magnetic field generating apparatus may be formed in the same direction as the magnetic field formed by the coil 200-1 provided in an insertion structure. Accordingly, a magnetic field generated by the coil 200-1 may overlap a magnetic field generated from the magnet 200-2 of the magnetic field generating apparatus, and thus the path of secondary electrons may be changed.

Figure 23A:
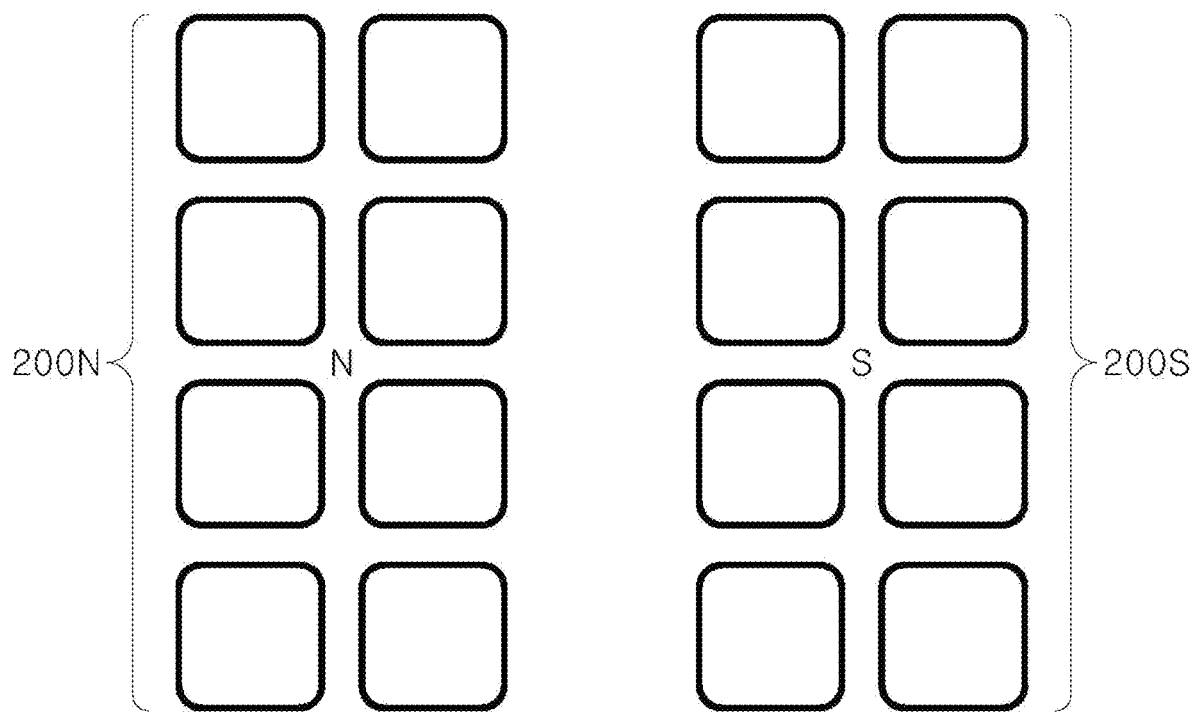
FIGS. 23A and 23B are views showing that a magnetic field generating unit provided in a magnetic field generating apparatus is formed of a set of coils, according to an embodiment of the inventive concept.
Figure 23B:
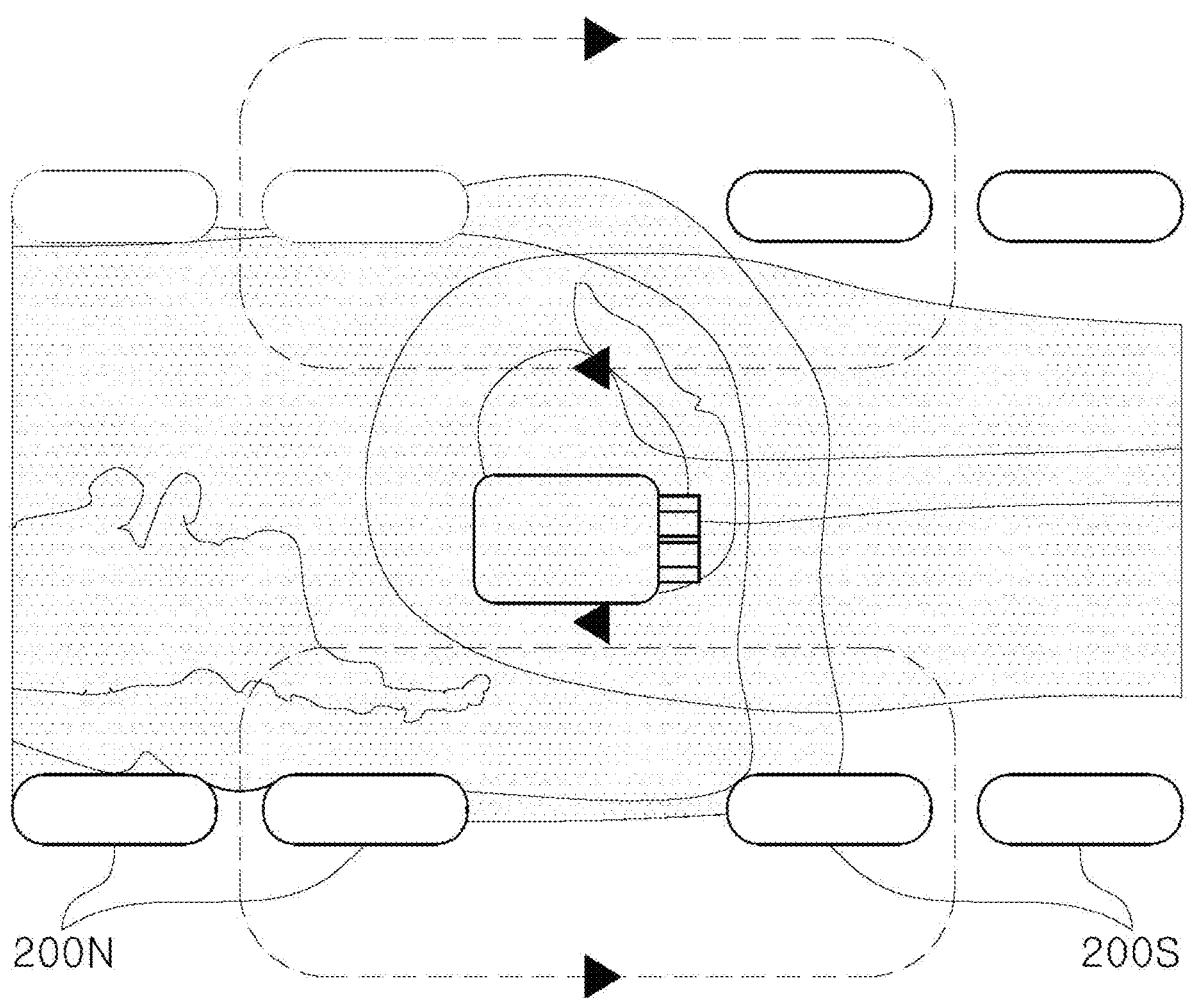

FIGS. 23A and 23B are views showing that a magnetic field generating unit provided in a magnetic field generating apparatus is formed of a set of coils 200N and 200S, according to an embodiment of the inventive concept.

A magnet provided in a magnetic field generating apparatus may be provided as a permanent magnet as shown in FIGS. 22A and 22B. However, as illustrated in FIGS. 23A and 23B, a magnet provided in a magnetic field generating apparatus may be provided as an electromagnet formed of coils 200N and 200S. In this case, the synchronization control unit may form a magnetic field by supplying a current to the magnetic field generating apparatus separately from delivering the current to the coil provided in the insertion structure.

As illustrated in FIGS. 23A and 23B, when an electromagnet is formed by using a set of coils, the set 200N of coils may form an N pole of a magnet, and the set 200S of other coils may form an S pole of a magnet.

In the meantime, a configuration of a magnetic field generating unit described with reference to FIGS. 22A, 22B, 23A, and 23B is only one embodiment of the inventive concept. There is no limitation on a physical form and an operation form of the magnet constituting the magnetic field generating unit.

Figure 24:
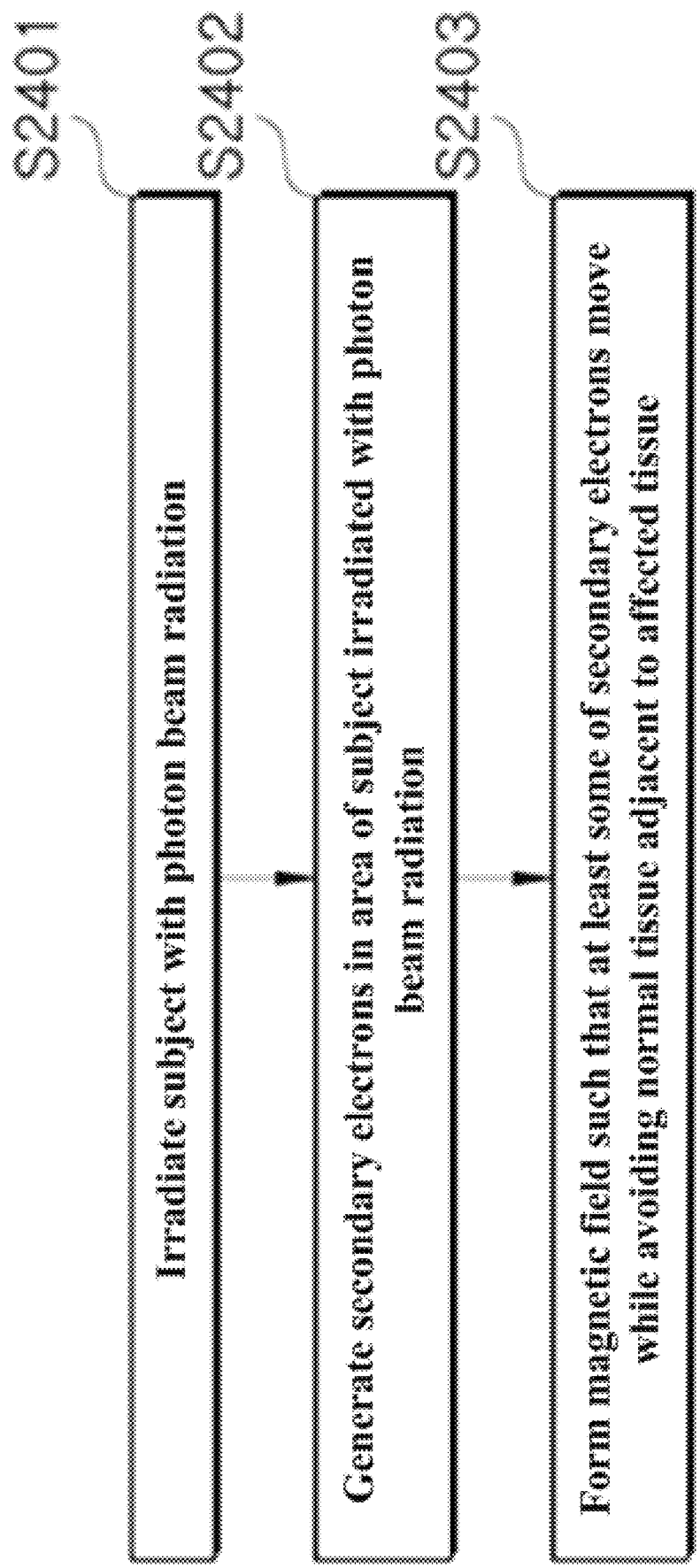
FIG. 24 is a flowchart, according to an embodiment of the inventive concept.

FIG. 24 is a flowchart, according to an embodiment of the inventive concept.

Referring to FIG. 24, it is possible to irradiate a subject with photon beam radiation through a radiation generating unit of a radiation generating apparatus (S2401).

Furthermore, it is possible to induce the generation of secondary electrons in an area of a subject irradiated with photon beam radiation through a radiation generating unit of the radiation generating apparatus (S2402).

Moreover, it is possible to form a magnetic field in the area where secondary electrons are generated through the magnetic field generating unit of the radiation generating apparatus (S2403).

In the meantime, in forming a magnetic field, a magnetic field may be formed such that at least some of the secondary electrons move while avoiding an affected tissue based on a relationship between the area irradiated with photon beam radiation and a location of the affected part.

The inventive concept has the following various effects.

According to an embodiment of the inventive concept, power used in a magnetic field generating unit may be reduced to reduce heat generation, and thus an internal component such as a cooling device may be excluded or reduced.

Moreover, according to an embodiment of the inventive concept, a duty factor, caloric value, and external leakage of the magnetic field of a magnetic field generating unit may be reduced by synchronizing a radiation pulse with a magnetic field pulse, and a magnetic field generating apparatus may be miniaturized.

Furthermore, according to an embodiment of the inventive concept, it is possible to minimize a magnetic field influence on parts sensitive to a magnetic field in a magnetic field generating apparatus by placing the magnetic field generating unit in an inner area of a magnetic field shield unit. Accordingly, it is possible to increase a central magnetic field by focusing an external leakage magnetic field to the inside.

Also, according to an embodiment of the inventive concept, while the amount of radiation delivered to normal tissue is optimized by irradiating photon beam radiation to a patient's affected tissue (e.g., tumor portion), forming a magnetic field area in the patient's body at the same time, and adjusting the direction, intensity and phase of a magnetic field in the magnetic field area, side effects of radiation are minimized and thus restrictions on the amount of radiation delivered to a treatment portion are removed. Accordingly, the treatment effect by the photon beam radiation may be improved.

Besides, a magnetic field parallel to a radiation beam direction may be formed, and thus the divergence of scattering charged particles may be prevented and the scattered charged particles may be concentrated. Accordingly, because the amount of radiation delivered to a tumor surface of a treatment target may be strengthened, the radiation treatment effect may be improved and, at the same time, the damage to the surrounding normal tissue due to the use of additional radiation and the divergence of scattered charged particles may be reduced, and thus radiation side effects may be reduced.

Although an embodiment of the inventive concept are described with reference to the accompanying drawings, it will be understood by those skilled in the art to which the inventive concept pertains that the inventive concept may be carried out in other detailed forms without changing the scope and spirit or the essential features of the inventive concept. Therefore, the embodiments described above are provided by way of example in all aspects, and should be construed not to be restrictive.

While the inventive concept has been described with reference to embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A magnetic field generating apparatus operating in conjunction with a radiation treatment device for treating affected tissue of a subject by using photon beam radiation, the apparatus comprising:
   a magnetic field generating unit configured to form a magnetic field inside the subject; and
   a synchronization control unit configured to synchronize a radiation pulse corresponding to the photon beam radiation with a magnetic field pulse corresponding to the magnetic field,
   wherein the synchronization control unit sets a magnetic field generation time range such that a secondary electron generation section generated due to irradiation of the photon beam radiation is included in the magnetic field generation time range after the magnetic field reaches a target value.

2. The apparatus of claim 1, wherein the synchronization control unit operates in conjunction with a radiation amount control unit of the radiation treatment device, and
   wherein the synchronization control unit receives an output period of the photon beam radiation from the radiation amount control unit and synchronizes an output period of the photon beam radiation with an output period of the magnetic field.

3. The apparatus of claim 1, further comprising:
a pulse detection unit configured to detect the photon beam radiation,
wherein the synchronization control unit obtains an output period of the photon beam radiation by analyzing the detected photon beam radiation.

4. The apparatus of claim 1, wherein the synchronization control unit sets a magnetic field generation time range in consideration of a delay time required until the magnetic field reaches a target value.

5. The apparatus of claim 1, wherein the affected tissue, normal tissue, and low-density space are located inside the subject, and the low-density space is adjacent to at least one of the affected tissue or the normal tissue, and
wherein the magnetic field generating unit forms the magnetic field in the low-density space.

6. The apparatus of claim 1, wherein the magnetic field generating unit includes an electromagnet, a permanent magnet, and a combination of the electromagnet and the permanent magnet, and
wherein the magnetic field generating unit rotates around the subject, or is positioned along a periphery of the subject in a fixed or floating manner.

7. The apparatus of claim 1, wherein the magnetic field generating unit includes a plurality of electromagnets, a plurality of permanent magnets, or a combination of the plurality of electromagnets and the plurality of permanent magnets, which are arranged in a left-right symmetrical structure, based on an axis on which the radiation is irradiated.

8. The apparatus of claim 7, further comprising:
a plate-shaped frame in which the subject is seated and in which the electromagnets, the permanent magnets, or the combination are positioned,
wherein the plate-shaped frame includes a space in which the electromagnets, the permanent magnets, or the combination moves.

9. A radiation treatment device operating for treating affected tissue of a subject by using photon beam radiation, comprising:
a magnetic field generating apparatus comprising:
a magnetic field generating unit configured to form a magnetic field inside the subject; and
a synchronization control unit configured to synchronize a radiation pulse corresponding to the photon beam radiation with a magnetic field pulse corresponding to the magnetic field,
wherein the synchronization control unit sets a magnetic field generation time range such that a secondary electron generation section generated due to irradiation of the photon beam radiation is included in the magnetic field generation time range after the magnetic field reaches a target value; and
a radiation generating unit configured to irradiate radiation to the affected tissue of the subject.

10. A radiation and magnetic field generating apparatus irradiating photon beam radiation to in-body affected tissue of a subject, the apparatus comprising:
a radiation generating unit configured to irradiate the photon beam radiation to the subject and to induce generation of secondary electrons in an area of the subject where the photon beam radiation is irradiated;
a magnetic field generating unit, which is provided to be inserted into a body, which includes an insertion structure for forming a low-density space, and which is configured to form a magnetic field in an area in which the secondary electrons are generated; and
a synchronization control unit configured to:
control formation of the magnetic field such that at least part of the secondary electrons moves to the low-density space based on a relationship between an area where the photon beam radiation is irradiated and a location of an affected part; and
control the formation of the magnetic field such that the secondary electrons move while avoiding normal tissue adjacent to the affected tissue,
wherein a shape of the insertion structure is determined based on the relationship between the area where the photon beam radiation is irradiated and the location of the affected part.

11. The apparatus of claim 10, wherein the insertion structure is inserted into the body, and is provided as a balloon structure that forms the low-density space through formation of a predetermined volume.

12. The apparatus of claim 10, wherein the magnetic field generating unit includes:
at least one coil; and
a capacitor element, and
wherein the synchronization control unit forms the magnetic field by controlling a current supplied to the at least one coil based on the relationship between the area where the photon beam radiation is irradiated and the location of the affected part.

13. The apparatus of claim 12, wherein the magnetic field generating unit is provided such that the magnetic field in a form of a pulse is generated by receiving pulse power, and
wherein the synchronization control unit allows the pulse power to be supplied to the magnetic field generating unit such that the magnetic field is formed in a state where a caloric value generated by the magnetic field generating unit is not greater than a predetermined value.

14. The apparatus of claim 12, wherein the synchronization control unit includes size information of the subject, includes identification information corresponding to the subject, and controls the formation of the magnetic field based on the identification information.

15. The apparatus of claim 12, wherein the magnetic field generating unit is provided in a catheter structure including a first area provided to be inserted into the body and a second area excluding the first area, and
wherein the at least one coil is provided in the first area, and the capacitor is provided in the second area.

16. The apparatus of claim 10, wherein the synchronization control unit changes a location of at least one magnet or the location of the subject such that an angle between a magnetic force line corresponding to the magnetic field and an irradiation direction of the photon beam radiation is orthogonal.

17. The apparatus of claim 10, wherein the synchronization control unit controls the formation of the magnetic field such that density of the secondary electrons reaching the normal tissue per unit area is less than a predetermined value.

18. The apparatus of claim 17, wherein the synchronization control unit controls formation of the photon beam radiation such that density of the secondary electrons reaching the affected part per unit area is greater than a predetermined value.

19. A method of controlling a radiation and magnetic field generating apparatus irradiating photon beam radiation to an in-body affected tissue of a subject, the method comprising:

irradiating the photon beam radiation to the subject through a radiation generating unit of the magnetic field generating apparatus;

inducing generation of secondary electrons in an area of the subject irradiated with the photon beam radiation through the radiation generating unit of the magnetic field generating apparatus; and forming a magnetic field in an area where the secondary electrons are generated, through the magnetic field generating unit of the radiation generating apparatus, wherein the forming of the magnetic field includes:

forming the magnetic field such that at least some of the secondary electrons move while avoiding the affected tissue based on a relationship between an area where the photon beam radiation is irradiated and a location of an affected part, and wherein the forming of the magnetic field includes:

allowing pulse power to be supplied to the magnetic field generating unit such that the magnetic field is formed in a state where a caloric value generated by the magnetic field generating unit is not greater than a predetermined value.

* * * * *